US010254270B2

(12) United States Patent
Potyrailo et al.

(10) Patent No.: US 10,254,270 B2
(45) Date of Patent: Apr. 9, 2019

(54) SENSING SYSTEM AND METHOD

(71) Applicant: General Electric Company, Schenectady, NY (US)

(72) Inventors: Radislav Alexandrovich Potyrailo, Niskayuna, NY (US); Michael Garry, Greenville, SC (US); John Mihok, Schenectady, NY (US); Robert Mcleod, Fair Play, SC (US)

(73) Assignee: General Electric Company, Schenectady, NY (US)

( * ) Notice: Subject to any disclaimer, the term of this patent is extended or adjusted under 35 U.S.C. 154(b) by 94 days.

(21) Appl. No.: 15/418,847

(22) Filed: Jan. 30, 2017

(65) Prior Publication Data
US 2017/0138922 A1 May 18, 2017

Related U.S. Application Data

(63) Continuation-in-part of application No. 14/866,320, filed on Sep. 25, 2015, now Pat. No. 10,018,613, and (Continued)

(51) Int. Cl.
*G01N 27/02* (2006.01)
*G01N 33/28* (2006.01)
*G01M 13/021* (2019.01)

(52) U.S. Cl.
CPC ...... *G01N 33/2888* (2013.01); *G01M 13/021* (2013.01); *G01N 27/026* (2013.01)

(58) Field of Classification Search
CPC ........... G01N 33/2835; G01N 33/2847; G01N 33/2876; G01N 33/2888; G01N 27/026;
(Continued)

(56) References Cited

U.S. PATENT DOCUMENTS 5,750,887 A 5/1998 Schricker
6,359,444 B1 * 3/2002 Grimes .................. G01N 22/00
324/633
(Continued)

OTHER PUBLICATIONS

Potyrailo, R. A., "Multivariable Sensors for Ubiquitous Monitoring of Gases in the Era of Internet of Things and Industrial Internet", Chemical Reviews, Sep. 7, 2016, 116, pp. 11877-11923, American Chemical Society, (47 pages).
(Continued)

*Primary Examiner* — Natalie Huls
(74) *Attorney, Agent, or Firm* — GE Global Patent Operation; Nitin N. Joshi

(57) ABSTRACT

A system includes a resonant sensor in contact with oil within a gearbox of a rotor system, such as a wind turbine, and one or more processors. The sensor includes electrodes and a sensing circuit that generates electrical stimuli having frequencies applied to the oil at different times during a life of the gearbox. The processors receive electrical signals from the resonant sensor representative of impedance responses of the oil to the electrical stimuli. The processors analyze the impedance responses and determine a concentration of a polar analyte in the oil at different times. The processors calculate a degradation value for the gearbox based on the concentration of the polar analyte. Responsive to the degradation value exceeding a designated threshold, the processors at least one of schedule maintenance for the rotor system, provide an alert to schedule maintenance, or prohibit operation of the rotor system until maintenance is performed.

22 Claims, 74 Drawing Sheets

Related U.S. Application Data a continuation-in-part of application No. 14/421,245, filed on Feb. 12, 2015, now Pat. No. 9,746,452, and a continuation-in-part of application No. 14/585,690, filed on Dec. 30, 2014, and a continuation-in-part of application No. 14/532,168, filed on Nov. 4, 2014, now Pat. No. 9,536,122, and a continuation-in-part of application No. 14/031,965, filed on Sep. 19, 2013, now Pat. No. 8,990,025, and a continuation-in-part of application No. 14/031,951, filed on Sep. 19, 2013, now Pat. No. 9,037,418, and a continuation-in-part of application No. 13/838,884, filed on Mar. 15, 2013, now Pat. No. 9,389,296, and a continuation-in-part of application No. 13/729,800, filed on Dec. 28, 2012, now Pat. No. 9,097,639, and a continuation-in-part of application No. 13/729,851, filed on Dec. 28, 2012, now Pat. No. 9,261,474, and a continuation-in-part of application No. 13/630,587, filed on Sep. 28, 2012, now Pat. No. 9,658,178, and a continuation-in-part of application No. 13/630,939, filed on Sep. 28, 2012, now Pat. No. 9,389,260, and a continuation-in-part of application No. 13/630,954, filed on Sep. 28, 2012, now Pat. No. 9,147,144, and a continuation-in-part of application No. 13/630,739, filed on Sep. 28, 2012, now Pat. No. 9,176,083, and a continuation-in-part of application No. 13/558,499, filed on Jul. 26, 2012, now Pat. No. 9,195,925, and a continuation-in-part of application No. 13/538,570, filed on Jun. 29, 2012, now Pat. No. 9,538,657, and a continuation-in-part of application No. 13/484,674, filed on May 31, 2012, now Pat. No. 9,052,263, and a continuation-in-part of application No. 13/331,003, filed on Dec. 20, 2011, now Pat. No. 9,045,973, and a continuation-in-part of application No. 12/977,568, filed on Dec. 23, 2010, now abandoned, and a continuation-in-part of application No. 12/827,623, filed on Jun. 30, 2010, now Pat. No. 8,936,191, and a continuation-in-part of application No. 12/824,436, filed on Jun. 28, 2010, and a continuation-in-part of application No. 12/424,016, filed on Apr. 15, 2009, now Pat. No. 8,364,419, and a continuation-in-part of application No. 12/325,653, filed on Dec. 1, 2008, now abandoned, and a continuation-in-part of application No. 11/560,476, filed on Nov. 16, 2006, now Pat. No. 9,589,686.

(60) Provisional application No. 61/987,853, filed on May 2, 2014, provisional application No. 61/692,230, filed on Aug. 22, 2012.

(58) Field of Classification Search
CPC ............ F01M 11/10; F01M 11/12; F01M 2011/1406; F01M 2011/146; F01M 2011/1473
See application file for complete search history.

(56) References Cited

U.S. PATENT DOCUMENTS

| | | | |
|---|---|---|---|
| 6,456,928 B1 | 9/2002 | Johnson | |
| 6,741,938 B2* | 5/2004 | Berndorfer | F01M 11/10 |
| | | | 701/29.5 |
| 6,853,951 B2 | 2/2005 | Jarrell et al. | |
| 6,941,202 B2 | 9/2005 | Wilson et al. | |
| 7,043,402 B2 | 5/2006 | Phillips et al. | |
| 7,317,989 B2 | 1/2008 | Difoggio et al. | |
| 7,322,794 B2 | 1/2008 | Lemieux et al. | |
| 7,395,188 B1* | 7/2008 | Goebel | G05B 19/4184 |
| | | | 702/184 |
| 7,562,557 B2 | 7/2009 | Bennett et al. | |
| 7,571,057 B2 | 8/2009 | D Amato et al. | |
| 7,581,434 B1 | 9/2009 | Discenzo et al. | |
| 7,677,869 B2 | 3/2010 | Martinez et al. | |
| 7,832,980 B2 | 11/2010 | Demtroder et al. | |
| 7,911,345 B2* | 3/2011 | Potyrailo | G06K 7/0095 |
| | | | 340/10.1 |
| 7,914,250 B2 | 3/2011 | Behera et al. | |
| 7,928,741 B2* | 4/2011 | Hedges | G01N 33/2888 |
| | | | 324/698 |
| 7,941,281 B2 | 5/2011 | Rai et al. | |
| 7,996,183 B2 | 8/2011 | Takeda et al. | |
| 8,318,099 B2 | 11/2012 | Potyrailo et al. | |
| 8,326,577 B2 | 12/2012 | Graham et al. | |
| 8,468,871 B2* | 6/2013 | Potyrailo | G01N 27/021 |
| | | | 73/19.01 |
| 8,718,953 B2 | 5/2014 | Rajagopalan et al. | |
| 8,924,162 B2 | 12/2014 | Lapira et al. | |
| 8,936,191 B2 | 1/2015 | Potyrailo et al. | |
| 9,014,775 B2 | 4/2015 | Bennett et al. | |
| 9,147,144 B2 | 9/2015 | Potyrailo et al. | |
| 2003/0222656 A1* | 12/2003 | Phillips | G01N 27/02 |
| | | | 324/605 |
| 2005/0171736 A1 | 8/2005 | Kang | |
| 2005/0179449 A1* | 8/2005 | Wooton | G01N 33/2888 |
| | | | 324/691 |
| 2008/0172187 A1 | 7/2008 | Koehler et al. | |
| 2009/0120169 A1* | 5/2009 | Chandler, Jr. | G01N 9/002 |
| | | | 73/54.41 |
| 2009/0092491 A1 | 9/2009 | Cairo et al. | |
| 2011/0020122 A1 | 1/2011 | Parthasarathy et al. | |
| 2011/0196593 A1 | 11/2011 | Jiang et al. | |
| 2011/0125419 A1 | 12/2011 | Bechhoefer et al. | |
| 2012/0025529 A1* | 2/2012 | Davis | F16N 29/04 |
| | | | 290/44 |
| 2012/0116683 A1 | 5/2012 | Potyrailo et al. | |
| 2012/0161787 A1 | 6/2012 | Potyrailo et al. | |
| 2012/0229152 A1* | 9/2012 | Katafuchi | G01N 27/414 |
| | | | 324/672 |
| 2012/0235690 A1 | 9/2012 | Potyrailo et al. | |
| 2013/0141117 A1* | 6/2013 | Nikolenko | G01N 27/028 |
| | | | 324/655 |
| 2013/0154847 A1* | 6/2013 | Potyrailo | E21B 47/10 |
| | | | 340/856.3 |
| 2013/0176038 A1* | 7/2013 | Wherritt | G01N 27/221 |
| | | | 324/675 |
| 2013/0304312 A1* | 11/2013 | Dorr | F01M 11/12 |
| | | | 701/34.4 |
| 2015/0115983 A1 | 4/2015 | Potyrailo et al. | |
| 2015/0292675 A1* | 10/2015 | Schjott | F16N 29/00 |
| | | | 184/6.4 |
| 2016/0018381 A1 | 1/2016 | Potyrailo et al. | |
| 2016/0061805 A1 | 3/2016 | Prabhu et al. | |
| 2016/0018727 A1 | 6/2016 | Potyrailo et al. | |
| 2017/0002921 A1* | 1/2017 | Ture | F16H 57/0405 |
| 2017/0138922 A1* | 5/2017 | Potyrailo | G01N 33/2888 |

OTHER PUBLICATIONS

Buhrdorf et al., "Multiparameteric Oil Condition Sensor Based on the Tuning Fork Technology for Automotive Applications", In Advanced Microsystems for Automotive Applications, pp. 289-298, 2005.

Palacios et al., "Supramolecular Chemistry Approach to the Design of a High-Resolution Sensor Array for Multianion Detection in Water", J. Am Chem. Soc., pp. 7538-7544, vol. 129, 2007.

Hempel et al., "Application of a Portable RF Impedance Spectrum Analyzer for the Investigation of Lateral Field Excited Acoustic Wave Sensors in a Liquid Environment", Proceedings—IEEE Ultrasonics Symposium, pp. 373-376, 2007.

Capone et al., "Metal Oxide Gas Sensor Array for the Detection of Diesel Fuel in Engine Oil", Sens. Actuators B, pp. 125-133, vol. 131, 2008.

Hempel et al., "Lateral Field Excited Quartz Crystal Resonator Sensors for Determination of Acoustic and Electrical Properties of

(56) References Cited

OTHER PUBLICATIONS

Liquids", IEEE International Frequency Control Symposium, pp. 705-710, 2008.

Guan et al., "Engine Lubricating Oil Classification by SAE Grade and Source Based on Dielectric Spectroscopy Data", Anal. Chin. Acta, pp. 117-120, vol. 628, 2008.

Lim et al., "An Optoelectronic Nose for the Detection of Toxic Gases", Nature Chemistry, pp. 562-567, 2009.

Mccann et al., "Recent Advances in Lateral Field Excited and Monolithic Spiral Coil Acoustic Transduction Bulk Acoustic Wave Sensor Platforms", Meas. Sci. Tech., vol. 20, 2009.

Cho et al., "Capacitive Sensor for Automotive Engine Oil Degradation using Wireless Network", International Symposium on Advanced Packaging Materials: Microtech, APM '10, pp. 88-91, 2010.

Liu et al., "Measurement of Density and Viscosity of Dodecane and Decane with a Piezoelectric Tuning Fork Over 298-448 K and 0.1-137.9 MPa", Sens. Actuators A 2011, pp. 347-353, vol. 167, 2011.

Guan et al., "Application of Dielectric Spectroscopy for Engine Lubricating Oil Degradation Monitoring", Sens. Actuators A, pp. 22-29, vol. 168, 2011.

Wang et al., "Impedance Analysis for Lateral Field Excited Acoustic Wave Sensors", Sens. Actuators B, pp. 969-975, vol. 156, 2011.

Latif et al., "Conductometric Sensors for Monitoring Degradation of Automotive Engine Oil", Sensors, pp. 8611-8625, vol. 11, 2011.

Perez et al., Low-cost Oil Quality Sensor Based on Changes in Complex Permittivity, Sensors, pp. 10675-10690, vol. 11, 2011.

Sen et al, "Evaluation of Sensor Arrays for Engine Oils using Artificial Oil Alteration", Proc. SPIE, 8066, 2011.

Fochtmann et al., "Optimization of the Lateral Field Excited Platform for Liquid Sensing Applications", Sens. Actuators B, pp. 95-103, vol. 170, 2012.

Hussain et al., "Vibration Analysis and Time Series Prediction for Wind Turbine Gearbox Prognostics", International Journal of Prognostics and Health Management, Jan. 4, 2013.

De Souza et al., "A Close Dielectric Spectroscopic Analysis of Diesel/Biodiesel Blends and Potential Dielectric Approaches for Biodiesel Content Assessment", Fuel Cells, pp. 705-710, vol. 105, 2013.

Hamilton et al., "Development of a Novel Wear Detection System for Wind Turbine Gearboxes", IEEE Sensors Journal, pp. 465-473, vol. 14, Issue 2, Oct. 9, 2013.

Odgaard et al., "Frequency based Wind Turbine Gearbox Fault Detection Applied to a 750 kW Wind Turbine", IEEE Conference on Control Applications (CCA), pp. 1383-1388, Oct. 8-10, 2014.

Igba et al., "Performance Assessment of Wind Turbine Gearboxes using in-service data: Current approaches and future trends", Renewable and Sustainable Energy Reviews, pp. 144-159, vol. 50, Oct. 2015.

\* cited by examiner

SENSING SYSTEM AND METHOD

CROSS-REFERENCE TO RELATED APPLICATIONS

This application is a continuation-in-part of U.S. patent application Ser. No. 14/866,320, filed on 25 Sep. 2015 (the "'320 Application"). The '320 Application is a continuation-in-part of U.S. patent application Ser. No. 14/421,245, filed on 12 Feb. 2015 (the "'245 Application"), which claims the benefit of U.S. Provisional Patent Application No. 61/692,230, filed on 22 Aug. 2012 (the "'230 Application").

The '320 Application also is a continuation-in-part of U.S. patent application Ser. No. 14/585,690, filed on 30 Dec. 2014 (the "'690 Application"), which claims priority to U.S. Provisional Patent Application No. 61/987,853, filed on 2, May 2014 (the "'853 Application"). The '690 Application is a continuation-in-part of the following applications: U.S. patent application Ser. No. 11/560,476, filed on 16 Nov. 2006 (the "'476 Application"), U.S. patent application Ser. No. 12/325,653, filed on 1 Dec. 2008 (the "'653 Application"), U.S. patent application Ser. No. 12/824,436, filed on 28 Jun. 2010 (the "'436 Application"), U.S. patent application Ser. No. 12/827,623, filed on 30 Jun. 2010 (the "'623 Application") now U.S. Pat. No. 8,936,191 issued 20 Jan. 2015, U.S. patent application Ser. No. 12/977,568, filed on 23 Dec. 2010 (the "'568 Application"), U.S. patent application Ser. No. 13/331,003, filed on 20 Dec. 2011 (the "'003 Application") now U.S. Pat. No. 9,045,973 issued 2 Jun. 2015, U.S. patent application Ser. No. 13/484,674, filed on 31, May 2012 (the "'674 Application") now U.S. Pat. No. 9,052,263 issued 9 Jun. 2015, U.S. patent application Ser. No. 13/538,570, filed on 29 Jun. 2012 (the "'570 Application"), U.S. patent application Ser. No. 13/558,499, filed on 26 Jul. 2012 (the "'499 Application" now U.S. Pat. No. 9,195,925 issued 24 Nov. 2015, U.S. patent application Ser. No. 13/630,939, filed on 28 Sep. 2012 (the "'939 Application") now U.S. Pat. No. 9,389,260 issued 12 Jul. 2015, U.S. patent application Ser. No. 13/630,954, filed on 28 Sep. 2012 (the "'954 Application") now U.S. Pat. No. 9,147,144 issued 29 Sep. 2015, U.S. patent application Ser. No. 13/630,587, filed on 28 Sep. 2012 (the "'587 Application"), U.S. patent application Ser. No. 13/630,739, filed on 28 Sep. 2012 (the "'739 Application") now U.S. Pat. No. 9,176,083 issued 3 Nov. 2015, U.S. patent application Ser. No. 13/729,800, filed on 28 Dec. 2012 (the "'800 Application") now U.S. Pat. No. 9,097,639 issued 4 Aug. 2015, U.S. patent application Ser. No. 13/729,851, filed on 28 Dec. 2012 (the "'851 Application") now U.S. Pat. No. 9,261,474 issued 16 Feb. 2016, U.S. patent application Ser. No. 13/838,884, filed on 15 Mar. 2013 (the "'884 Application") now U.S. Pat. No. 9,389,296 issued 12 Jul. 2016, U.S. patent application Ser. No. 14/031,951, filed on 19 Sep. 2013 (the "'951 Application") now U.S. Pat. No. 9,037,418 issued 19, May 2015, U.S. patent application Ser. No. 14/031,965, filed on 19 Sep. 2013 (the "'965 Application") now U.S. Pat. No. 8,990,025 issued 24 Mar. 2015, and U.S. patent application Ser. No. 14/532,168, filed on 4 Nov. 2014 (the "'168 Application"). The '674 Application is a continuation-in-part of U.S. patent application Ser. No. 12/424,016, filed on 15 Apr. 2009, and is now U.S. Pat. No. 8,364,419, issued on 29 Jan. 2013 (the "'419 Patent").

All the aforementioned applications and patent are incorporated herein by reference in their entireties.

FIELD

One or more embodiments are disclosed that relate to asset monitoring systems and methods using resonant sensors. The resonant sensors may include inductor-capacitor-resistor (LCR) resonant circuits that can be used for monitoring properties of fluids.

BACKGROUND

Many industrial machines (e.g., wind turbines, locomotives, trucks, earth-moving equipment, and the like) include assets or assemblies (e.g., mechanical drive trains, engines, gearboxes, and the like) that operate within difficult environments and/or endure substantial amounts of thermal or torsional stress as well as shock and vibration. It is often desirable to monitor a condition of an element or assembly so that it may be replaced or repaired before severe and permanent damage is sustained by the machine. Often, fluid lubricants are used to provide lubrication and cooling to increase performance of the machine and/or to increase the operational lifetime of the machine. Lubricants reduce the friction between two parts that engage each other and may also dissipate heat that is generated by the friction between the two parts. In addition to lubricants, machines may use other industrial fluid such as fuels, hydraulic media, drive fluids, power steering fluids, power brake fluids, drilling fluids, oils, insulating fluids, heat transfer fluids, or the like. Such fluids allow efficient and safe operation of machinery in transportation, industrial, locomotive, marine, automotive, construction, medical, and other applications.

The quality of a lubricant may decrease over time due to the introduction of contaminants and/or aging of the lubricant. Lubricants in a reservoir can become contaminated by contaminants such as water, metallic particles, and non-metallic particles. Contaminated fluids may lead to damaged parts or a decreased performance of the machine. Water is a common and destructive lubricant contaminant. The water may be introduced from a coolant leak, condensation from environmental exposure, equipment cleaning, and/or combustion. Water adversely affects the lubricant properties by increasing engine wear, causing corrosion of the reservoir, and/or accelerating oxidation of the lubricating fluid, such as oil. In addition, the repetitive thermal and viscous cycles in normal operation conditions may cause the lubricating fluid to age and chemically break down, which results in a reduction in lubricating performance of the fluid, such as an increased viscosity. Furthermore, stabilizing additives that are added to the lubricants to provide increased resilience within harsh environments, such as high temperatures, may begin to break down over time as well. The reduction in additive concentration provides less thermal stability for the lubricant, causing the lubricant to degrade at a faster rate. As the additive is depleted, acidic components, such as by-products from the degradation of the additive and/or the lubricant due to aging, may be introduced into the lubricant fluid. The acidic components, like water, are polar contaminants that reduce the effectiveness and performance of the lubricant.

Conventional methods of inspecting fluids of a machine include visual inspection of the fluid (e.g., dipsticks) or a sensor that is directly wired to a system. These methods may not be practical and/or may have limited capabilities. For example, due to the configuration of some machines, it may be difficult to visually inspect the fluid. Also, hardwired sensors may not be suitable for machines that frequently move and/or are exposed to harsh conditions.

Robust sensing of fluids may be useful in mobile and stationary equipment applications. As an example, if the equipment is a vehicle engine and the fluid is engine oil, then knowledge about oil health may be used to help reduce or prevent unexpected downtime, provide savings from unnecessary oil replacement, extend the operating lifetime of the oil and/or the asset (e.g., gearbox, engine, etc.) in which the oil is disposed, and improve service intervals scheduling.

Standard (classic) impedance spectroscopy is a technique that is employed to characterize aspects of material performance. In classic impedance spectroscopy, a material may be positioned between electrodes and probed over a wide frequency range (from a fraction of Hz to tens of GHz) to extract the fundamental information about dielectric properties of the material. Standard impedance spectroscopy may be limited due to its low sensitivity in reported measurement configurations and prohibitively long acquisition times over the broad frequency range. Therefore, standard impedance spectroscopy is difficult to perform in the field.

It may be desirable to have systems and methods for in-situ monitoring of fluid properties that differ from those systems and methods that are currently available.

BRIEF DESCRIPTION

In one or more embodiments, a system is provided that includes a resonant sensor and one or more processors. The resonant sensor is configured to be in contact with oil within a gearbox of a rotor system. The sensor includes electrodes and a sensing region circuit that is configured to generate electrical stimuli at different times during an operational life of the gearbox. Each electrical stimulus has multiple different frequencies that are applied to the oil via the electrodes. The one or more processors are configured to receive multiple electrical signals from the resonant sensor. The electrical signals are representative of impedance responses of the oil to the electrical stimuli. The one or more processors are configured to analyze the impedance responses and determine a concentration of a polar analyte in the oil at each of the different times based on the impedance responses. The one or more processors are further configured to calculate a degradation value for the gearbox based on the concentration of the polar analyte in the oil. Responsive to the degradation value exceeding a designated degradation threshold, the one or more processors are configured to at least one of schedule maintenance for the rotor system, provide an alert to schedule maintenance for the rotor system, or prohibit operation of the rotor system until maintenance is performed on the rotor system.

In one or more embodiments, a method is provided that includes obtaining multiple measurements of a concentration of at least one polar analyte in oil within a gearbox of a rotor system. The measurements are obtained at different times during an operational life of the gearbox via a resonant sensor in operational contact with the oil. The resonant sensor includes electrodes and a sensing region circuit that is configured to generate an electrical stimulus having multiple different frequencies that are applied to the oil via the electrodes. The concentration of the at least one polar analyte in the oil is determined based on an impedance response of the oil to the electrical stimulus. The method also includes calculating a degradation value for the gearbox based on the concentration of the at least one polar analyte in the oil within the gearbox. Responsive to the degradation value exceeding a designated degradation threshold, the method includes at least one of scheduling maintenance for the rotor system, providing an alert to schedule maintenance for the rotor system, or prohibiting operation of the rotor system until maintenance is performed on the rotor system.

In one or more embodiments, a system is provided that includes a resonant sensor, one or more processors, and an operating condition sensor. The resonant sensor is configured to be in contact with oil within a gearbox of a rotor system. The sensor includes electrodes and a sensing region circuit that is configured to generate electrical stimuli at different times during an operational life of the gearbox. Each electrical stimulus has multiple different frequencies that are applied to the oil via the electrodes. The one or more processors are configured to receive multiple electrical signals from the resonant sensor. The electrical signals are representative of impedance responses of the oil to the electrical stimuli. The one or more processors are configured to analyze the impedance responses and determine a concentration of water in the oil at each of the different times based on the impedance responses. The operating condition sensor is mounted to the rotor system. The operating condition sensor is configured to detect when the rotor system is in a non-operating state and when the rotor system is in an operating state. The one or more processors are configured to calculate a degradation value for the gearbox based on the concentration of water in the oil during time periods that the rotor system is in the non-operating state. Responsive to the degradation value exceeding a designated degradation threshold, the one or more processors are configured to at least one of schedule maintenance for the rotor system, provide an alert to schedule maintenance for the rotor system, or prohibit operation of the rotor system until maintenance is performed on the rotor system.

DETAILED DESCRIPTION

Figure 1:
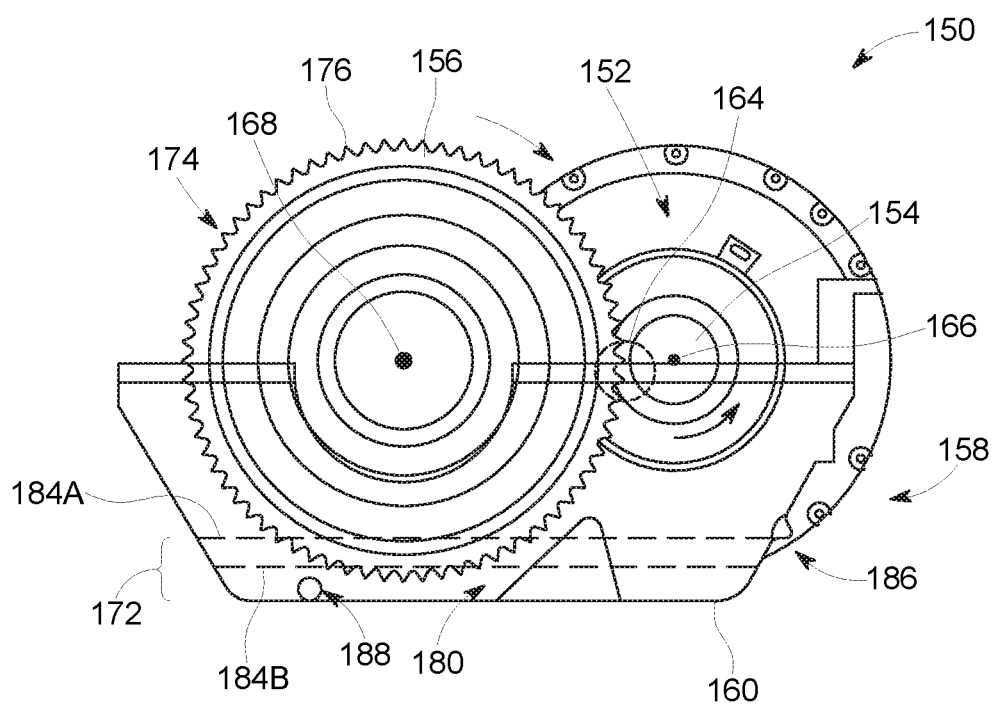
FIG. 1 is a side view of a drive train in accordance with an embodiment.

Embodiments described herein include various systems, assemblies, devices, apparatuses, and methods that may be used in a connection with obtaining one or more measurements of a machine. The measurement(s) may be representative or indicative of an operative condition of the machine. As used herein, an "operative condition of the machine" may refer to an operative condition of the machine as a whole or an operative condition of a component (e.g., element, assembly, or sub-system) of the machine. As used herein, the term "operative condition" relates to a present state or ability of the component and/or a future state or ability. For example, the measurement may indicate that a component is not functioning in a sufficient manner, is damaged, is likely to be damaged if it continues to operate in a designated manner, is not likely to perform appropriately under designated circumstances, and/or is likely to cause damage to other components of the machine.

As an example with respect to locomotives or other rail vehicles, one or more measurements obtained from a locomotive or other rail vehicle may indicate that a lubricant in the component (e.g., drive train, gearbox, engine, and the like) is low or has an insufficient quality.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware and circuit. Thus, for example, one or more of the functional blocks (for example, controllers or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

FIG. 1 is a side view of a drive train (or final drive) 150 in accordance with one embodiment. The drive train 150 includes a traction motor 152, a first (or pinion) gear 154, a second gear 156, and a base portion or shell 160 of a gear case 158. As shown in FIG. 1, the first gear 154 and the second gear 156 engage each other at a gear mesh 164. During operation of the drive train 150 the traction motor 152 drives the first gear 154 by rotating an axle (not shown) coupled to the first gear 154 about an axis of rotation 166. The first gear 154 may be rotated, for example, in a counter-clockwise direction as viewed in FIG. 1. Due to the engagement at the gear mesh 164, the first gear 154 rotates the second gear 156 in a clockwise direction about an axis of rotation 168. The second gear 156 is coupled to an axle (not shown) of a machine (not shown) that rotates with the second gear 156. The machine may be a motive machine, such that the axle of the second gear 156 is coupled to wheels (not shown) of the machine that are rotated with the axle. The wheels engage a surface (e.g., rails or tracks) to move the machine. The machine may be an off-highway vehicle (e.g., vehicles that are not designed or allowed by law or regulation to travel on public roads, highways, and the like). Off-highway vehicles include locomotives, mining vehicles, construction equipment, agricultural equipment, industrial equipment, marine vessels, and the like. In some cases, the vehicle may be part of a vehicle consist in which multiple vehicles are linked directly or indirectly to one another in a common vehicle system (e.g., train). In some embodiments, the machine is an automobile. In alternative embodiments, the machine is not configured to travel. For example, the machine may be a power-generating turbine, such as a windmill or wind turbine, or a component thereof, such as a gearbox.

The gear case 158 includes a reservoir 172 that is configured to hold a lubricant liquid 180 (e.g., oil). The gear case 158 has a fill or inlet port 186 and a drain or outlet port 188. The liquid 180 may be provided to the reservoir 172 through the fill port 186 and drained through the drain port 188.

As shown in FIG. 1, the second gear 156 has teeth 176 along an edge 174 of the second gear 156. When the liquid 180 is held within the gear case 158, the liquid 180 may have a fill level 184. FIG. 1 illustrates a first fill level 184A and a second fill level 184B. The second fill level 184B is lower than the first fill level 184A. In some embodiments, when the drive train 150 is operating properly, the quantity of the liquid 180 correlates to the first fill level 184A such that the edge 174 of the second gear 156 is sufficiently submerged within or bathed by the liquid 180. However, when the fill level is lowered to, for example, the fill level 184B, the edge 174 and teeth 176 may be insufficiently lubricated. Such circumstances may occur when the gear case 158 has a leak. For example, the gear case may become worn and/or damaged over time such that the liquid 180 is permitted to escape the reservoir 172 and/or external contaminants are permitted to enter the reservoir 172.

Other embodiments described herein may be configured to detect other characteristics besides liquid level, such as quality (e.g., degree of contamination) of the liquid. Contaminants may include water, acid, metallic particles, and/or non-metallic particles. Furthermore, embodiments are not limited to the drive train or a gear case of the drive train. For example, measurements may be obtained for any machine including moving parts that use a lubricating fluid, such as a turbo-charger, an air compressor, an engine, and the like.

Additional embodiments are disclosed that relate to sensing methods and systems. The sensors, such as resonant sensors, may include inductor-capacitor-resistor (LCR) sensors that can be used as sensors or transducers for sensing fluids. Provided herein are sensors having a part that is a resonant structure that exhibits resolvable changes in the presence of a fluid and various components or contaminants in the fluid.

In one embodiment, the sensor may include an inductor-capacitor-resistor (LCR) resonator circuit with a resonance frequency response provided by the resonant impedance ($Z$) of this circuit. The sensors as provided herein may be capable of sensing properties of interest in the presence of variable noise sources and operating over the variable temperature conditions to provide stable sensor performance over time. Disclosed herein are sensors that include inductor-capacitor-resistor (LCR) resonators, which may function as a sensor or as a transducer. The resonant impedance spectrum of the sensor may be measured either via inductive coupling between pick up coil and sensor or directly by connecting to a sensor reader. The electrical response of the sensor may be translated into the resonant impedance changes of the sensor.

Non-limiting examples of signal changes of an individual sensor may include combined and simultaneous resonant impedance change, inductance change, resistance change, and capacitance change (referred to herein as electrical characteristics). Suitable sensors and systems disclosed herein may enhance the ability to measure changes in a fluid, such as engine oil or fuel, by contacting it with the sensor between the electrodes that constitute a resonant circuit of the sensor. The resonant circuit of the sensor may be an electrical resonant circuit. Other resonant circuits may include a mechanical resonator, where a change of viscosity and/or density of the fluid cause a response of the mechanical resonators.

Suitable mechanical resonators may include tuning fork resonators, thickness shear mode resonators, quartz crystal microbalance resonators, surface acoustic wave resonators, bulk acoustic wave resonators, and others. Unlike these and other mechanical resonators, the electrical resonators may be not predictably affected by the changes change of viscosity and/or density of the fluid. Instead, electrical resonators may be predictably affected by the changes in the complex permittivity of the fluid. Electrical resonators may be complicated in their design. For example, marginal oscillators require complicated multi-component circuits.

The degradation of at least some oils and lubricants may generate molecules and/or other moieties that may be relatively more polar than the oil and lubricant from which they were formed. The base oil or lubricant may include long chain hydrocarbon molecules that are weakly polar. Thus, the presence of polar contaminants may increase of one or more parts of the oil's complex permittivity.

The degradation of at least some oils and lubricants may generate molecules and/or other moieties that may be relatively low molecular weight and may be in the form of volatiles or gases. For example, an insulating oil of an oil-fitted transformer is employed to insulate and suppress corona and arcing and to serve as a coolant. However, the insulating oil gradually deteriorates under the impact of electrical, thermal and environmental stresses during the life of the transformer. Different types of gases are generated in the insulating oil depending on the deterioration processes. Examples of these gases include hydrogen, carbon monoxide, carbon dioxide, methane, ethane, ethylene, and acetylene. For example, thermal decomposition of mineral oil produces hydrogen and methane. Thermal decomposition of cellulose and other solid insulation materials produces carbon monoxide, carbon dioxide, and water vapor. Such gases are detected and monitored in real time using multivariable sensors as described in more detail below. For this application the sensor is coated with a sensing material that is responsive to one or more gases of interest. When the sensor is in operational contact with the oil, dissolved gases in oil also interact with the sensor and produce a predictable multivariable sensor response. The operational contact may be achieved by direct immersion of the sensor into oil when the sensing material is wetted by oil or through a gas permeable membrane that may allow dissolved gases in oil to diffuse through the membrane to the sensing material while the oil is not wetting the sensing material.

According to one aspect, the resonant transducers operate as re-configurable resonant structures and operate at multiple frequencies for monitoring of a status of fluids (and, further, for example, the health of equipment in contact with such fluids). Monitoring the health of fluids involves a determination of composition or a determination of contamination of such fluid.

Figure 17:
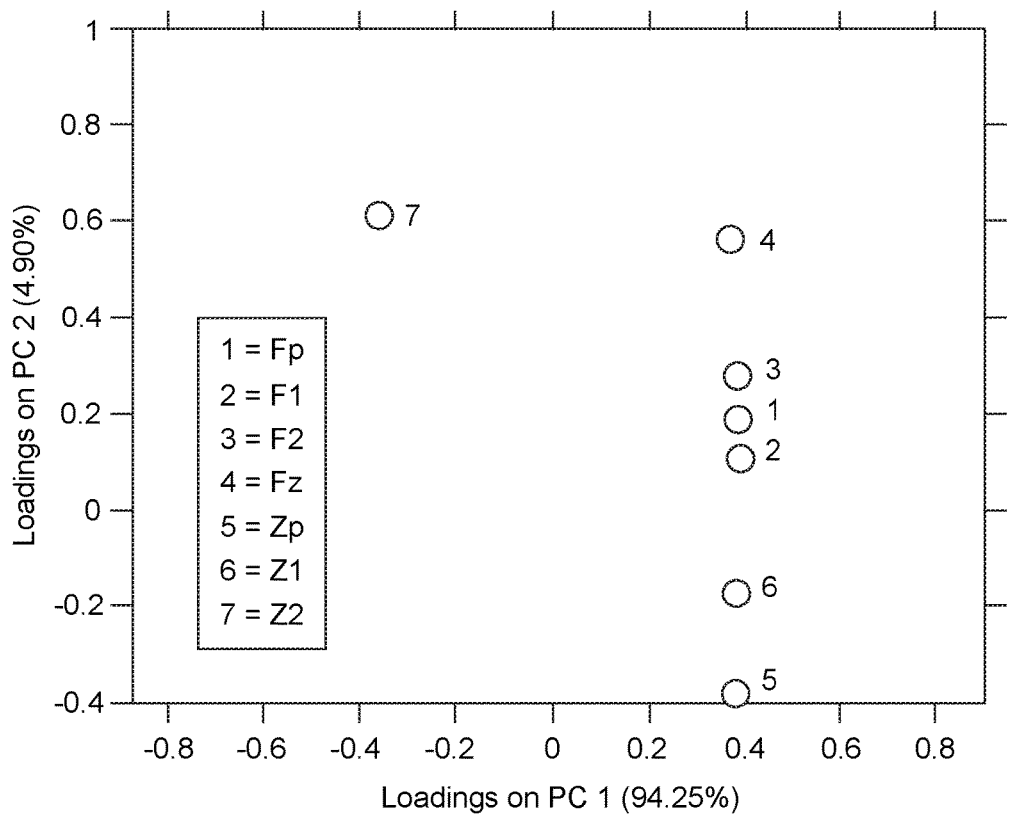
FIG. 17 is a principal components analysis of resonant impedance spectral parameters.

With reference to FIG. 17, a sensing system 1700 is shown that may be useful for assessing a fluid in contact with the sensing system 1700. For purposes of illustration, a representative fluid may be engine oil. The system may include a fluid reservoir 1712 for a fluid and a sensor 1714 disposed in, on, or within the fluid reservoir 1712. Alternatively, the sensor may be set in a flow path of the fluid outside of the reservoir 1712, such as coupled to in-line connectors in fluid communication with the fluid reservoir that define a flow path. In one embodiment, the sensor may provide continuous monitoring of the fluid within the reservoir or flow path.

Suitable fluids may include hydrocarbon fuels and lubricants. Suitable lubricants may include engine oil, gear oil, hydraulic fluid, lubricating oils, synthetic based lubricants, lubricating fluids, greases, silicones, and the like. Suitable fuels may include gasoline, diesel fuel, jet fuel or kerosene, bio-fuels, petrodiesel-biodiesel fuel blends, natural gas (liquid or compressed), and fuel oils. Still other fluids may be insulating oils in transformers, solvents, or mixtures of solvents. Still other fluids may be included with correspondingly appropriate sensor parameters, such as water, air, engine exhaust, biologic fluids, and organic and/or vegetable oils. The fluid may be a liquid, or may in a gaseous phase. Further contemplated are multiphase compositions. The fluids may be disposed in and/or used in connection with the operation of a machine, such as a movable vehicle or a wind turbine.

Non-limiting examples of various fluid components include unintended leaks from proximate systems (e.g., radiator fluid into engine oil, or water condensation in diesel fuel or transformer oil) and/or from fluid-transport devices (e.g., valves, flanges, pipes, tubes). Other detectable fluid components may include degradation products of the fluid caused due to elevated temperature of operation, or due to contact with oxidants (air, others). System operation may introduce fluid components such as dirt, salt, soot or carbon, wear metal particles, wear products, and others. In some environments, fouling due to bacteria or the like may be the fluid component. And in all instances, indirect measurement may be useful, such as a pH decrease that indicates an increased presence of an acidic component. Other detectable fluid components may include external contaminants of the fluid.

The sensor may detect characteristics or properties of the fluid via a resonant impedance spectral response. One or more of the LCR resonators may measure the resonant impedance spectral response. As opposed to simple impedance measurements, the disclosed embodiments probe the sample with at least one resonant electrical circuit. The resonant impedance spectrum of the sensor in proximity to the sample (the sensor in operational contact with the fluid) varies based on sample composition and/or components and/or temperature. The measured resonant impedance values Z' (which may be the real part of resonant impedance, Zre) and Z" (which may be the imaginary part of resonant impedance, Zim) reflect the response of the fluid (for example, the portion of the fluid in proximity to the sensor) to a stimulus of the electric field of the resonant electrical circuit.

The electrical field may be applied by the sensor via electrodes. The electrodes may be in direct or indirect electrical contact with the sample. For example, a sensor may be a combination of a sensing region and associated circuits. The sensing region may be either bare or coated with a protective dielectric layer or a sensing layer. In each of the disclosed cases, the sensing region may be considered to be in operational contact with a fluid. In such embodiments, the sensor circuits may not contact the fluid directly. An example of indirect electrical contact with the sample may be when a sensing electrode structure is coated with a dielectric protective coating and when the electric field that may be generated between the electrodes interacts with the fluid after penetrating through the dielectric protective coating. A suitable dielectric protective coating may be conformally applied to the electrode.

Suitable sensors may include single use or multi-use sensors. A suitable multi-use resonant sensor may be a re-usable sensor that may be used during the lifetime of a system in which it may be incorporated into. In one embodiment, the resonant sensor may be a single use sensor that may be used during all or part of a reaction or process. For example, the resonant sensor may include one or more pairs of electrodes and one or more tuning elements, e.g., a resistor, a capacitor, an inductor, a resonator, impedance transformer, or combinations of two or more thereof to form an inductor-capacitor-resistor (LCR) resonant circuit operated at one or more resonant frequencies. In certain embodiments, different resonant circuits of a plurality of resonant circuits of a resonant sensor may be configured to resonate at different frequencies. Different frequencies may be selected to be across the dispersion profile of the measured fluid composition. The dispersion profile may depend on the dielectric properties of the fluid composition on the probing frequency. Various components of the fluid have different dispersion profiles. When measured at multiple resonance frequencies, concentrations of different components of the fluid may be determined.

Figure 3:
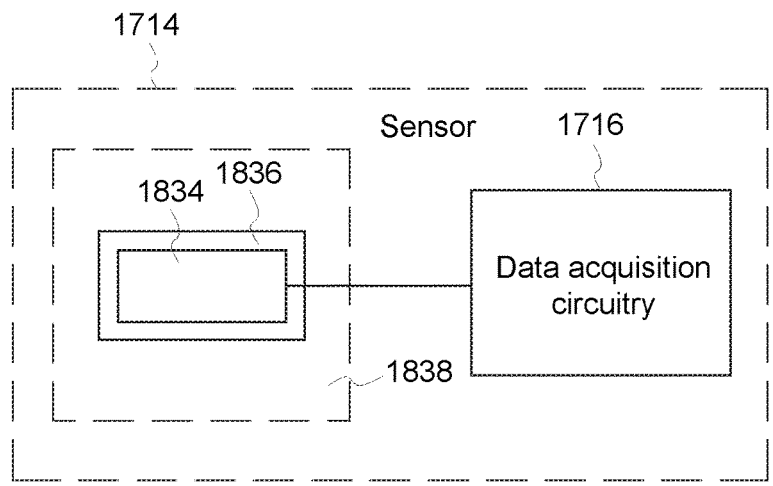
FIG. 3 is a schematic view of a resonant sensor according to an embodiment of the disclosure.

Data from the resonant sensor may be acquired via data acquisition circuitry 1716, which may be associated with the sensor or which may be associated with a control system, such as a controller or workstation 1722 including data processing circuitry, where additional processing and analysis may be performed. The controller or workstation may include one or more wireless or wired components, and may also communicate with the other components of the system. Suitable communication models include wireless or wired. At least one suitable wireless model includes radio frequency devices, such as RFID wireless communications. Other wireless communication modalities may be used based on application specific parameters. For example, where there may be EMF interference certain modalities may work where others may not. The data acquisition circuitry can be disposed within the sensor 1714 as shown in FIG. 3. Other suitable locations may include disposition being within the workstation. Further, the workstation can be replaced with a control system of the whole process where the resonant sensor and its data acquisition circuitry may be connected to the control system of process.

The data acquisition circuitry may be in the form of a sensor reader, which may be configured to communicate wirelessly or wired with the fluid reservoir and/or the workstation. For example, the sensor reader may be a battery-operated device and/or may be powered using energy available from the main control system or by using harvesting of energy from ambient sources (light, vibration, heat, or electromagnetic energy).

Additionally, the data acquisition circuitry may receive data from one or more resonant sensors 1714 (e.g., multiple sensors formed in an array or multiple sensors positioned at different locations in or around the fluid reservoir). The data may be stored in short or long term memory storage devices, such as archiving communication systems, which may be located within or remote from the system and/or reconstructed and displayed for an operator, such as at the operator workstation. The sensors may be positioned on or in fuel or fluid reservoirs, associated piping components, connectors, flow-through components, and any other relevant process components. The data acquisition circuitry may include one or more processors for analyzing the data received from the sensor 1714. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed in the hardware of the one or more processors.

In addition to displaying the data, the operator workstation may control the above-described operations and functions of the system. The operator workstation may include one or more processor-based components, such as general purpose or application-specific computers 1724. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation or by associated components of the system. Alternatively, the programs and routines may be stored on a computer accessible storage and/or memory remote from the operator workstation but accessible by network and/or communication interfaces present on the computer. The computer may also comprise various input/output (I/O) interfaces, as well as various network or communication interfaces. The various I/O interfaces may allow communication with user interface devices, such as a display 1726, keyboard 1728, electronic mouse 1730, and printer 1732, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

The sensor 1714 may include a plurality of resonant circuits that may be configured to probe the fluid in the fluid reservoir with a plurality of frequencies. The fluid reservoir may be a reservoir bound by the engineered fluid-impermeable walls or by naturally formed fluid-impermeable walls or by the distance of the electromagnetic energy emitted from the sensor region to probe the fluid. Further, the different frequencies may be used to probe a fluid sample at different depths. In certain embodiments, an integrated circuit memory chip may be galvanically coupled to the resonant sensor. The integrated circuit memory chip may contain different types of information. Non-limiting examples of such information in the memory of the integrated circuit chip include calibration coefficients for the sensor, sensor lot number, production date, and/or end-user information. In another embodiment, the resonant sensor may comprise an interdigital structure that has a fluid-sensing region.

In certain embodiments, when an integrated circuit memory chip may be galvanically coupled to the resonant sensor, readings of the sensor response may be performed with a sensor reader that contains circuitry operable to read the analog portion of the sensor. The analog portion of the sensor may include resonant impedance. The digital portion of the sensor may include information from the integrated circuit memory chip.

FIG. 3 illustrates a non-limiting example of a design of the resonant sensor 1714. A sensing electrode structure 1834 of the sensor may be connected to the tuning circuits and the data acquisition circuitry 1716. The sensing electrode structure 1834 can be bare and in direct contact with the fluid. Alternatively, the sensing electrode structure can be coated with a protective or sensing coating 1836. The sensing electrode structure, without or with the protective or sensing coating, forms a sensing region 1838. The coating may be applied conformably, and may be a dielectric material. The sensing electrode structure, without or with the protective coating that forms the sensing region, may operationally contact a fluid. The fluid contains the analyte or contaminant (s). The sensing electrode structure may be either without (bare) or with a protective coating. A bare sensing electrode structure may generate an electric field between the electrodes that interacts directly with the fluid. A dielectric protective coated sensing electrode structure may generate an electric field that is between the electrodes that interacts with the fluid after penetrating through the dielectric protective coating. In one embodiment, the coating may be applied onto electrodes to form a conformal protective layer having the same thickness over all electrode surfaces and between electrodes on the substrate. Where a coating has been applied onto electrodes to form a protective layer, it may have a generally constant or variable final thickness over the substrate and sensor electrodes on the substrate. In another embodiment, a substrate simultaneously serves as a protective layer when the electrodes are separated from the fluid by the substrate. In this scenario, a substrate has electrodes on one side that do not directly contact the fluid, and the other side of the substrate does not have electrodes that face the fluid. Detection of the fluid may be performed when the electric field from the electrodes penetrates the substrate and into the fluid. Suitable examples of such substrate materials may include ceramic, aluminum oxide, zirconium oxide, and others.

Figure 4:
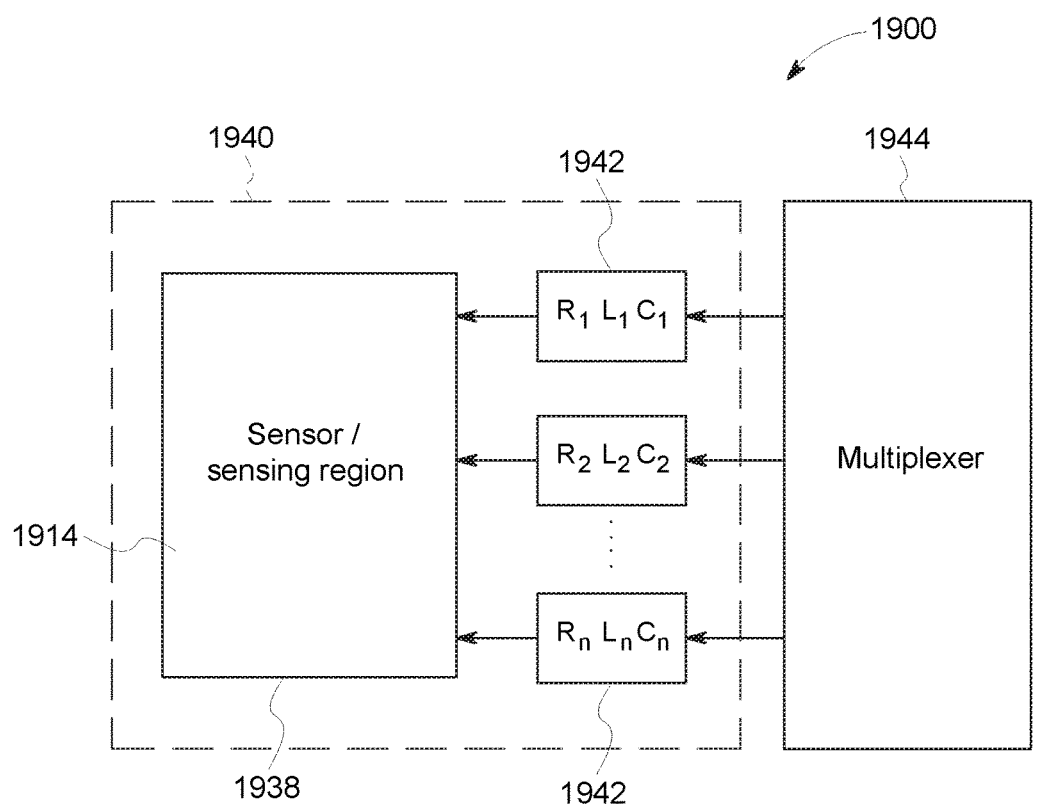
FIG. 4 is a schematic view of a portion of an example sensor system employing a sensor assembly configured for sensing of a fluid using a plurality of frequencies, in accordance with embodiments of the present disclosure.

FIG. 4 illustrates a portion of a resonant sensor system 1900 having a single sensing region 1938, and employed in a sensor assembly 1940 useful to probe a fluid sample using a plurality of frequencies. The sensing region may be disposed on a substrate and may include a suitable sensing material. In some embodiments, the substrate of the sensor may be a dielectric substrate. In some embodiments, the sensor assembly may include a plurality of tuning elements 1942. The plurality of tuning elements may be operatively coupled to the single sensing region to define a plurality of resonant circuits. The tuning elements along with the single sensing region may define a plurality of resonant circuits. Each resonant circuit of the plurality of resonant circuits may include one or more tuning elements of the plurality of tuning elements. Not shown is a semi-permeable film, semi-permeable membrane, or semi-permeable inorganic barrier (collectively a "selective barrier") that allows (or prevents) selective analytes or contaminants through the selective barrier and into the sensing region.

Suitable interdigital electrode structures for probing a fluid sample include two- and four-electrode structures. Suitable materials for electrodes include stainless steel, platinum, gold, noble metals, and others. Suitable materials of a substrate and/or a dielectric protective layer may include silicon dioxide, silicon nitride, parylene, silicone, fluorinated polymers, alumina, ceramics, and others. Suitable examples of sensing layers include semiconducting materials, metal oxides, nanocomposites, polymers, or the like. Suitable electrodes may be formed using metal etching, screen-printing, ink-jet-printing, and mask-based metal deposition techniques. The thickness of fabricated electrodes on the substrates may be in a range of from about 10 nanometers to about 1000 micrometers. The materials for the interdigital electrode structures, substrate, dielectric protective layer, sensing layer, and electrode formation methods may be selected based at least in part on the application specific parameters.

As shown in the illustrated embodiment, the plurality of tuning elements may be disposed external to the sensor. However, in one embodiment, the tuning elements may be disposed on the substrate of the sensor. In another embodiment, some of the plurality of tuning elements may be external to the sensor substrate, while other tuning elements may be disposed on the substrate. The tuning elements may comprise a resistor, a capacitor, an inductor, a resonator, impedance transformer, or combinations thereof.

The sensor assembly 1940 may include a controller that has a multiplexer 1944. The multiplexer may facilitate electronic switching between the tuning elements. The multiplexer may select one or more signals associated with the probing frequencies and forward the selected signal to an output device or a sensor reader. The multiplexer may send a plurality of signals simultaneously to a sensor reader.

During operation, each resonant circuit may resonate at a defined frequency. At least one resonant circuit may resonate at a frequency that may be different from the resonating frequency of the other resonant circuits. By way of example, if the sensing region includes a pair of electrodes, the tuning elements may be a resistor, a capacitor, and an inductor to form an inductor-capacitor-resistor (LCR) resonant circuit. The tuning elements may be electrically coupled to the sensing region. In one embodiment, the tuning elements may be in parallel connection to the sensing region. In certain embodiments, the different resonant circuits of the plurality of resonant circuits may be configured to resonate at different frequencies. The different resonant circuits may be configured to probe the fluid sample with a plurality of resonant frequencies. The different resonant frequencies may be used to probe a fluid sample over the frequency range of spectral dispersions of fluid components. The spectral dispersions of fluid components may include spectral dispersions of external contaminants and/or acidic components of the fluid. The spectral dispersions that may be monitored with the sensors of the present disclosure may be over a frequency range of from about 0.1 Hz to about 100 GHz and include alpha, beta, gamma, delta, and other types of spectral dispersions as constrained by application specific parameters.

Figure 5:
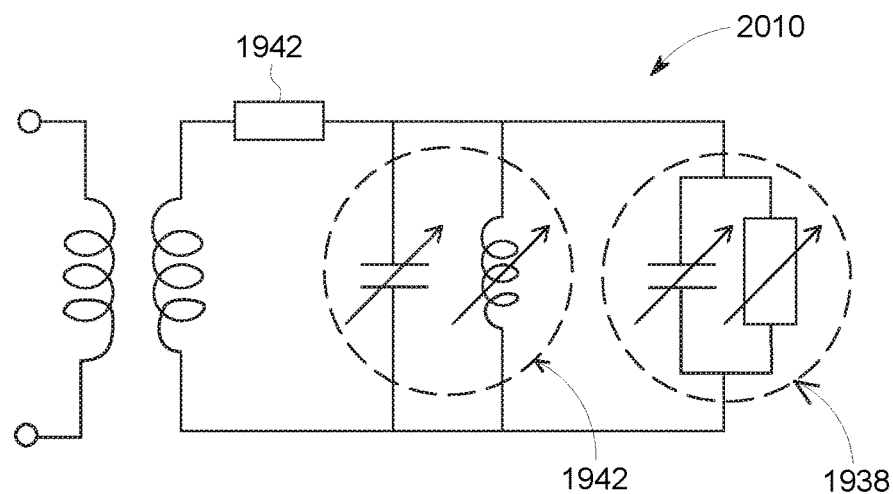
FIG. 5 is an example of an equivalent circuit of the resonant sensor according to an embodiment of the disclosure.

FIG. 5 illustrates another sensor circuit 2010. The sensing region 1938 (shown with variable resistor and capacitor) is combined with tuning components 1942 (shown with variable inductor and capacitor). To realize sensor response at a different frequency range, additional circuit elements may be utilized to tune the frequency range. Therefore, a sensor can be operating at multiple frequency ranges by using a defined or selected combination of extra circuit components—such as inductors, capacitors, and impedance transformers. These components may be connected in parallel or in series, as needed, to the sensor to vary the operating frequency range. The controller may control the impedance transformer ratio to affect the sensitivity. A sensor's frequency response and its magnitude may be based at least in part on the overall input resonant impedance changes due to the sensor's response to the fluid status, fluid behavior, and the like. Thus, the sensor's sensitivity may be controlled through the dynamic tunability of the transformer ratio. Tuning the response of each channel may be achieved, for example, by using one or more inductors. In one embodiment, wireless readout from the electrodes may provide an improvement in response selectivity and sensitivity. In one embodiment, transformer based coupling may reject parasitic LCR components from instrumentation (analyzer, cables, amongst others). The LCR resonator in FIG. 5 has a relatively simple design as compared to other resonators, for example as compared to marginal oscillators that require complicated multi-component circuits for their operation that include a current feedback amplifier and other components.

Figure 6:
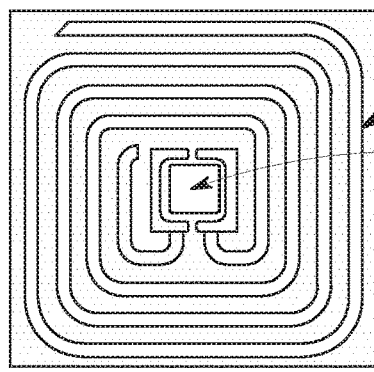
FIG. 6 is an example of an adapted radio frequency identification (RFID) tag for resonant sensing in which the sensing region constitutes a whole or a portion of the resonant antenna according to an embodiment of the disclosure.
Figure 7:
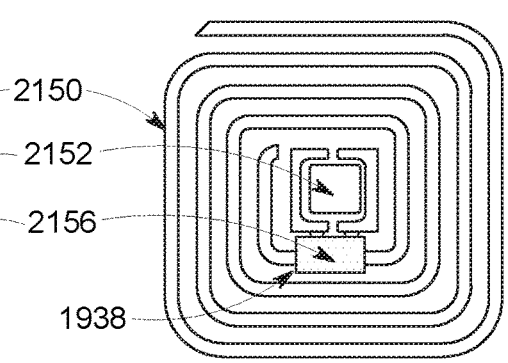
FIG. 7 is an example of an adapted RFID tag for resonant sensing in which the sensing region is in galvanic contact with the antenna and memory chip according to an embodiment of the disclosure.

As noted herein, a suitable wireless sensor may be radio-frequency identification (RFID) sensor where a passive RFID tag may be adapted to perform a sensing function. With reference to FIGS. 6 and 7, an embodiment is shown in which the resonant sensor may be an adapted RFID tag. In FIG. 6, a resonant antenna 2150 and memory chip 2152 may be coated with a protective material or sensing material 2156. The sensing material may be a sensing region of the RFID tag. In FIG. 7, the sensing region 1938 (that can optionally include the protective or sensing material) may be attached across an antenna. In both cases (e.g., both FIGS. 6 and 7), the electrical response of the sensing region may be translated into changes in the resonant impedance response of the sensor. An RFID sensor having a memory chip may operate with a frequency determined at least in part by the operating frequency used the memory chip. That is, some operating frequencies (of the sensor and the chip) may interfere with each other and may be less desirable to have disruptive harmonics or destructive waveforms. And, the sensor can have a circular, square, cylindrical, rectangular, or other appropriately-shaped sensing region and/or antenna.

The resonant frequency of an antenna circuit may be set to a higher frequency than a resonant frequency of the sensor circuit. The frequency differential may be in a range of from, for example, as much as about 4 times to about 1000 times higher. In one embodiment, the sensor circuit may have a resonant frequency that may respond to a determined sensed environmental condition. The two resonant circuits may be connected so that when alternating current (AC) energy is received by the antenna resonant circuit, it may apply direct current energy to the sensor resonant circuit. The AC energy may be supplied through the use of a diode and a capacitor, and the AC energy may be transmitted to the sensor resonant circuit through an LC tank circuit through either a tap within the L of the LC tank circuit or a tap within the C of the LC tank circuit. Further, the two resonant circuits may be coupled such that voltage from the sensor resonant circuit may change the impedance of the antenna resonant circuit. The modulation of the impedance of the antenna circuit may be accomplished through the use of a transistor, for example a FET (field-effect transistor).

The RFID sensor's memory chip may be optional. The RFID sensor without a memory chip can be a resonant LCR sensor and can operate at different frequency ranges from a kilohertz to several gigahertz. That is, the memory chip's absence may widen the available frequency range.

Suitable sensing materials and sensing films as disclosed herein may include materials deposited onto the sensor to perform a function of predictably and reproducibly affecting the resonant impedance sensor response upon interaction with the environment. For example, a conducting polymer, such as polyaniline, changes its conductivity upon exposure to solutions of different pH. That is, the resonant impedance sensor response changes as a function of pH when such a conducting polymer film is deposited onto the RFID sensor surface. Thus, such an RFID sensor works as a pH sensor.

As an example of gaseous fluid detection, when such a polyaniline film is deposited onto the RFID sensor for detection in gas phase, the resonant impedance sensor response also changes upon exposure to basic (for example, $NH_3$) or acidic (for example, HCl) gases. Suitable sensor films include polymer, organic, inorganic, biological, composite, and nano-composite films that change their electrical and or dielectric property based on the environment in which they may be placed. Other examples of sensor films may be a sulfonated polymer such as commercially available Nafion, an adhesive polymer such as silicone adhesive, an inorganic film such as sol-gel film, a composite film such as carbon black-polyisobutylene film, a nano-composite film such as carbon nanotube-Nafion film, gold nanoparticle-polymer film, metal nanoparticle-polymer film, zeolites, metal-organic frameworks, cage compounds, clathrates, inclusion compounds, semiconducting materials, metal oxides, electrospun polymer nanofibers, electrospun inorganic nanofibers, electrospun composite nanofibers, and other sensor materials selected based on application specific parameters. To reduce or prevent the material in the sensor film from leaking into the liquid environment, the sensor materials may be attached to the sensor surface using standard techniques, such as covalent bonding, electrostatic bonding and other techniques. Some sensing materials may require a certain temperature for efficient operation. A non-limiting range of operating temperatures of the sensing materials and associated sensors onto which the sensing materials are deposited is between −260 degrees Celsius and 1600 degrees Celsius.

In one embodiment, the system may measure a resonant impedance (f) (represented by Eq. (1)) of the sensor.

$$(f)=Z_{re}(f)+jZ_{im}(f) \qquad \text{Eq. (1)}$$

where $Z_{re}(f)$ may be the real part of the resonant impedance and $Z_{im}(f)$ may be an imaginary part of the resonant impedance. In one embodiment, the resonant impedance spectral response of the sensor may be a multivariable resonant response as more than one frequency may be utilized to measure sensor response across the resonance of the sensor. In some embodiments, the resonant impedance response of the sensor may be a multivariable resonant response because more than one frequency may be utilized to measure sensor response outside the resonance peak of the sensor. In some embodiments, the sensor response may be measured at multiple frequencies across the resonance of the sensor. For example, if the sensor resonates at about 1 MHz, the measured frequencies and associated sensor responses may be measured from about 0.25 MHz to about 2 MHz. This multivariable resonant response may be analyzed by multivariate analysis. The multivariable response of the sensor includes the sensor's full resonant impedance spectral response and/or several individually measured parameters, such as but not limited to $F_p$, $Z_p$, $F_z$, $F_1$, $F_2$, $Z_1$, and $Z_2$. As used herein, the term "resonant impedance spectral response" may be referred to as "impedance response," "multivariable resonant response," "resonant impedance spectra," and/or variations thereof.

Figure 8:
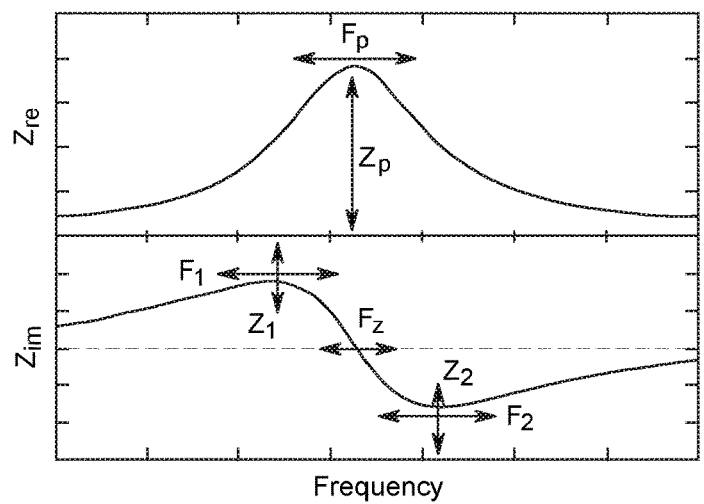
FIG. 8 is a graph of measured resonant impedance parameters of an embodiment of the resonant sensor, in accordance with embodiments of the present technique.

FIG. 8 depicts a graph of measured resonant impedance parameters of an embodiment of the resonant sensor, in accordance with embodiments of the present technique. The properties include the frequency of the maximum of the real part of the resonant impedance ($F_p$, resonance peak position), magnitude of the real part of the resonant impedance ($Z_p$, peak height), zero-reactance frequency ($F_z$, frequency at which the imaginary portion of resonant impedance may be zero), resonant frequency of the imaginary part of the resonant impedance ($F_1$), and anti-resonant frequency of the imaginary part of the resonant impedance ($F_2$), signal magnitude ($Z_1$) at the resonant frequency of the imaginary part of the resonant impedance ($F_1$), and signal magnitude ($Z_2$) at the anti-resonant frequency of the imaginary part of the resonant impedance ($F_2$). Other parameters may be measured using the entire resonant impedance spectra, for example, quality factor of resonance, phase angle, and magnitude of resonant impedance.

Figure 9:
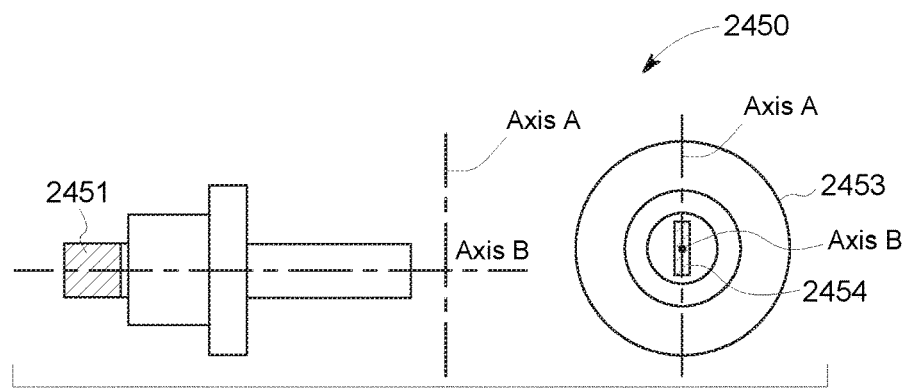
FIG. 9 is an example of a resonant sensor in which the sensing region is arranged parallel to the sensor axis insertion into the measured fluid, and therefore, perpendicular to the insertion port of the sensor according to an embodiment of the disclosure.
Figure 10:
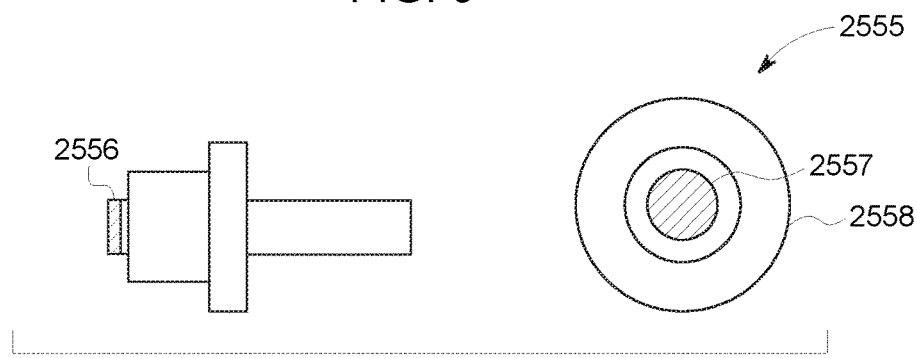
FIG. 10 is an example of a resonant sensor in which the sensing region is arranged perpendicular to the sensor axis insertion into the measured fluid, and therefore, parallel to the insertion port of the sensor according to an embodiment of the disclosure.

For measurements of fluid properties in fluid reservoirs, sensors with their sensing regions can be designed to fit standard ports or specially made ports in the reservoirs. Suitable design examples are depicted in FIG. 9 and FIG. 10. An example is provided of a resonant sensor 2450 with an aligned sensing region 2451. The sensing region defines a first Axis A, which is perpendicular to a transverse axis labeled Axis B. An insertion port structure 2453 defines an insertion aperture 2454 that is elongated along Axis A. The sensing region, then, is arranged parallel to the port's elongated aperture, translation along Axis B allows for sensor region insertion into the port and to contact a measured fluid. An example of another resonant sensor 2555 in which the sensing region 2556 is not constrained by its shape relative to an aperture 2557 defined by a port structure 2558 is depicted in FIG. 10. Alignment pins, not shown, may be used to align the sensor, and the sensing region, relative to the port aperture, as may be desired.

Figure 11:
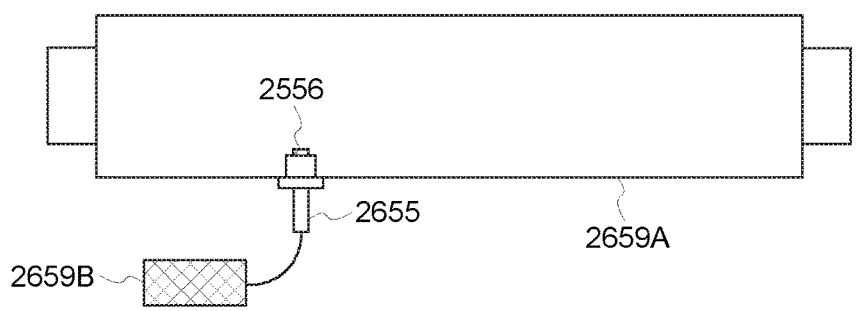
FIG. 11 is an example of sensing of fluid properties with a sensor in a fluid reservoir when the sensor is incorporated into the reservoir with the sensing region of the sensor exposed to the fluid and the sensor reader located near the sensor and connected to the sensor with a cable according to an embodiment of the disclosure.
Figure 12:
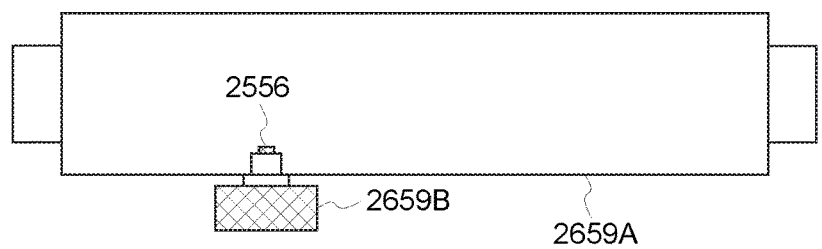
FIG. 12 is an example of sensing of fluid properties with a sensor in a fluid reservoir when the sensor is incorporated into the reservoir with the sensing region of the sensor exposed to the fluid and the sensor reader directly connected to the sensor according to an embodiment of the disclosure.

Measurements of fluid properties in fluid reservoirs may be performed using sensors with their sensing regions exposed to the fluid as shown in FIGS. 11 and 12. The sensor 2655 shown in FIG. 11 is installed in a fluid transfer pipe 2659A, and is coupled to a sensor reader 2659B. The sensor reader 2659B may be coupled by wire or cable, and located proximate to the sensor 2655 as shown in FIG. 11. In another embodiment, the sensor reader 2659B may be directly connected to the sensor without a cable—as shown in FIG. 12. During operation, a fluid flows through the pipe and contacts the sensing region 2556. As the sensing region 2556 senses an analyte of interest it signals the sensor reader 2659B.

Figures 13A, 13B, 13C:
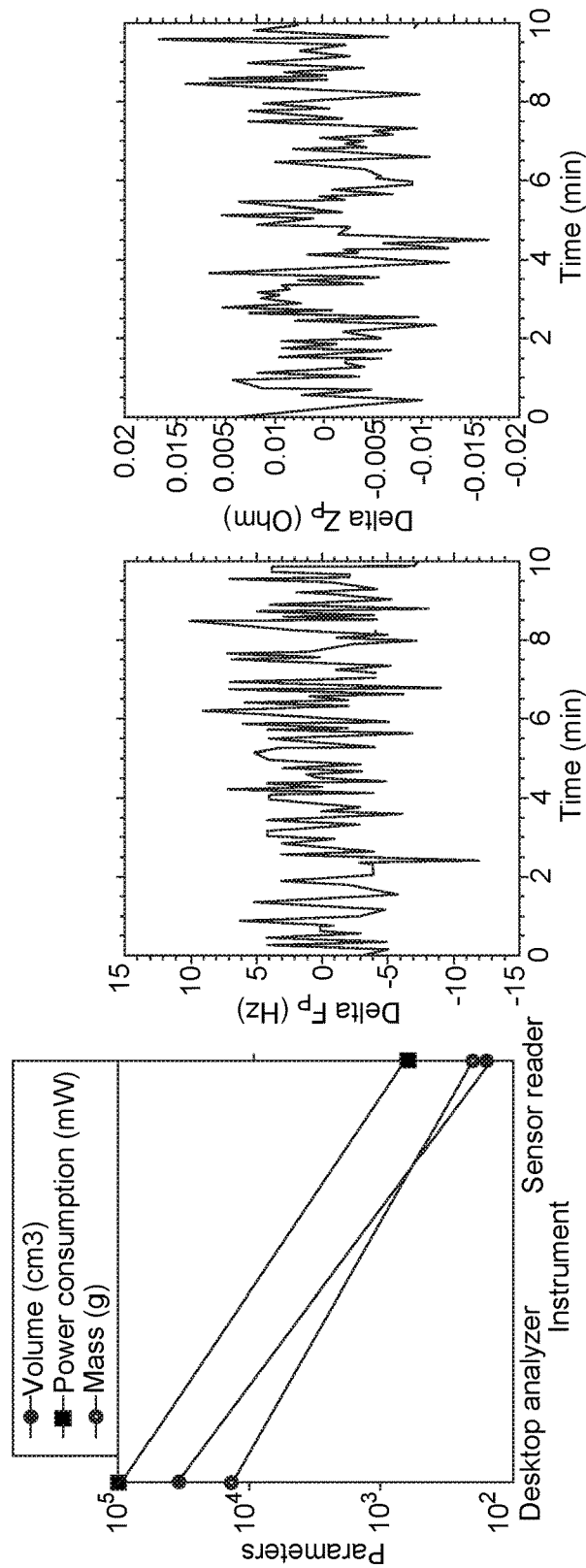
FIGS. 13A-C are graphs depicting measurements related to the sensor reader according to one embodiment.

The sensor reader (also referred to as micro-analyzer) has been developed with a small form factor, low power consumption and low cost of components. FIGS. 13A-C are graphs depicting measurements related to the sensor reader according to one embodiment. FIG. 13A is a comparison of power consumption, size, and weight between a desktop analyzer and the developed micro-analyzer. FIG. 13A depicts that the design of the micro-analyzer provided 100-500-fold reduction in power consumption, size, and weight as compared to desktop analyzers. These advancements make the sensor reader attractive for a wide range of applications including monitoring of industrial fluids, where laboratory analyzers are size-, power-, and cost-prohibitive. FIGS. 13B and 13C depict measured Fp and Zp noise levels of the developed micro-analyzer, respectively. The developed sensor reader has a 1σ Fp noise of 5 Hz and 1σ Zp noise of 0.006 ohm. This electronic design of the sensor reader provided 4-14 times reduction in noise levels in measurements of (f) spectra as compared to measurements with a laboratory desktop analyzer with Fp noise=60 Hz and Zp noise=0.025 Ohm.

Figure 14:
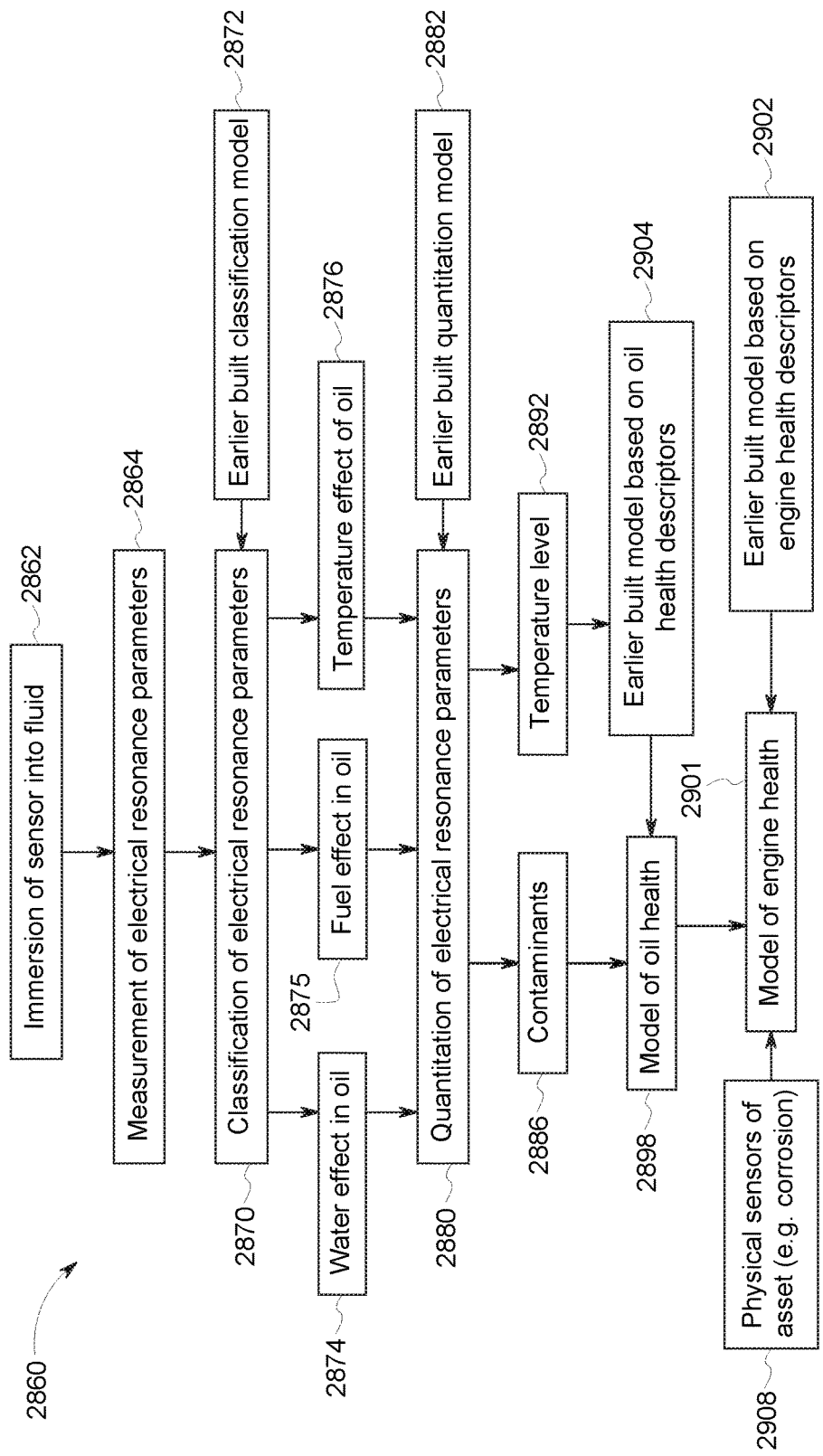
FIG. 14 is a flow diagram of fluid assessment according to an embodiment of the disclosure.

A flow diagram of a method 2860 is shown in FIG. 14. In one embodiment, a method for monitoring of oil health includes immersion of the sensor into an oil (step 2862) and measurement of electrical resonance parameters of the resonance spectra (step 2864) at several resonances of a single sensor. For quantitation of contamination of engine oil by water, fuel leaks, and soot with a sensor, the sensor may be placed into operational contact with the fluid at step 2862. In a specific embodiment, the resonant impedance spectra $(f)=Z_{re}(f)+jZ_{im}(f)$ of a sensor may be determined at step 2864. For example, the parameters from the measured (f) spectra such as the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_z$ of $Z_{im}(f)$, may be calculated. In another embodiment, the electrical resonance parameters may include capacitance parameters of the sensor in operational contact with the fluid, instead or in addition to impedance parameters.

The method 2860 classifies the electrical resonance parameters at step 2870. This may be done using a determined classification model 2872 to assess, for example, one or more of water effects 2874, fuel effects 2875, and temperature effects 2876. Quantitation of the electrical resonance parameters may be performed at step 2880 by using a predetermined, earlier saved quantitation model 2882, and determination of components 2886 in oil such as water, fuel, soot, and wear metal particles 2890 as well as the temperature 2892, and prediction of the oil health 2898 and the engine health 2901. This may be done by using one or more of determined engine health descriptors 2902 and oil health descriptors 2904 as well as inputs from any additional sensors 2908. Suitable additional sensors may include those sensing corrosion, temperature, pressure, system (engine) load, system location (e.g., by GPS signal), equipment age calculator, pH, and the like.

For example, in one embodiment, a sensor system may be an electrical resonator that may be excited with a wired or wireless excitation and where a resonance spectrum may be collected and analyzed to extract at least four parameters that may be further processed upon auto scaling or mean centering of the parameters and to quantitatively determine properties of the oil. The properties of the oil that are determined via analyzing the resonance impedance spectrum may include the concentration of water, acid, and/or fuel in engine oil, and the properties may be used to predict the remaining life of the engine oil and/or the remaining life of the engine in which the oil is disposed. The spectral parameters of the resonance spectrum such as $F_p$, $Z_p$, $F_z$, $F_1$, $F_2$, $Z_1$, and $Z_2$ or the whole resonance spectrum with a single or multiple resonators can be used for data processing.

The classification model 2872 may be built using the predicted contributions of the spectral parameters for an uncontaminated fluid and for fluid contamination using previously determined component effects and their corresponding spectral parameters. Such effects may be quantified using the quantitation model 2882 to predict if a measured or sensed fluid has any water effects, fuel leak effects, or temperature effects. That is, based on previously or empirically determined effects of components on a particular fluid, the resonance parameters, both real and imaginary, may be changed and/or affected in a quantifiable manner if specific components of interest are present. Further, based on the measured parameters, a concentration of a particular component may also be predicted, and multi-component models may be generated. The disclosed techniques may be used to sense a suitable fluid and to build a component and environmental effect model.

In one embodiment, measurements of impedance parameters of fluids may be performed at two or more temperatures of the fluid. Measurements at different temperatures provide information about species of interest and other species (chemical constituents) in the fluid when measured as the frequency dispersion profiles over the broad frequency range or when measured as frequency responses over the relatively narrow frequency range. Performing analysis of resonant impedance spectra of the sensor collected at different temperatures and determining two or more properties of the fluid per temperature based on the analyzed resonant impedance spectra allows an improvement of the sensor accuracy of determinations of properties of species of interest. This improvement may be due to differences of frequency responses of species of interest and other species in the fluid as a function of temperature caused by the molecular structure of these different species. Measurements at different temperatures may be performed with a resonant sensor that has a thermal element in thermal contact with the sensing region of the resonant sensor. The thermal element produces a local change in temperature of the fluid which may be in proximity to the sensing region. This local temperature change can be above or below the temperature of the bulk of the fluid in the container with the sensor. Non-limiting examples of thermal elements include a Peltier cooler, thin-film heater, and pencil heater. The thermal element can produce a local change in temperature of the fluid in the range from about 1 degree Celsius to about 50 degrees Celsius.

In one embodiment, measurements of parameters of fluids may be performed to determine dynamic signatures of the changes of chemical constituents in the fluid. The time scales of these dynamic signatures may vary greatly. Suitable timescale in a range of from about 1 second to about 200 days may be useful to determine different types of leaks of fluids in engines. Such determinations allow the identification of dynamic signatures of the leaks in an engine, relation of the identified signature with the known leak signature from a specific engine component, and determination of the location of the leak based on the signature.

Measurements of properties of fluids may be performed at extreme temperature conditions. Depending on the application, these conditions may range from temperatures down to about −260 degrees Celsius and to temperatures up to about +1600 degrees Celsius. Such harsh temperature conditions with negative temperature down to about −260 degrees Celsius may be useful in relation to liquefied natural gas (LNG) and in the storage of biological and other types of samples. Harsh temperature conditions with positive temperature of up to about +1600 degrees Celsius may be useful in monitoring equipment where the temperature of operating components of the equipment can reach about +1600 degrees Celsius. Examples of equipment that operates at about 250 degrees Celsius may include downhole equipment in oil and gas production and the operations of an internal combustion engine (diesel, natural gas, hydrogen (direct combustion or fuel cells), gasoline, combinations thereof, and the like) for one or more of the fuel, the lubrication system, and the cooling/radiator system. Another example of such equipment may include an oil-filled transformer. Examples of equipment that operates at about 1000 and up to 1500 degrees Celsius include gas turbines. Examples of equipment that operates at about 1600 degrees Celsius include aircraft jet engines.

The applicability of multivariable electrical resonators may be demonstrated by detection of engine oil contamination from water and diesel fuel and determinations of water in model fluid such as dioxane that has the dielectric constant similar to oil. Determination of resolution of the sensor measurements may be performed using hexane and toluene as model systems. Samples of some engine oil were obtained from GE Transportation, while other chemicals may be commercially obtained from Aldrich.

Measurements of the resonant impedance of sensors may be performed with a network analyzer (Agilent) or a precision impedance analyzer (Agilent), under computer control using LabVIEW. Collected resonant impedance data may be analyzed using KaleidaGraph (Synergy Software, Reading, Pa.) and PLS Toolbox (Eigenvector Research, Inc., Manson, Wash.) operated with Matlab (The Mathworks Inc., Natick, Mass.).

Different amounts of fuel and water leaks into oil may be determined quantitatively and experimentally with a single multivariable resonant sensor. Suitable oil may be railroad internal combustion engine oil. Suitable fuel may be diesel fuel. Binary and ternary mixtures of water and fuel in oil may be produced in different proportions. Concentrations of water may be 0, 0.1% and 0.2% (by volume). Concentrations of fuel may be 0, 3% and 6% (by volume).

Figure 15:
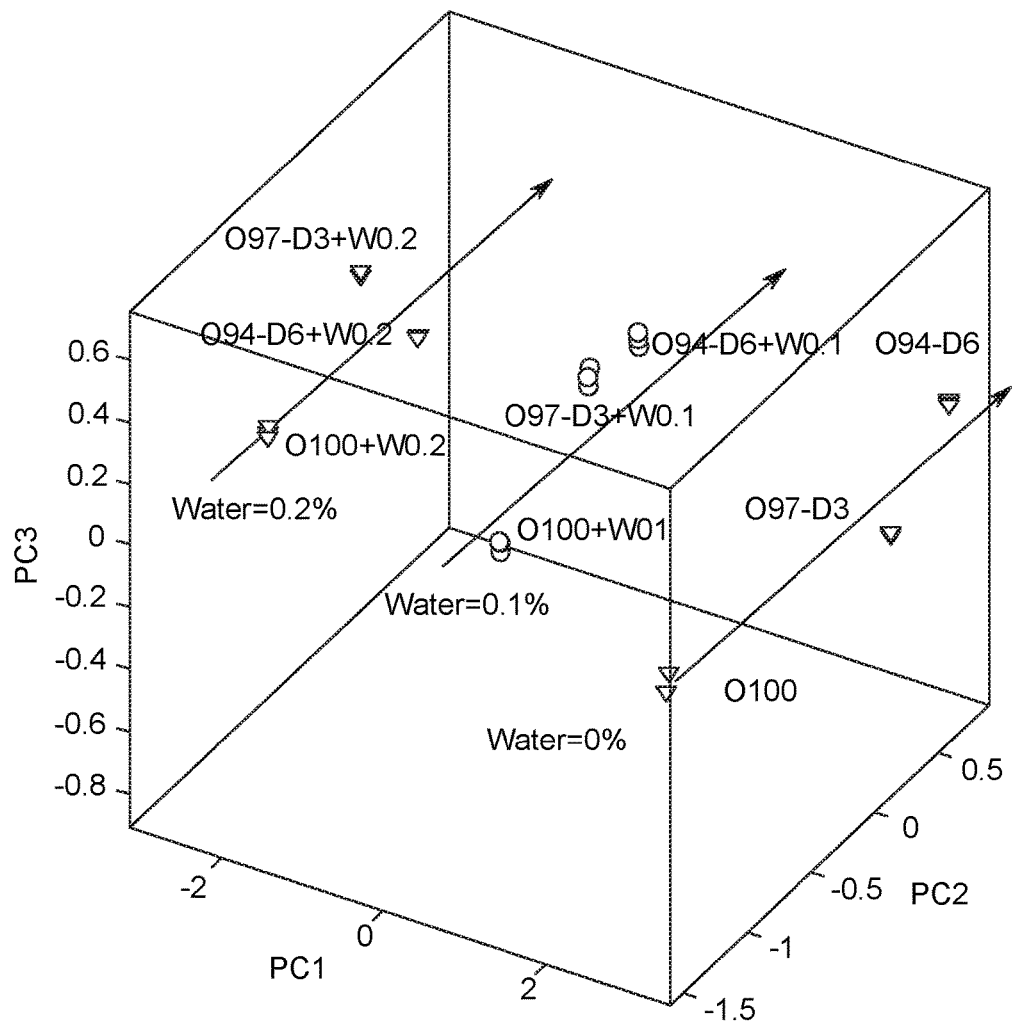
FIG. 15 is a plot of a resonant impedance data for detection of engine oil, water, and fuel with a highlighted water leak.
Figure 16:
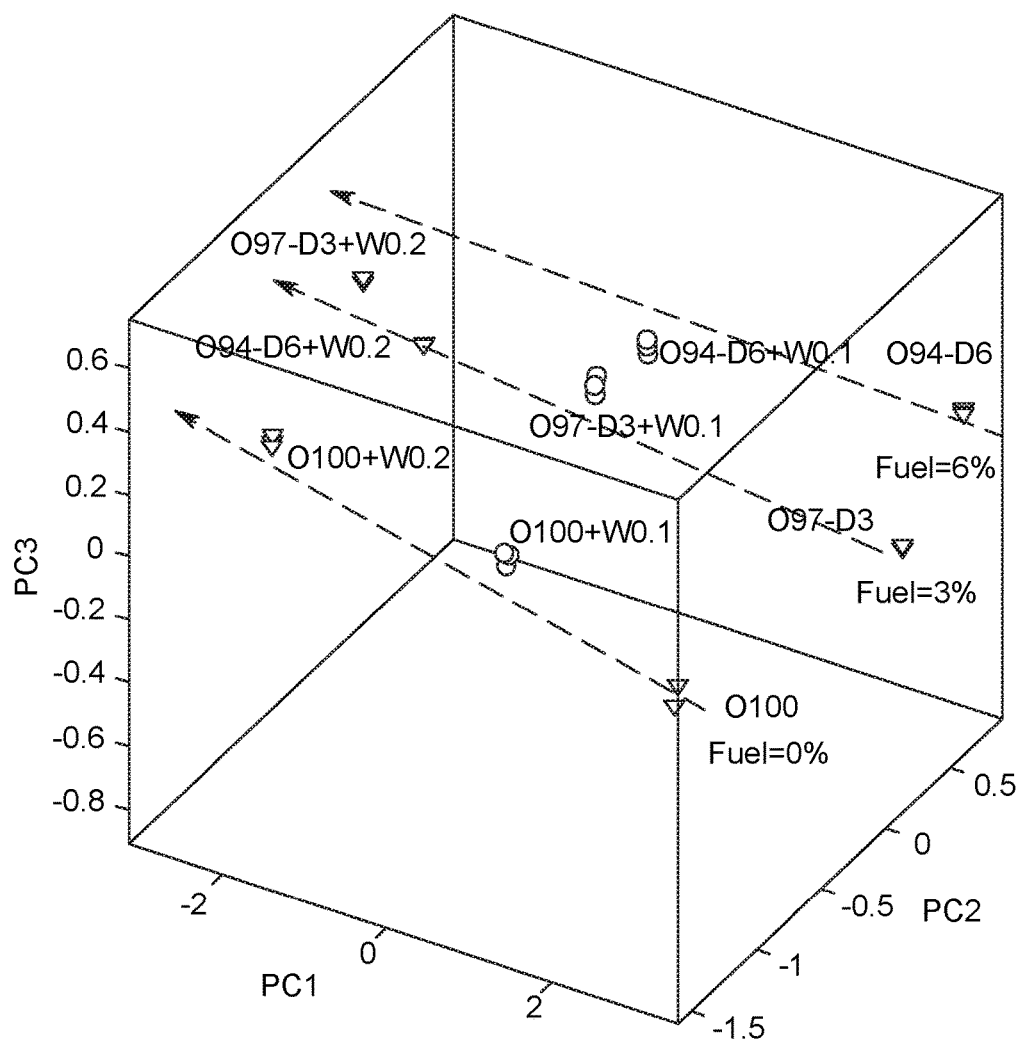
FIG. 16 is a plot of a resonant impedance data for detection of engine oil, water, and fuel with a highlighted fuel leak.

The resonance spectra from measured samples may be processed and the processed data served as inputs to the principal components analysis (PCA) tool. PCA may be a pattern recognition method that explains the variance of the data as the weighted sums of the original variables, known as principal components (PCs). A highlight of detection of water in mixtures of engine oil, water, and fuel may be illustrated in FIG. 15 that depicts a scores plot of a developed PCA model. A highlight of detection of fuel in mixtures of engine oil, water, and fuel may be illustrated in FIG. 16 that depicts a scores plot of a developed PCA model. In FIGS. 15 and 16, concentrations of water of 0.1% and 0.2% are labeled as W0.1 and W0.2, respectively. Concentrations of fuel of 3% and 6% are labeled as D3 and D6, respectively. The multivariable response of the resonant transducers originates from the measured whole resonance spectra of the transducer followed by the processing of these spectra using multivariate analysis tools. For quantitation of contamination of engine oil by water and fuel leaks with a single multivariable sensor, the resonant impedance spectra $(f)=Z_{re}(f)+jZ_{im}(f)$ of the resonant transducer may be measured. Several parameters from the measured (f) spectra may be calculated that included the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_Z$ of $Z_{im}(f)$ as shown in FIG. 8.

By using multivariate analysis of calculated parameters of (f) spectra, classification of analyte may be performed. Suitable analysis techniques for multivariate analysis of spectral data from the multivariable sensors may include Principal Components Analysis (PCA), Independent Component Analysis (ICA), Linear Discriminant Analysis (LDA), and Flexible Discriminant Analysis (FDA). PCA may be used to discriminate between different vapors using the peptide-based sensing material. A loadings plot of the PCA model is illustrated in FIG. 17. This plot illustrates the contributions of individual components from the resonance spectrum. The plot shows that all components such as Fp, F1, F2, Fz, Zp, Z1, and Z2 had contributions to the sensor response.

Figure 18:
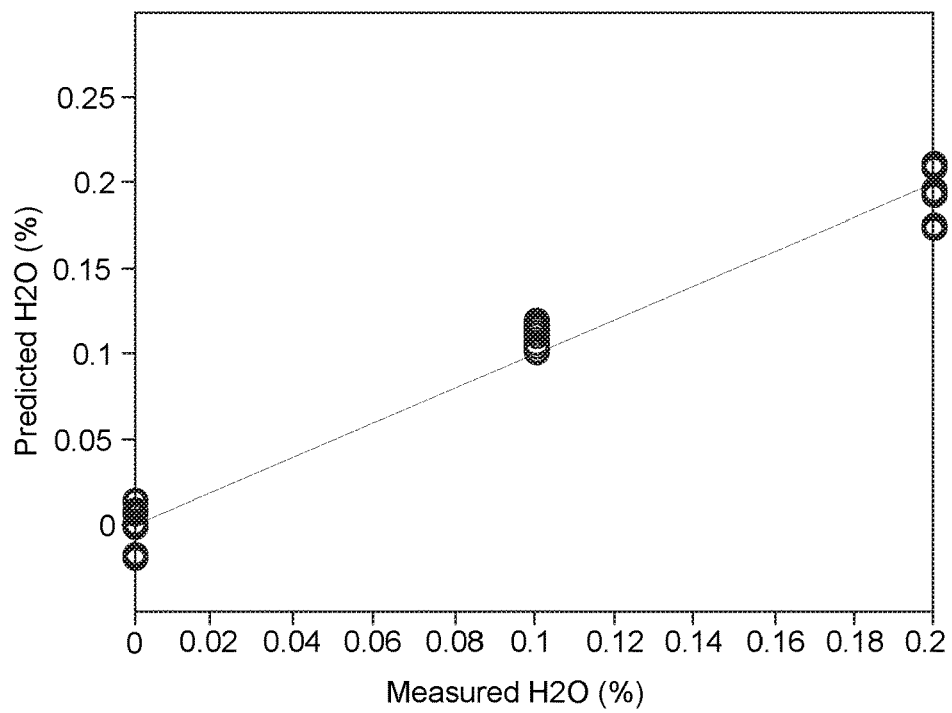
FIG. 18 is a correlation plot between the actual (measured) and predicted concentrations of water in water/fuel/oil mixtures using a single resonant sensor.
Figure 19:
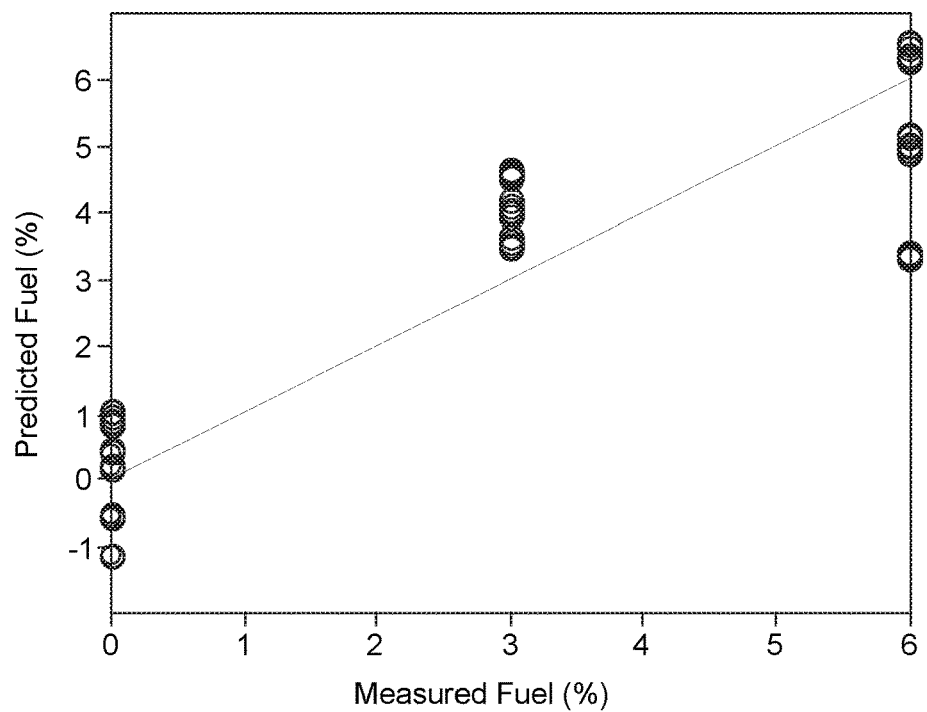
FIG. 19 is a correlation plot between the actual (measured) and predicted concentrations of fuel in water/fuel/oil mixtures using a single resonant sensor.

Quantitation of water and fuel in oil in their binary and ternary mixtures may be further performed with a single multivariable resonant sensor using PLS Toolbox (Eigenvector Research, Inc., Manson, Wash.) operated with Matlab (The Mathworks Inc., Natick, Mass.). FIG. 18 shows a correlation plot between actual (measured) and predicted concentrations of water in water/fuel/oil mixtures using a single resonant sensor. FIG. 19 shows a correlation plot between measured and predicted concentrations of fuel in water/fuel/oil mixtures using a single resonant sensor. Prediction errors of simultaneous quantitation of water and fuel in oil with the single sensor may be 0.02% of water and 1.3% of fuel.

Figure 20:
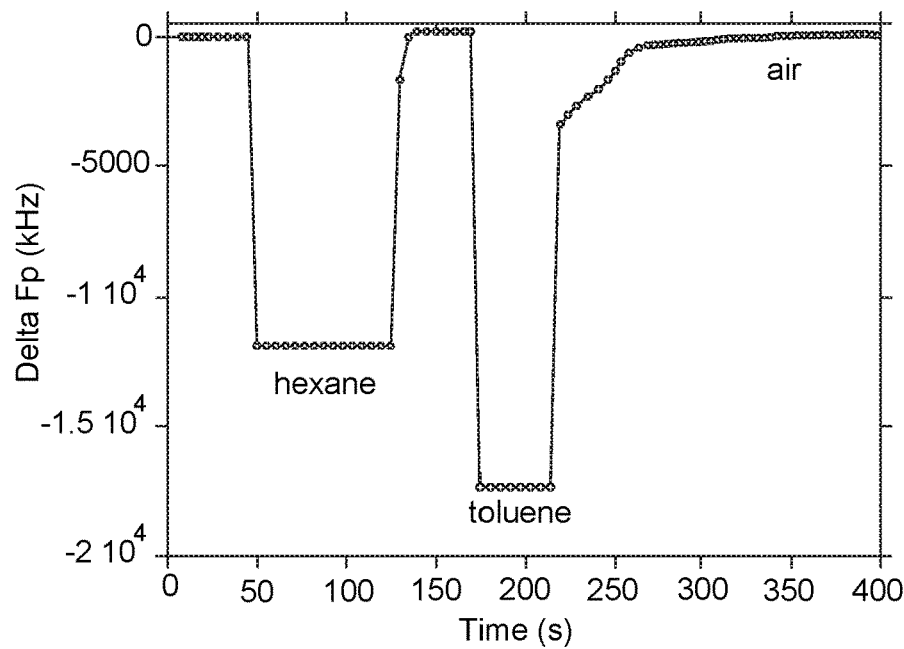
FIG. 20 is a plot of a spectral parameter showing resolution of a resonant sensor to distinguish between hexane and toluene.
Figure 21:
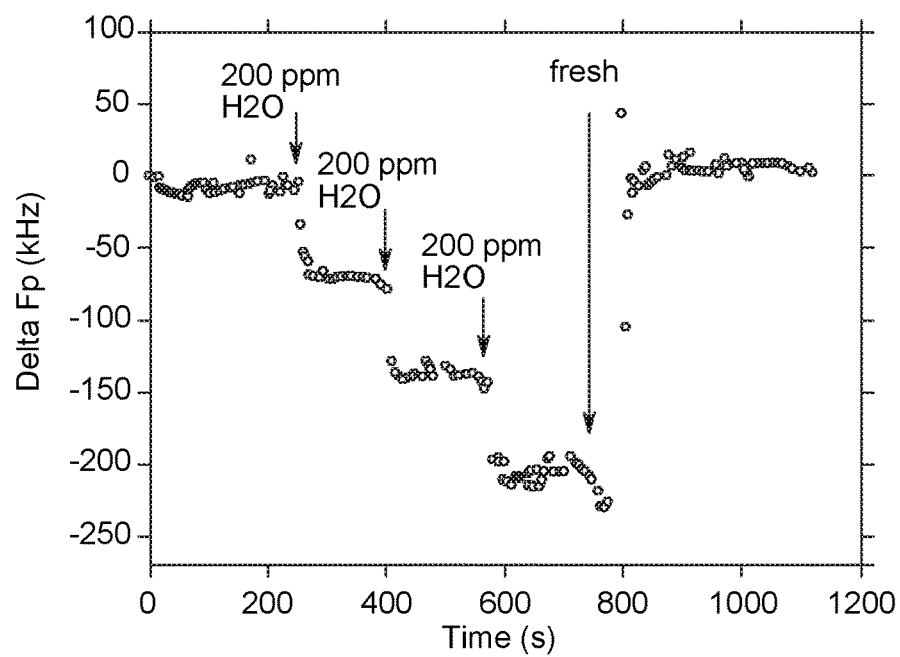
FIG. 21 is a plot of a spectral parameter showing resolution of water addition into dioxane.

In another example, sensor resolution may be determined in multi-part experiments. In a first experiment, hexane and toluene may be used as model chemicals to determine the ability of the sensor to resolve differences in the dielectric constant. Hexane has the dielectric constant of 1.88 while toluene has the dielectric constant of 2.38. A developed sensor may resolve these two liquids with the resolution of the dielectric constant of 0.0004-0.0012. Expected results are shown in FIG. 20. In the second experiment, 1,4-dioxane may be used as a model chemical for oil because the dielectric constant is similar to oil and it is easily miscible with water. The sensor may resolve water additions into dioxane down to 7-20 ppm. Expected results are shown in FIG. 21 illustrating that the developed sensor may be able to resolve water additions into dioxane (model system for oil) down to 7-20 ppm with water additions done in increments of 200 ppm.

Figure 22:
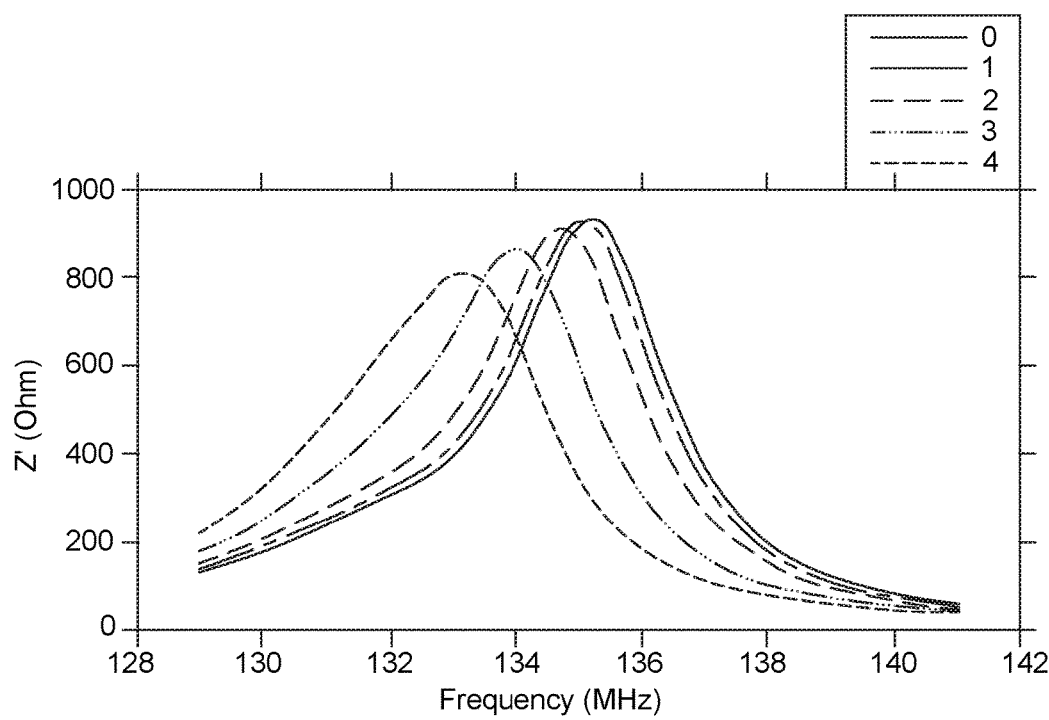
FIG. 22 is a plot of the real part of resonant impedance spectra after soot and water addition.
Figure 23:
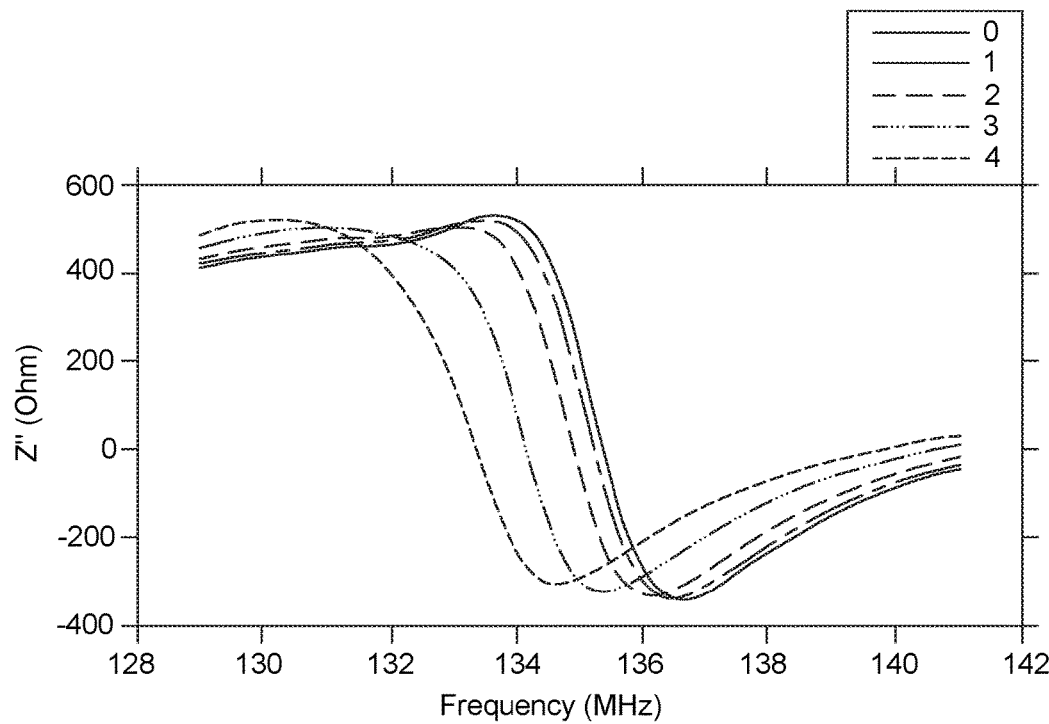
FIG. 23 is a plot of the imaginary part of resonant impedance spectra after soot and water addition.
Figure 24:
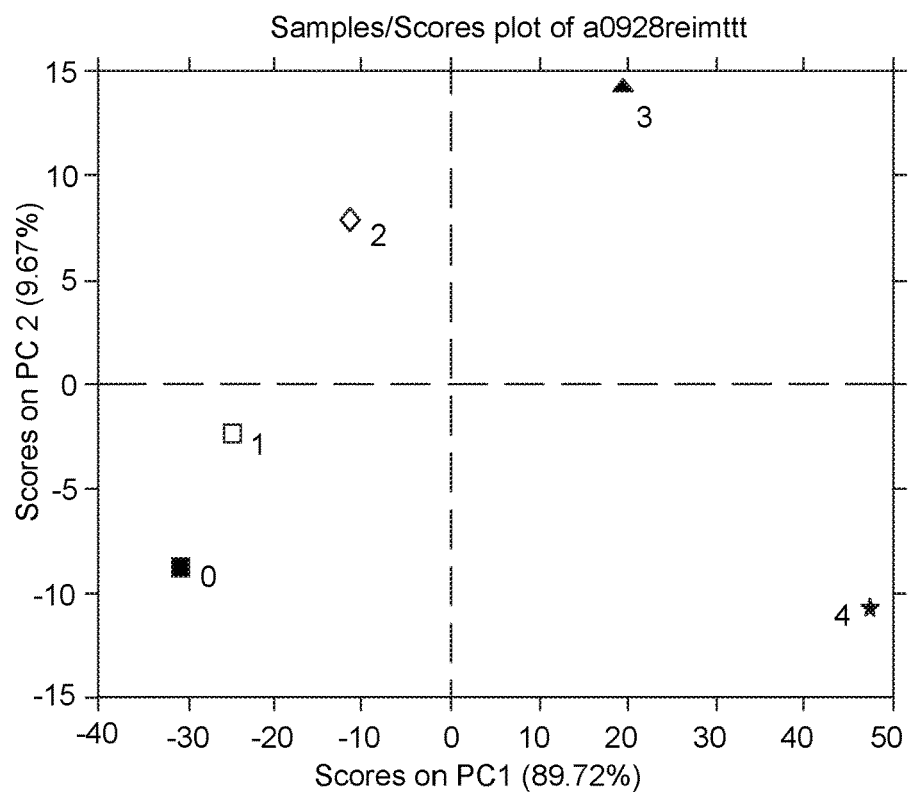
FIG. 24 depicts the PCA scores plot of PC1 vs. PC2 upon exposure of sensor to five solutions and performing resonance impedance measurements.

In another example, water and soot (carbon black) additions may be done to dioxane and measured with a sensor. Water additions may be done as 500 ppm, 1000 ppm, and 2500 ppm additions. Soot (carbon black) may be added as 100 ppm carbon black with 2500 ppm of water. Exemplary resonance spectra of a sensor are presented in FIGS. 22 and 23. Results of multivariate analysis are presented in FIG. 24. FIG. 22 shows the real part $Z_{re(f)}$ and FIG. 23 shows imaginary part $Z_{im(f)}$ of resonant impedance. Measured samples may be: (0) clean model oil (dioxane); (1) addition of 500 ppm of water; (2) addition of 1000 ppm of water, (3) addition of 2500 ppm of water; (4) addition of 2500 ppm of water and 100 ppm of soot (carbon black). FIG. 24 shows a scores plot of Principal component 1 (PC1) vs. Principal component 2 (PC2) illustrating spectral relation between sensor responses to different types of contamination. Samples may be: (0) clean model oil (dioxane); (1) addition of 500 ppm of water; (2) addition of 1000 ppm of water; (3) addition of 2500 ppm of water; (4) addition of 2500 ppm of water and 100 ppm of soot (as carbon black).

Figure 25:
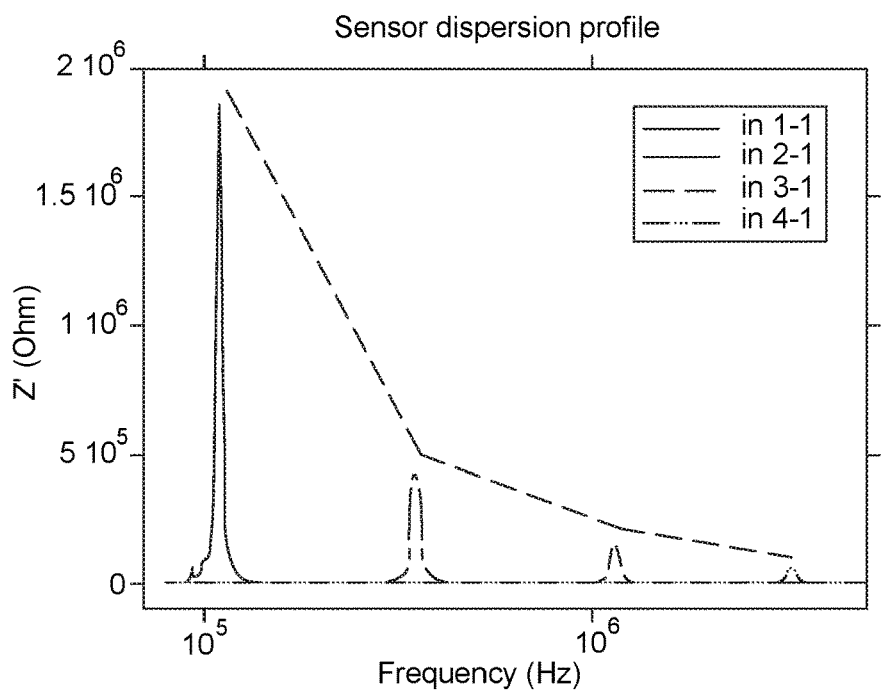
FIG. 25 displays a plot of four resonant spectral profiles from a single sensor for uncontaminated dioxane.
Figure 26:
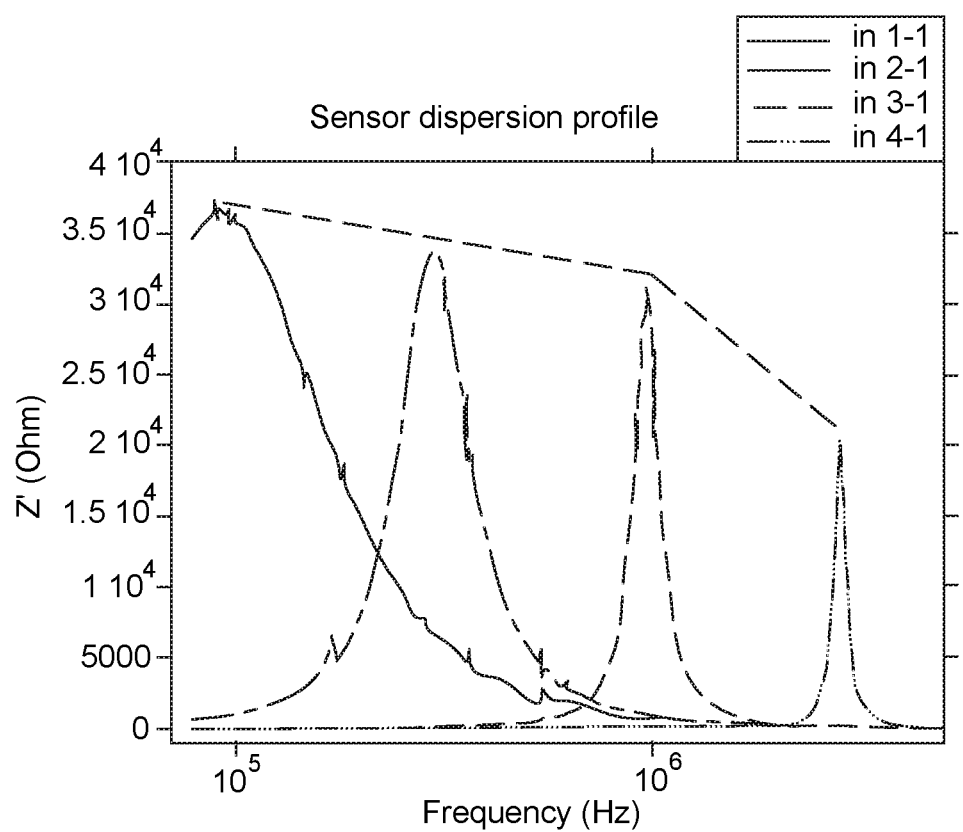
FIG. 26 displays a plot of resonant spectral profiles from a single sensor upon addition of water into the dioxane.

In another example, a multiresonant sensor system may be built with four resonant frequencies. The 1,4-dioxane can be used as a model chemical for oil, because its dielectric constant is somewhat similar to oil and it is miscible with water. Water additions may be done to dioxane and measured with a sensor. Four example resonance spectra of the sensor are presented in FIGS. 25 and 26. These values illustrate that the dispersion profile of the sensor in non-contaminated dioxane (as shown in FIG. 25) has changed its shape upon addition of water (as shown in FIG. 26). Also, the widths and the magnitudes of the resonance peaks have been modified by water addition.

Figure 27:
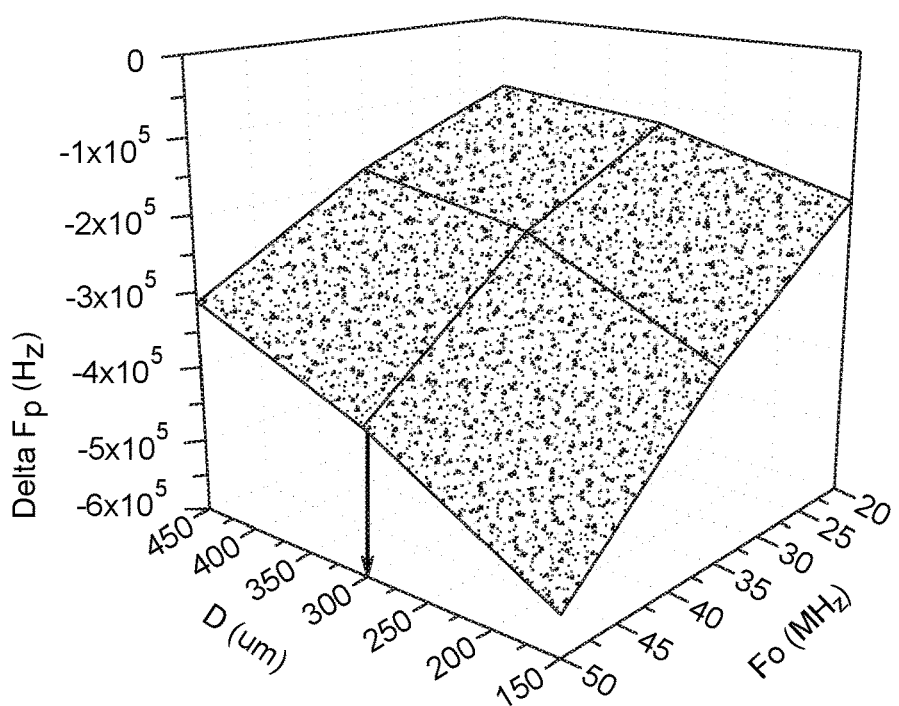
FIG. 27 is plot of effects of sensor design on sensitivity of Fp measurements.
Figure 28:
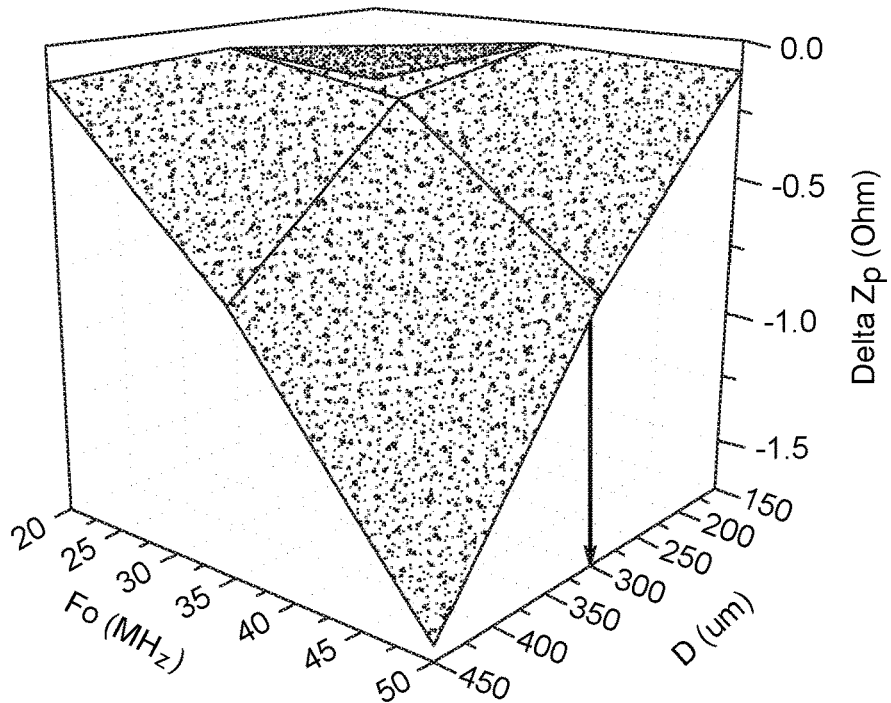
FIG. 28 displays effects of sensor design on sensitivity of Zp measurements.

In another example, sensor electrode geometries and resonant frequency may be optimized for the maximum Fp and Zp responses to water. A two-factor design of experiments may be done by varying interdigital electrode (IDE) spacing D and electrode width W, where D=W=150, 300, 450 micrometers (μm) and varying resonance frequency, Fp, as Fp=20, 35, 50 MHz (in air). Measurements may be performed by adding water to dioxane at 5000 ppm concentration. FIG. 27 shows effects of sensor design on sensitivity of Fp measurements. FIG. 28 shows effects of sensor design on sensitivity of Zp measurements. A 300 μm IDE spacing and 50 MHz operation frequency yielded strong Fp and Zp signals.

Figure 29:
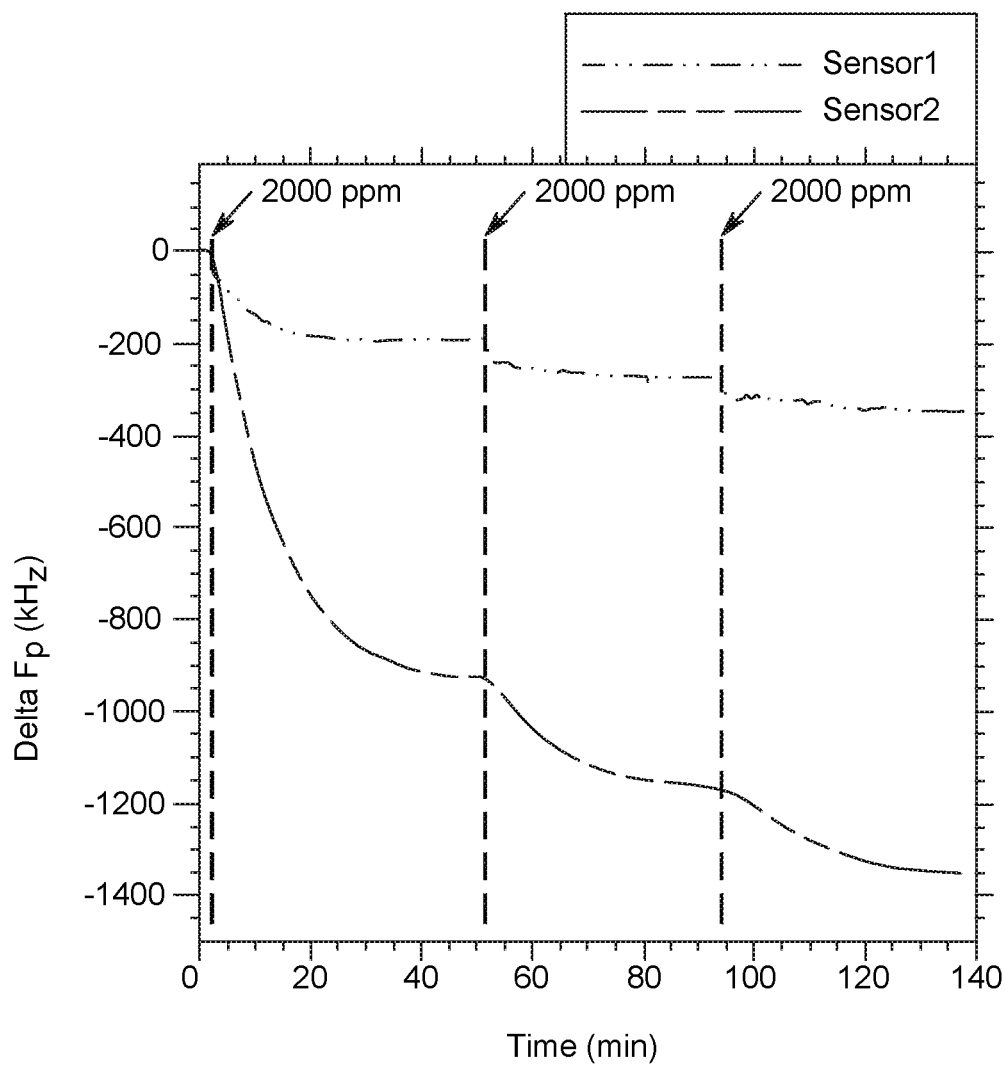
FIG. 29 is plot of results of measurements of water in oil with two multivariable resonant sensors.

In another example shown in FIG. 29, determination of water in oil may be performed by circulating oil in a test loop and adding water at 2000 ppm increments to generate water concentrations in oil of 2000 ppm, 4000 ppm, and 6000 ppm. Measurements may be performed using two resonant sensors. Sensor 1 had area of 2 cm$^2$ with the electrode width/spacing of 0.4 mm/0.4 mm and resonating at 80 MHz in air. Sensor 2 may be one of geometries from the design of experiments and had area of 4 cm$^2$ with the electrode width/spacing of 0.15 mm/0.15 mm and resonating at ~50 MHz in air. The limit of detection of water in oil may be determined at the signal-to-noise level of three to be 3-12 ppm (Sensor 1) and 0.6-2.6 ppm (Sensor 2) based on the measured sensor noise levels and signal levels at 2000 ppm of added water.

Figure 30:
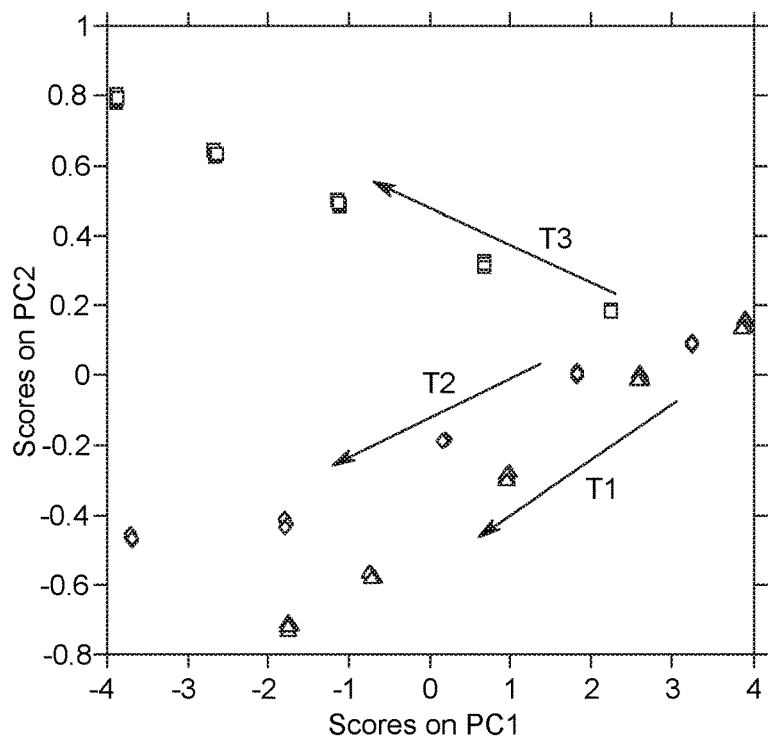
FIG. 30 is a scores plot of a developed PCA model of responses of the resonant sensor to additions of water at different temperatures, showing different response directions.
Figure 31:
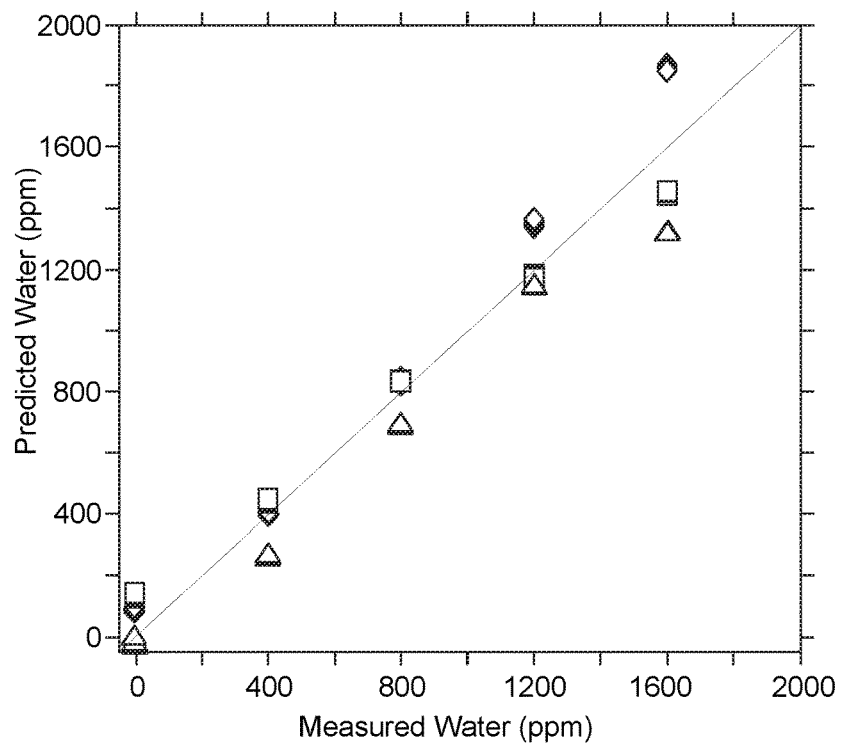
FIG. 31 is plot of results of multivariate linear regression model using partial least squares technique to quantify water concentrations in oil using responses of the single sensor.
Figure 32:
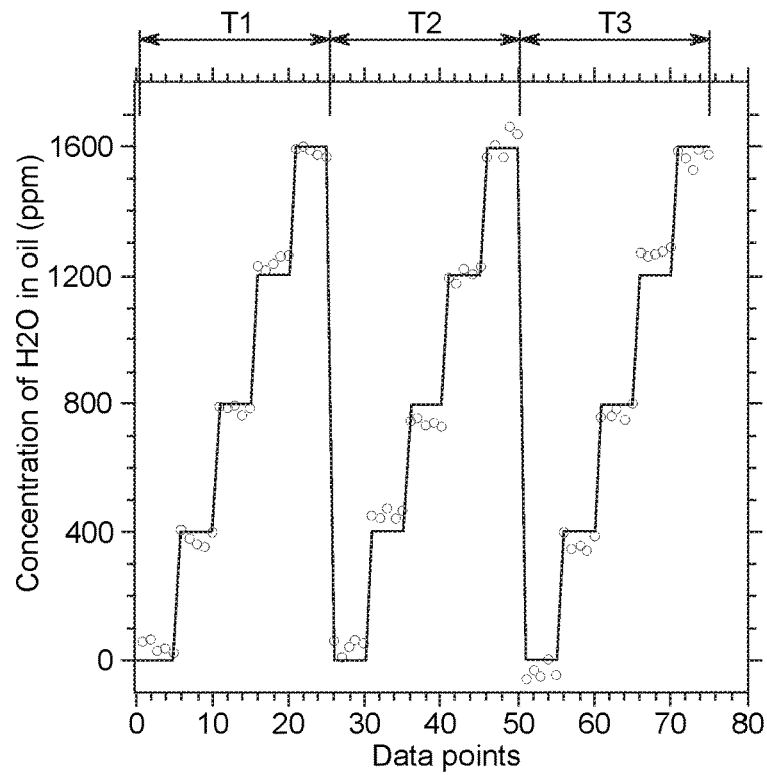
FIG. 32 is a plot of the actual (measured) concentrations of water in oil over time at three temperatures (solid line) and predicted concentrations (open circles).

In another example, determination of water in oil at different oil temperatures may be performed by circulating oil in a test loop and adding water at 400 ppm increments to generate water concentrations in oil of 400 ppm, 800 ppm, 1200 ppm, and 1600 ppm. The nominal temperatures of oil may be T1=80 degrees Celsius, T2=100 degrees Celsius, and T3=120 degrees Celsius as produced by a thermal bath. FIG. 30 depicts a scores plot of a developed PCA model illustrating that responses of the resonant sensor to additions of water at different temperatures may be in different directions. Each individual arrow in FIG. 30 points in the direction of increasing water concentrations at oil temperatures T1, T2, and T3. FIG. 31 may depict results of multivariate linear regression model using partial least squares (PLS) technique to quantify water concentrations in oil using responses of the single sensor. The PLS technique may determine correlations between the independent variables and the sensor response by finding the direction in the multidimensional space of the sensor response that explains the maximum variance for the independent variables. FIG. 32 shows that such multivariate linear regression may be able to predict water concentrations independent of oil temperature.

Figure 33:
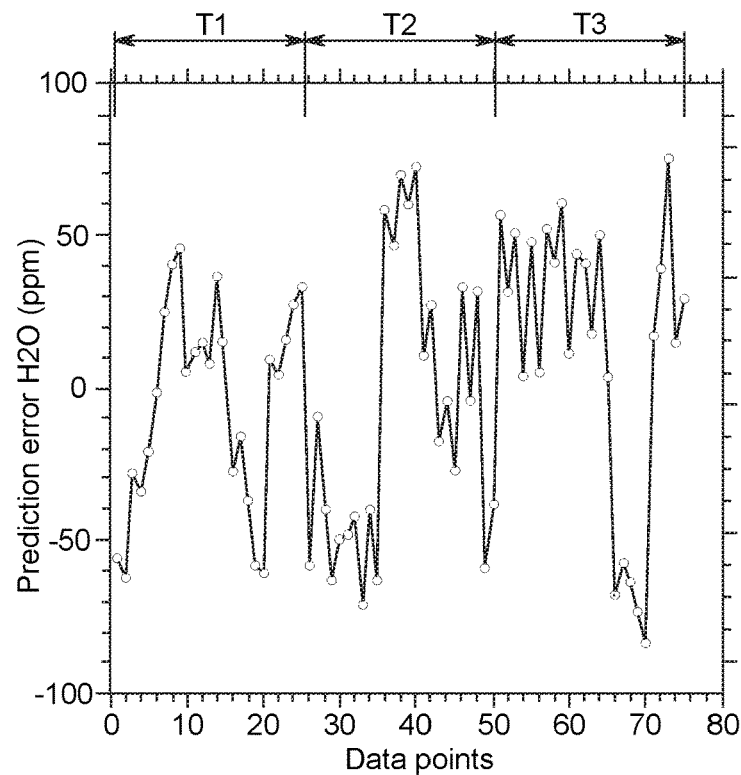
FIG. 33 is a plot of prediction error between actual and predicted concentrations of water in oil over time at three temperatures.
Figure 34:
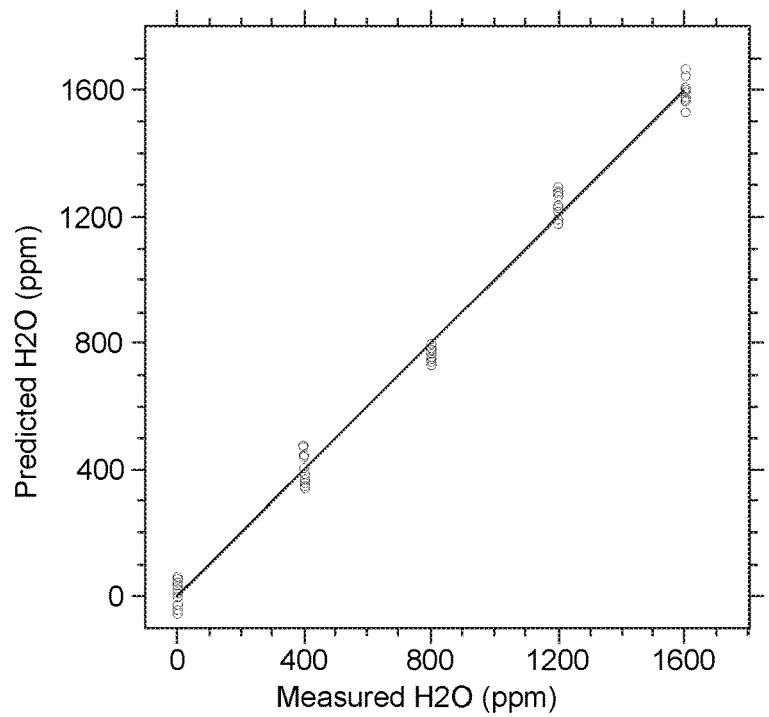
FIG. 34 is a plot of correlation between actual (measured) and predicted concentrations of water in oil at three temperatures.

Analysis of this sensor data of determination of water in oil (0 ppm, 400 ppm, 800 ppm, 1200 ppm, and 1600 ppm) at different nominal temperatures of oil (80 degrees Celsius, 100 degrees Celsius, and 120 degrees Celsius) may be performed using a multivariate non-linear (quadratic) regression. FIG. 32 depicts the actual (measured) concentrations of water in oil at three temperatures (solid line) and predicted concentrations (open circles). FIG. 33 depicts prediction error between actual and predicted concentrations of water in oil at three temperatures. FIG. 34 depicts a correlation plot between actual (measured) and predicted concentrations of water in oil at three temperatures.

Figure 35:
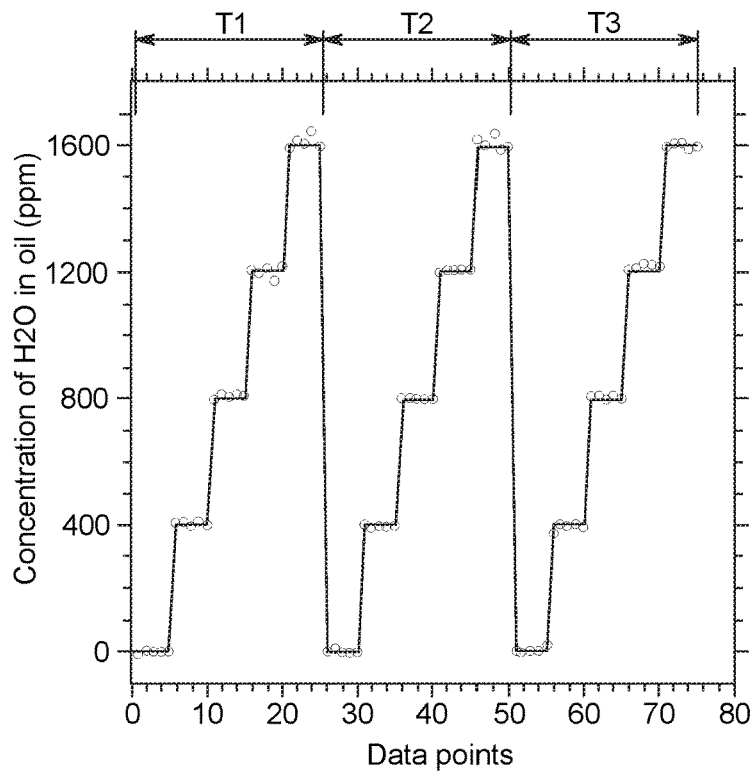
FIG. 35 is a plot of the actual (measured) concentrations of water in oil over time at three temperatures (solid line) and predicted concentrations (open circles) using responses of a multivariable resonant sensor and oil temperature sensor.
Figure 36:
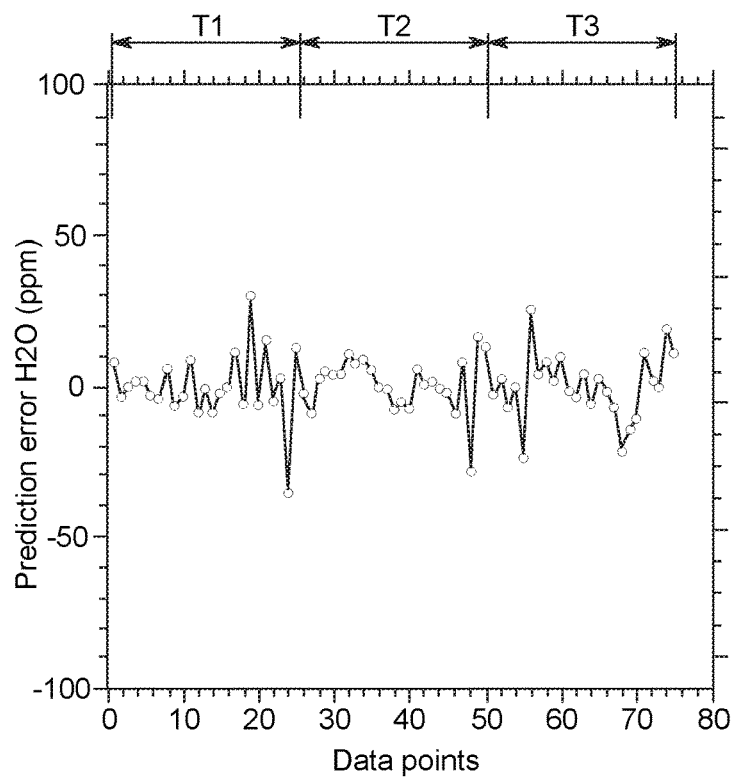
FIG. 36 is a plot of prediction error between actual and predicted concentrations of water in oil over time at three temperatures using responses of a multivariable resonant sensor and oil temperature sensor.
Figure 37:
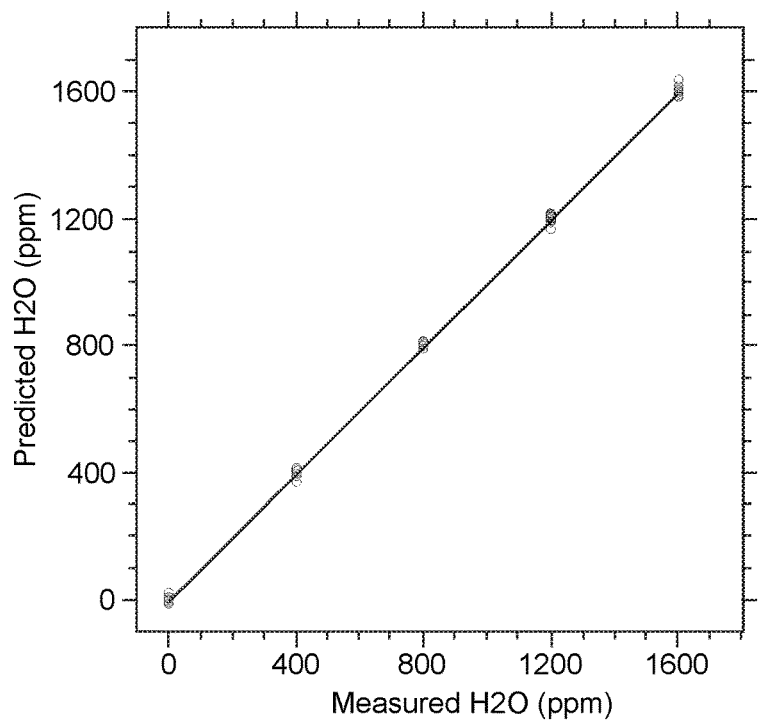
FIG. 37 is a plot of correlation between actual (measured) and predicted concentrations of water in oil at three temperatures using responses of a multivariable resonant sensor and oil temperature sensor.

Analysis of this sensor data of determination of water in oil (0 ppm, 400 ppm, 800 ppm, 1200 ppm, and 1600 ppm) at different nominal temperatures of oil (80 degrees Celsius, 100 degrees Celsius, and 120 degrees Celsius) may be further performed using a multivariate non-linear (quadratic) regression with an additional input from a temperature sensor positioned in measured oil. FIG. 35 depicts the actual (measured) concentrations of water in oil at three temperatures (solid line) and predicted concentrations (open circles). FIG. 36 depicts prediction error between actual and predicted concentrations of water in oil at three temperatures. FIG. 37 depicts a correlation plot between actual (measured) and predicted concentrations of water in oil at three temperatures.

Figure 38:
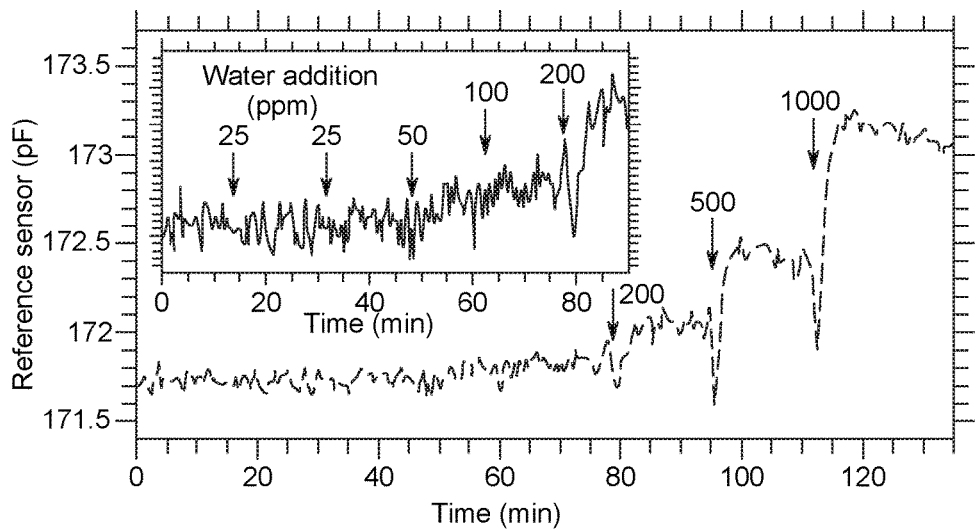
FIG. 38 is a response of a reference capacitance sensor to water leaks into engine oil at levels of 25, 25, 50, 100, 200, 500, and 1000 ppm each. Inset shows response to initial water leaks.
Figure 39:
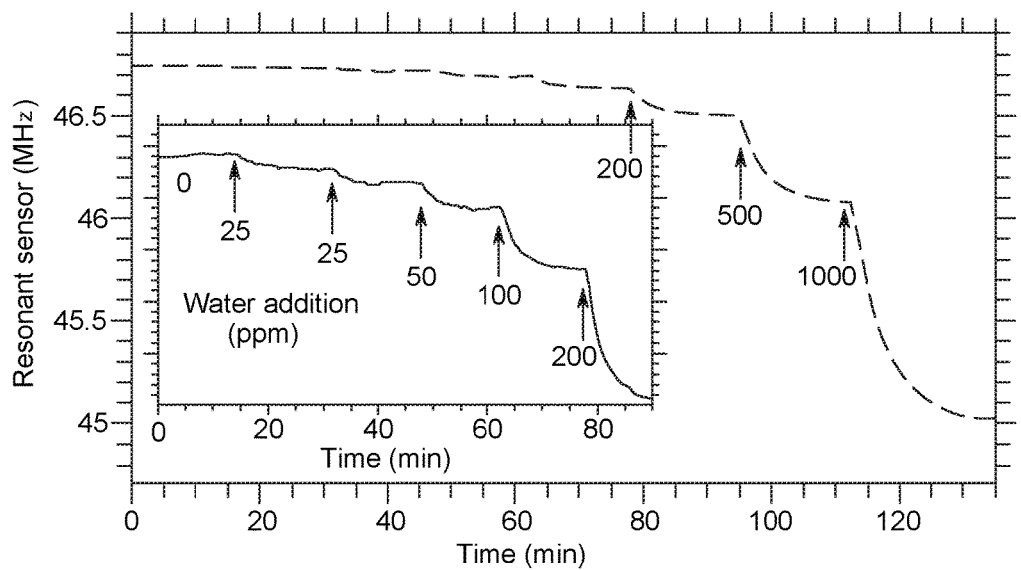
FIG. 39 is a response of a developed resonant sensor to water leaks into engine oil at levels of 25, 25, 50, 100, 200, 500, and 1000 ppm each. Inset shows response to initial water leaks.

The performance of this developed resonant sensor may compare with the performance of a standard non-resonant capacitance sensor that served as a reference capacitance sensor. This reference capacitance sensor has two co-axis pipes, and it is possible to measure capacitance of the fluid being tested by applying a sinusoidal signal to the inner pipe. The comparison may be performed by having both sensors in the same circulating-oil loop where water leaks may be introduced and presented to both sensors. Water leaks levels may be 25, 25, 50, 100, 200, 500, and 1000 ppm. FIG. 38 depicts the response of a reference capacitance sensor to water leaks into engine oil at levels of 25, 25, 50, 100, 200, 500, and 1000 ppm each. This figure illustrates that the reference capacitance sensor did not show an appreciable signal change from its noise until water leaks of 25, 25, 50, 100, and 200 ppm are all introduced. In contrast, FIG. 39 shows the response of a resonant sensor to water leaks into engine oil according to an embodiment, where this sensor may detect the smallest water leak at 25 ppm as well as all other water leaks presented to both sensors.

Figure 40:
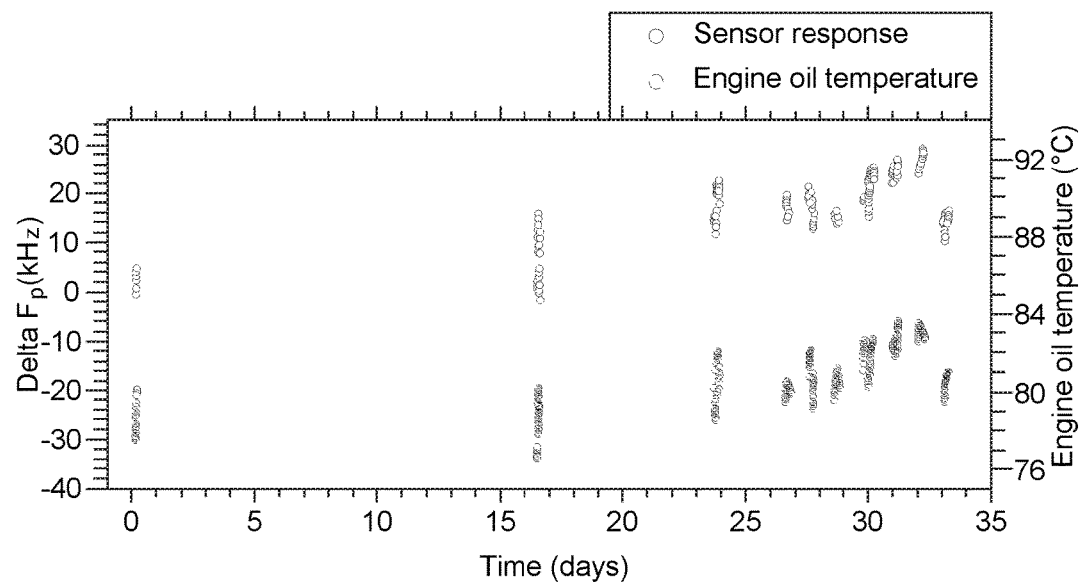
FIG. 40 shows operation of the developed resonant sensor in a single cylinder locomotive engine.
Figure 41:
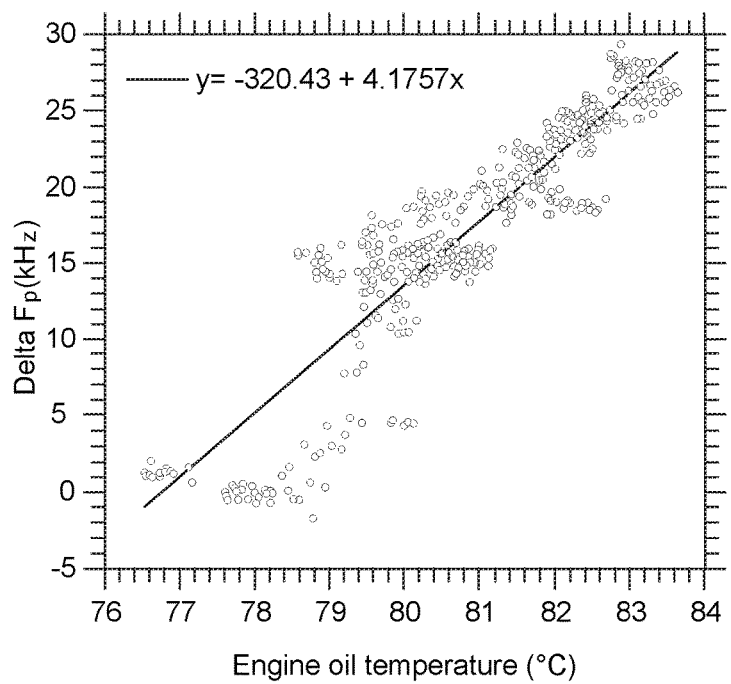
FIG. 41 shows correlation between response of the developed resonant sensor in a single cylinder locomotive engine and the temperature of oil.

The resonant sensor may be tested in a single cylinder locomotive engine test bed for about 34 days. FIG. 40 is a graph depicting results of temperature of oil and sensor response after operating the developed resonant sensor in a single cylinder locomotive engine test bed for a period of 34 days. FIG. 41 illustrates a correlation between response of the developed resonant sensor in a single cylinder locomotive engine for about 34 days and the temperature of oil.

In another example, sources of leaks in an engine may be determined by identifying dynamic signatures of the leaks, relating the identified signature with a known leak signature from a specific engine component, and determining the location of the leak based on the signature or relationship. Such approach may provide the ability for proactive maintenance, replacing reactive maintenance, and may increase the time-in-use for assets having lubrication systems or internal combustion engines.

Figure 42:
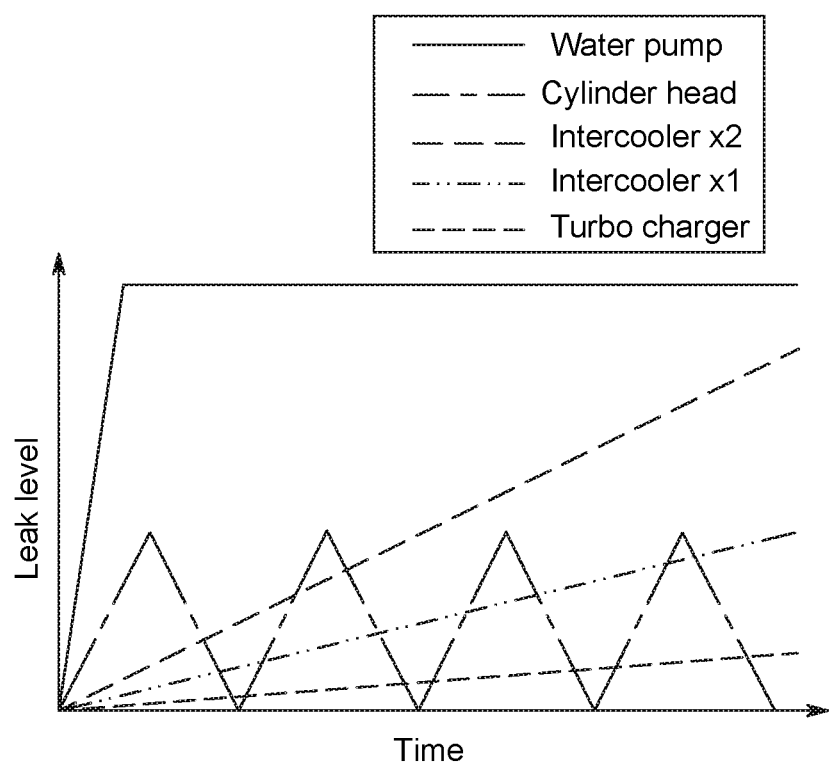
FIG. 42 is a schematic of dynamic signatures of leaks in typical components in an internal combustion engine.

Non-limiting examples of such assets with internal combustion engines include various vehicle types, each having its own set of operating parameters. Embodiments disclosed herein may provide a prognostics sensor tool for early determination of leaking components via dynamic leak signatures. These sensors may be applied in multiple locations in the engine to pinpoint the origin of leak. FIG. 42 depicts a schematic of dynamic signatures of leaks of a turbo charger (1-2 turbo chargers per engine), an intercooler (2 intercoolers per engine), a water pump (1 water pump per engine), and a cylinder head (12-16 cylinder heads per engine).

Figure 43:
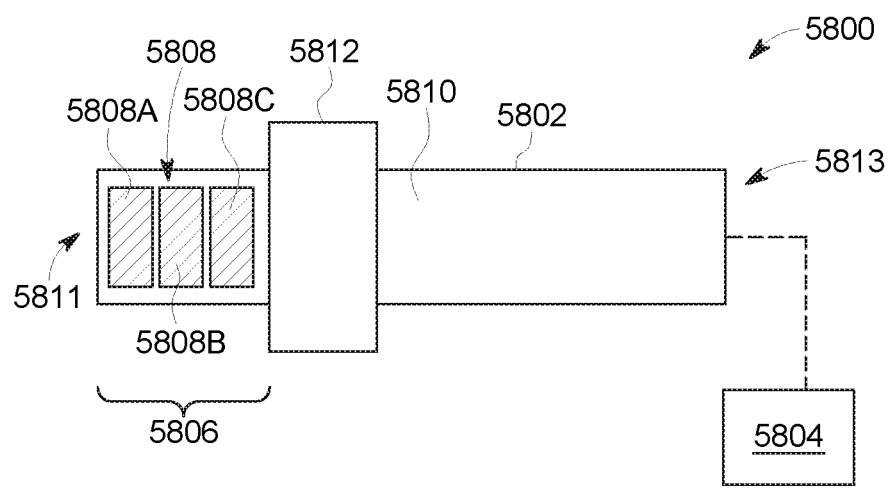
FIG. 43 is a schematic diagram of a sensing system that includes a sensor and a sensor reader.

FIG. 43 is a schematic diagram of a sensing system 5800 that includes a sensor 5802 and a sensor reader 5804. The sensor reader 5804 may be at least similar to the sensor reader 2659B shown in FIGS. 11 and 12. The sensor 5802 includes a sensing region 5806 that includes multiple electrodes 5808. The sensing region 5806 is configured to be placed in operational contact with an industrial fluid of interest, such as an oil, a fuel, or a solvent. The electrodes 5808 may contact the industrial fluid directly or indirectly due to a dielectric sensing layer that may cover at least some of the electrodes 5808. The sensing layer is applied to improve detection of water or other polar compounds in an industrial fluid. The sensing layer may be an inorganic sensing layer, unlike some conventional sensors that use polymeric sensing layers. Polymeric sensing layers in conventional resonant sensors operate by swelling and changing the resonant frequency of the sensor. In the sensor 5802, water uptake by the sensing film does not produce swelling and does not change film thickness. Rather, water uptake produces a change in the dielectric property and the capacitance of the sensing film at multiple frequencies. Unlike conventional resonant sensors, the sensor 5802 produces dielectric property changes of the sensing film at multiple frequencies (produced using tuning components illustrated in FIGS. 4 and 5) that allows more accurate determinations of the contaminants, such as water or other polar compounds. Such improved accuracy is provided by measurements of spectral dispersion of the sensing film before and after fluid contamination. Non-limiting examples of water sorbing or sensing layers include porous silicon porous ceramic, anodized aluminum oxide, and others. The sensing region 5806 has an electrode geometry that matches the measurement needs of the sensing region 5806.

The sensor 5802 in an embodiment includes a probe body 5810 that has a shoulder 5812 extending outward from the probe body 5810 such that the shoulder 5812 has a greater radial width or diameter than the probe body 5810. The shoulder 5812 is disposed along an intermediate segment of the probe body 5810. The sensing region 5806 extends from the shoulder 5812 to a distal end 5811 of the probe body 5810. A proximal end 5813 of the probe body 5810 is operably coupled to the sensor reader 5804. The electrodes 5808 are disposed on the sensing region 5806 at different distances relative to the shoulder 5812 such that the electrodes 5808 extend different depths into the industrial fluid. In an embodiment, at least two of the electrodes 5808 operate at one or more high frequencies and at least one of the electrodes 5808 (that is different than the electrodes 5808 that operate at high frequencies) operates at one or more low frequencies.

For example, the sensor 5802 in the illustrated embodiment includes multiple sensing sub-regions that each includes one or more electrodes 5808 disposed therein. The sub-regions with electrodes each contain electrode structures where these structures are two-electrode structures or four-electrode structures. The sensing sub-regions include a distal sensing sub-region 5808A, an intermediate sensing sub-region 5808B, and a proximal sensing sub-region 5808C. The electrodes 5808 in the intermediate sub-region 5808B are located between the distal sub-region 5808A and the proximal sub-region 5808C. The electrodes 5808 in the different sub-regions 5808A-C may operate at different frequencies and/or frequency ranges relative to one another. Some of the electrodes 5808 in the different sub-regions 5808A-C may be used for contaminant (such as water) concentration detection, while other electrodes 5808 in the different sub-regions 5808A-C may be used for fluid aging detection. As an alternative to water, some examples of other contaminants that may be detected by the sensing system 5800 include fuel, dust, and other external contaminants. The electrodes 5808 in the different sub-regions 5808A-C may have different electrode spacings between adjacent electrodes 5808.

The distal sensing sub-region 5808A in an embodiment is covered by the sensing layer. The distal sensing sub-region 5808A may be configured to measure low concentration water or other contaminant leaks in oil. Each electrode 5808 in the distal sensing sub-region 5808A may be an interdigitated electrode that has an area in the range from 0.1 mm$^2$ to 100 mm$^2$. The electrode spacing for the electrodes 5808 in the sub-region 5808A may be relatively small, such as in the range from 0.1 µm to 10 µm. For example, the electrodes 5808 may have an area of 2 cm×2 cm with an electrode spacing of 0.15 mm. The electrodes 5808 may resonate at around 50 MHz in air. The electrodes 5808 in the distal sub-region 5808A may be operated at relatively high frequencies and/or frequency ranges compared to the electrodes 5808 in the intermediate and/or proximal sub-regions 5808B, 5808C.

The electrodes 5808 in the intermediate sensing sub-region 5808B are located more proximate to the sensor reader 5804 than the distal sensing sub-region 5808A. The intermediate sensing sub-region 5808B is provided for preferential measurements of leaks of nonpolar external contaminants and fluid aging detection. These electrodes 5808 in an embodiment are not coated with a sensing layer. The electrodes 5808 in the intermediate sub-region 5808B may have relatively small spacing in the range from 0.1 μm to 10 μm. The electrodes 5808 of the intermediate sub-region 5808B may be operated at relatively high frequencies and/or frequency ranges compared to the electrodes 5808 in the proximal sub-region 5808C.

The electrodes 5808 in the proximal sensing sub-region 5808C are disposed more proximate to the sensor reader 5804 than the sensing sub-regions 5808A and 5808B. The electrodes 5808 in the sub-region 5808C are provided for preferential measurements of fluid aging detection. These electrodes are not coated with a sensing layer and can have relatively large spacing in the range from 1 μm to 5000 μm. The electrodes 5808 of the proximal sub-region 5808B may be operated at relatively lower frequencies and/or frequency ranges compared to the electrodes 5808 in the distal and/or intermediate sub-regions 5808A, 5808B. In other embodiments, the sensing region 5806 may include different numbers and/or arrangements of electrodes and/or sensing sub-regions.

With additional reference to FIGS. 4 and 5, the sensor 5802 includes at least one inductor-capacitor-resistor (LCR) resonant circuit having one or more tuning elements 1942. The one or more resonant LCR circuits are configured to generate an electrical stimulus having a spectral frequency range. The electrical stimulus is applied to the industrial fluid at the sensing region 5806 via the electrodes 5808. The electrical stimulus may include multiple electric fields and/or multiple frequencies.

The sensor 5802 is operably coupled to the sensor reader 5804, such as via a mechanical fixed connection, a wired connection, or a wireless electrical connection. For example, the sensor 5802 may include a communication unit (e.g., a transceiver or discrete transmitter and receiver) that wirelessly transmits electrical signals to the sensor reader 5804. The sensor reader 5804 includes one or more processors. The one or more processors may be one or more controllers (e.g., microcontrollers) or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed in the hardware of the one or more processors.

The one or more processors are configured to receive an electrical signal from the sensor 5802 that is representative of a resonant spectral response (or resonant impedance spectra) of the sensing region in operational contact with the industrial fluid in response to the electrical stimulus being applied to the industrial fluid.

The one or more processors are configured to analyze the resonant spectral response and determine properties of the fluid. For example, in one embodiment, the one or more processors may be configured to determine both a water concentration in the industrial fluid and an aging level of the industrial fluid based on the analyzed resonant spectral response. In another embodiment, described herein with reference to FIG. 64, the one or more processors may be configured to determine both a water concentration in the industrial fluid and an acid concentration in the industrial fluid based on the resonant spectral response. The resonant spectral response is indicative of a dielectric dispersion profile of the industrial fluid over the spectra frequency range of the electrical stimulus. The one or more processors may be configured to analyze the resonant spectral response by extracting resonance parameters from the resonant spectral response. The resonance parameters are described with reference to FIGS. 8 and 14.

The concentration of water or other external contaminants in the industrial fluid and the aging level of the fluid may be determined by comparing the extracted resonance parameters to known resonance parameters associated with various water concentrations of the industrial fluid and various aging levels of the industrial fluid. The comparison may include classifying the extracted resonance parameters using an earlier built classification model (as described in steps 2870 and 2872 of FIG. 14) and quantitating the extracted resonance parameters using an earlier built quantitation model (as described in steps 2880 and 2882 of FIG. 14).

In an embodiment, the sensor 5802 includes multiple LCR resonant circuits. Each resonant LCR circuit has a different resonant frequency. The electrical stimulus applied to the industrial fluid is generated over a spectral frequency range that includes or incorporates the resonant frequencies of the resonant LCR circuits such that the impedance spectral response is measured over the resonant frequencies. Optionally, the sensor 5802 may include a multiplexer 1944 (shown in FIG. 4) that is configured to individually control the resonant LCR circuits to tune the electrical stimulus that is applied to the industrial fluid. The multiple resonant frequencies allow the sensing system 5800 to detect multiple variables or properties of the industrial fluid, such as the concentration of water and the age of the fluid. For example, the sensing system 5800 may include four resonant frequencies.

Figure 2:
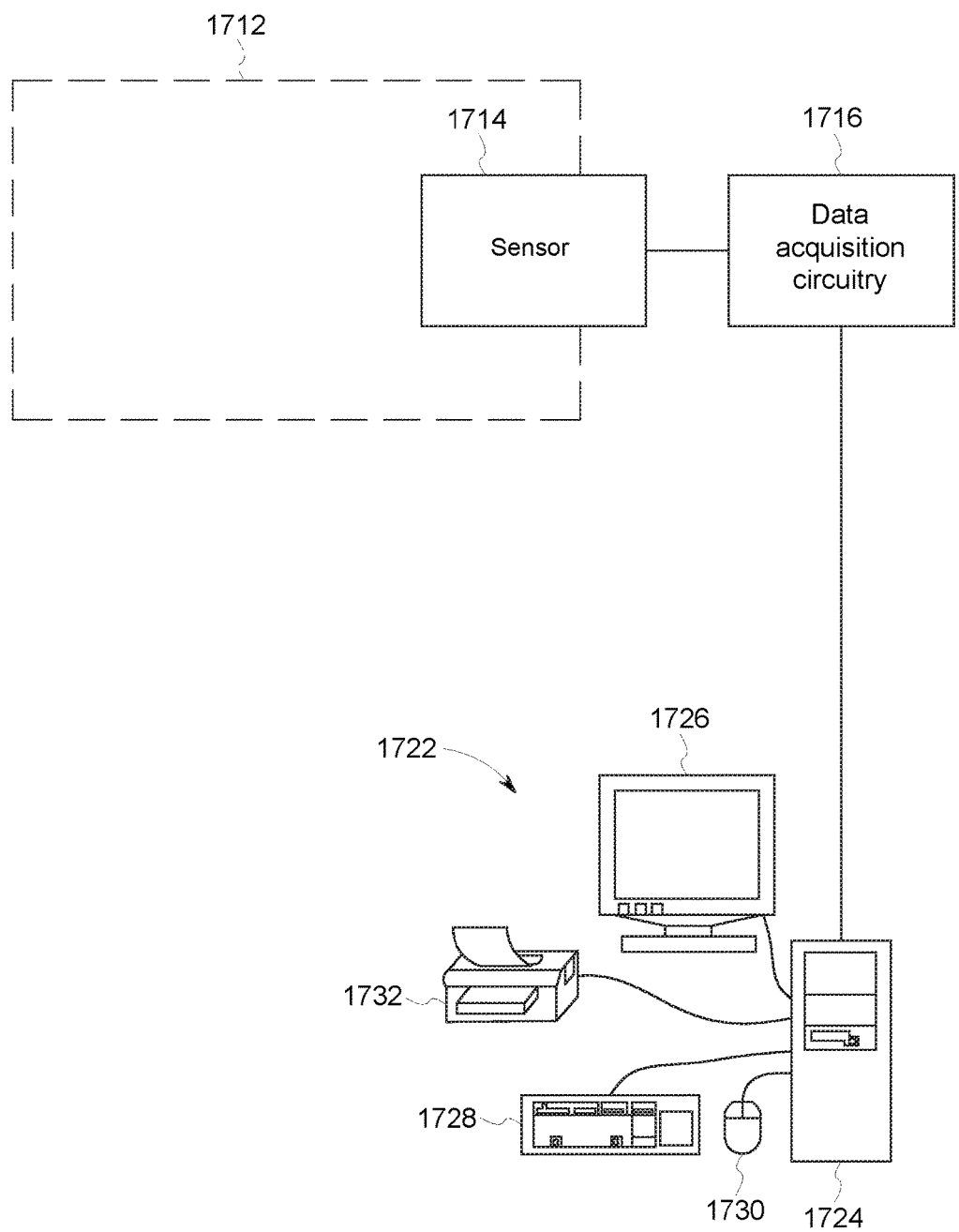
FIG. 2 is a block diagram of a system for assessing fluid according to an embodiment of the disclosure.

The sensor 5802 may also include data acquisition circuitry or sensing region circuitry (not shown), which may be similar to the data acquisition circuitry 1716 shown in FIGS. 2 and 3. The sensing region circuitry is configured to generate an electrical signal representative of the measured resonant impedance spectra. The electrical signal may be transmitted to a processing device with one or more processors, such as the sensor reader 5804, for analysis of the resonant impedance spectra to determine one or more properties of the industrial fluid. The one or more properties in one embodiment are both a concentration of water (or another external contaminant) in the fluid and an aging level of the fluid, and the properties in another embodiment are both a concentration of water (or another external contaminant) and a concentration of acidic components in the fluid.

The analysis of the resonant impedance spectra may be performed by comparing the extracted resonance parameters from the measured resonant impedance spectra from the electrodes in the sensing region (e.g., the sensing sub-regions 5808A, 5808B, and 5808C) to known resonance parameters of the same or a similar fluid at various controlled properties of the fluid, such as defined concentrations of water in the fluid or other external contaminant and at various age levels of the fluid. In an example in which water is the external contaminant, the tested fluid of interest may be determined to have a specific water concentration and a specific age level responsive to the measured set of resonance parameters matching a set of known resonance parameters associated with the specific water concentration and the given age level to a greater extent than the measured set of resonance parameters matches other sets of known resonance parameters associated with other concentrations of water and/or age levels. Statistical methods may be used to compare and "match" the measured resonance parameters to the known resonance parameters. The statistical method used may be a regression analysis, such as a linear regression, a nonlinear regression, or the like. In another example, a series of experiments may be performed using a single sensor to determine the measured resonance parameters of a resonant impedance spectral response of the sensor in a given industrial fluid at various concentrations of water or other external contaminant in the fluid and at various age levels of the fluid, which are the two or more variables that change across the series of experiments. The measured resonance parameters for the series of experiments may be plotted as data points on a graph, and may be used to develop a quantitative model that is used to predict the water or other external contaminant concentration and the age level of monitored fluids (where the water concentration or other external contaminant and the age are unknown). The quantitative model may be a transfer function for the sensing region 5808 broadly or for the individual sensing sub-regions 5808A, 5808B, and 5808C. Thus, measured resonance parameters from a resonance impedance spectral response may be input as variables into the quantitative model to predict water or other external contaminant concentration and aging level of the tested fluid.

The determination of the contaminant concentration in and/or age of the fluid of interest may be performed by establishing correlations between the spectral impedance responses of the sensing sub-regions 5808A, 5808B, and 5808C at multiple frequencies across the dispersion profiles of the fluid and the experimental impedance responses as determined initially via independent reference laboratory methods. Once these correlations (also known as transfer functions) are established, they are further utilized to predict the unknown measured concentrations. Such predictions may be performed by having the measured signals from the sensing sub-regions 5808A, 5808B, and 5808C at multiple frequencies across the dispersion profiles of the contaminant concentration and/or the age of the fluid, entering the values of these signals into the transfer functions or a single function, and obtaining the predicted values of the contaminant concentration and/or the age of the fluid. Depending on the transfer functions, one or more contaminants may be quantified from the measured signals from the sensing sub-regions 5808A, 5808B, and 5808C at multiple frequencies across the dispersion profiles of the contaminants concentration and/or the age of the fluid.

Figure 44:
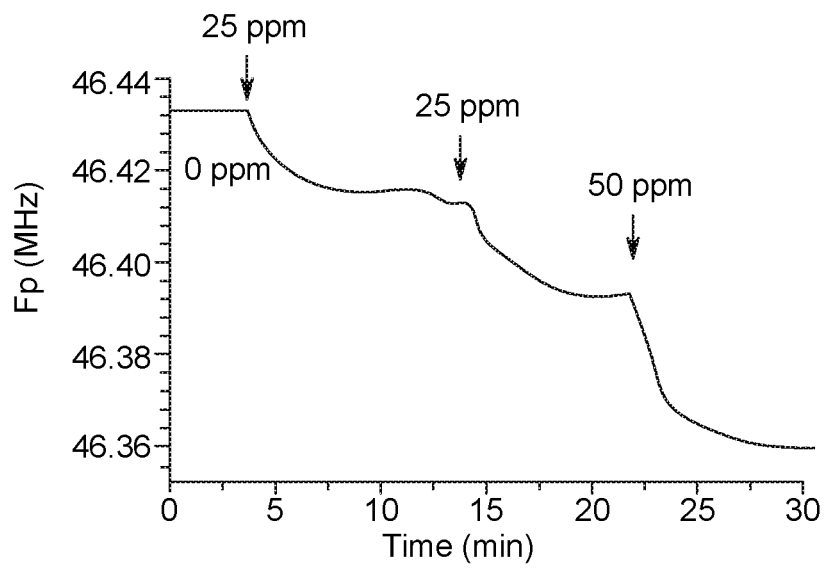
FIG. 44 depicts responses of a developed resonant sensor to water leaks into engine oil at levels of 25 ppm, 25 ppm, and 50 ppm each.

The concentrations of water or other external contaminants detected by the sensor 5802 may be down to 1 ppm. FIG. 44 depicts responses of this developed resonant sensor 5802 to water leaks into engine oil at levels of 25 ppm, 25 ppm, and 50 ppm each. The water levels indicate additions of water, so the second addition of water at 25 ppm results in doubling the amount of water added to the sample fluid, and the third leak level results in four times the concentration of water relative to the first leak level. The data in FIG. 44 illustrates that this sensor 5802 may detect the water leaks at the lowest tested level of 25 ppm with high signal-to-noise ratio quality, resulting in the ability to resolve 1 ppm of water leak with a signal-to-noise (S/N) ratio of 3.

Figure 45:
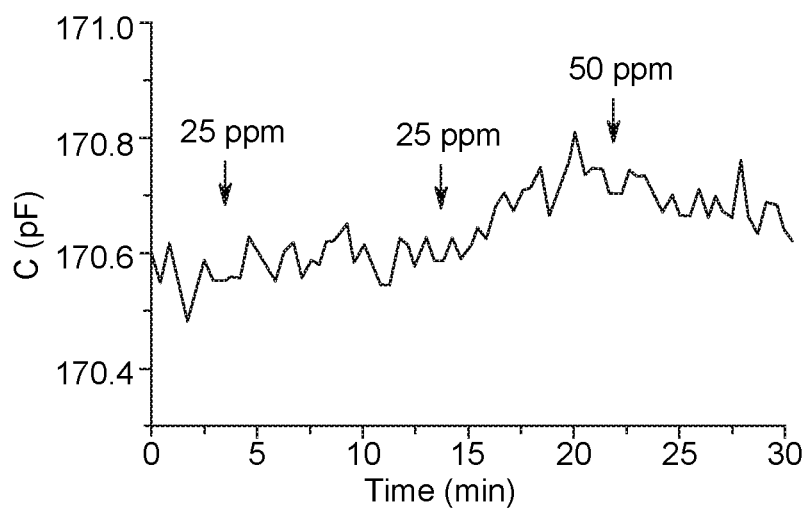
FIG. 45 depicts the response of a reference capacitance sensor to water leaks into engine oil at levels of 25 ppm, 25 ppm, and 50 ppm each.

The performance of this developed resonant sensor may be compared with the performance of a standard non-resonant capacitance sensor that is used as a reference capacitance sensor. The comparison may be performed by having both sensors in the same circulating-oil loop where water leaks may be introduced and presented to both sensors. Water leak levels may be 25 ppm, 25 ppm, and 50 ppm each. FIG. 45 depicts the response of the reference capacitance sensor to water leaks into engine oil at levels of 25 ppm, 25 ppm, and 50 ppm each. This figure illustrates that the reference capacitance sensor did not show an appreciable signal change responsive to the additions of water, likely due to noise. The experimental results indicate an inability of the multivariable resonant sensor 5802 to distinguish among the different concentrations of water leaks.

Figure 46:
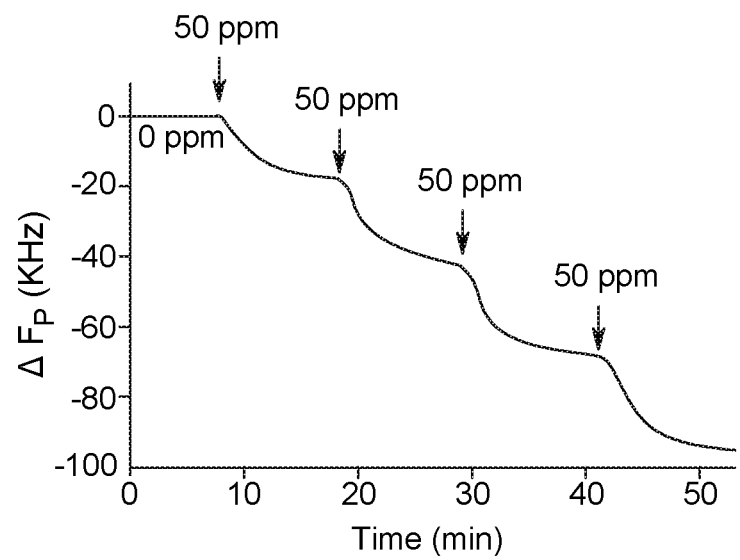
FIG. 46 shows the response of a multivariable resonant sensor to water leaks into engine oil responsive to the 50 ppm steps.
Figure 47:
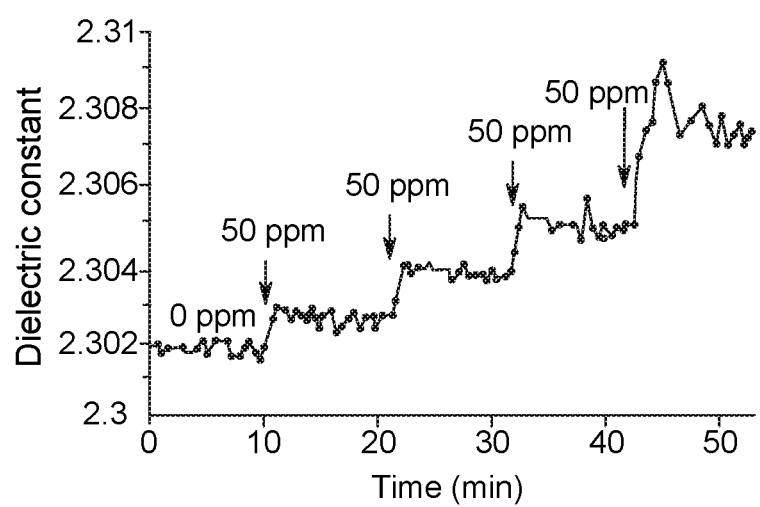
FIG. 47 depicts the response of a control tuning fork sensor to water leaks into engine oil at 50 ppm steps.

Benchmarking of the multivariable resonant sensor 5802 may be performed in comparison to a control or reference tuning fork sensor for quantitation of water leaks into oil. The tuning fork sensor is a mechanical resonator sensor that measures viscosity, density and dielectric constant of a test fluid. The benchmarking was performed by having both the resonant sensor 5802 and the reference tuning fork sensor in the same circulating-oil loop where water leaks were introduced and presented to both sensors. Water leaks levels were induced at 50-ppm steps. FIG. 46 shows the response of the multivariable resonant sensor to water leaks into engine oil responsive to the 50 ppm steps. FIG. 46 indicates that the sensor 5802 detects water leaks with a high signal-to-noise ratio. FIG. 47 depicts the response of the control tuning fork sensor to water leaks into engine oil at 50 ppm steps. The data in FIG. 47 demonstrates a significantly lower signal-to-noise ratio for the control tuning fork sensor relative to the sensor 5802.

In an experimental example, quantitation of water leaks at various stages of oil aging was performed using the sensor of one or more of the embodiments disclosed herein. The industrial fluid was automotive oil 10W-30. Water was added into the oil at different levels ranging from 25 parts per million (ppm) to 900 ppm when oil had three different aging levels. The aging levels were fresh (0% aging), old (100% aging), and intermediate (50% aging). The fresh oil indicates new oil, the old oil indicates oil with a mileage of 5000 miles in an automotive, and the intermediate oil is a 50/50 ratio of fresh and old oil. The oil may be considered new or fresh at or proximate to a beginning of a recommended fluid life of the oil, the oil may be considered old at or proximate to an end of the recommended fluid life of the oil, and the oil may be considered intermediate at or proximate to the middle of the recommended fluid life. For example, for an oil with a recommended fluid life of 5000 miles in a vehicle, the oil may be considered as new or fresh during the first 10% of the recommended fluid life (e.g., during roughly the first 500 miles), the oil may be considered as old for the last 10% of the recommended life (e.g., during roughly the final 500 miles before reaching 5000 miles) and during any additional miles beyond the recommended life, and the oil may be considered as intermediate for the middle 10% of the recommended life (e.g., during the period roughly between miles 2250 and 2750).

Figure 48:
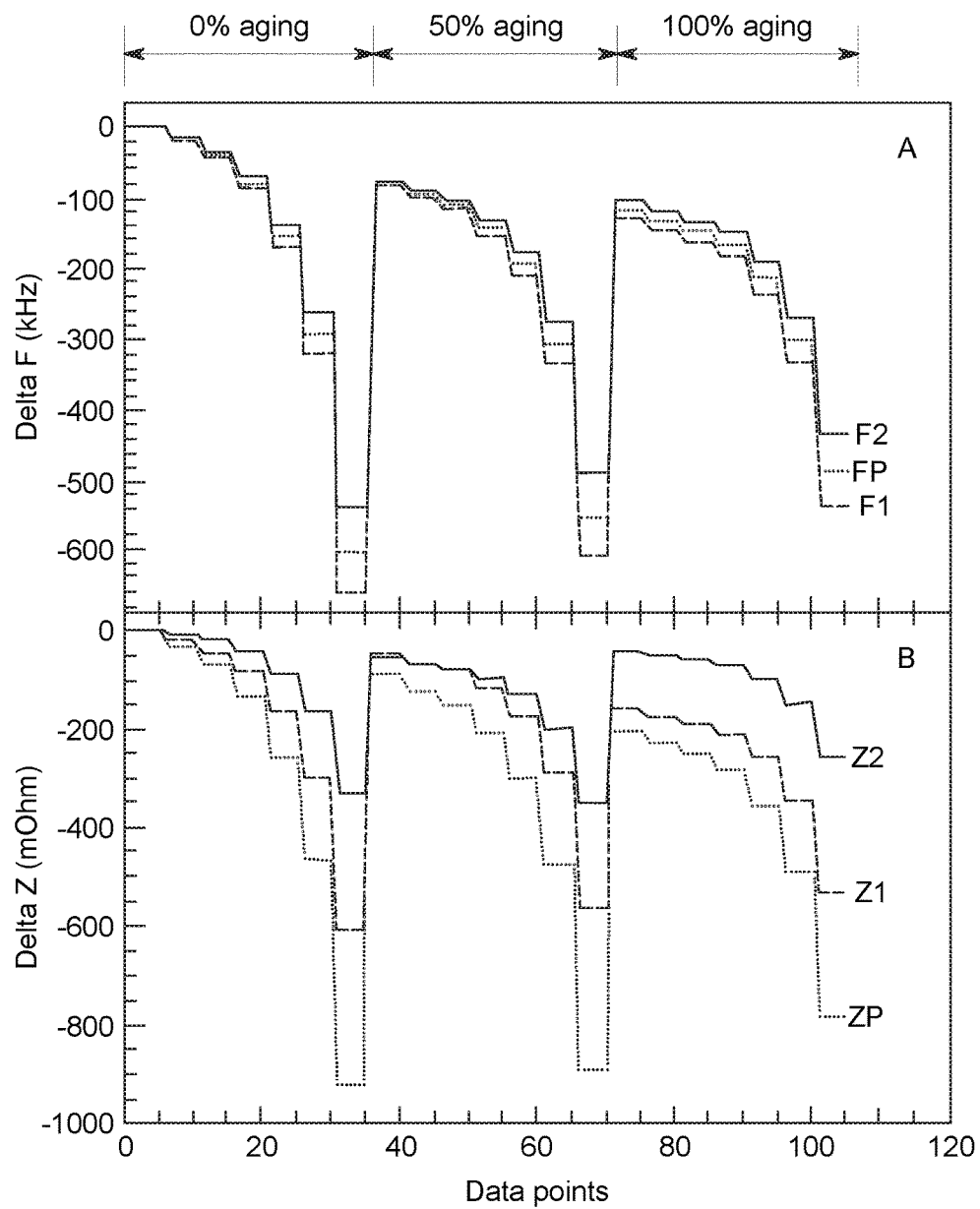
FIG. 48 is a plot depicting raw responses of resonance parameters of a resonant impedance spectra measured by the multivariable resonant sensor.
Figure 49:
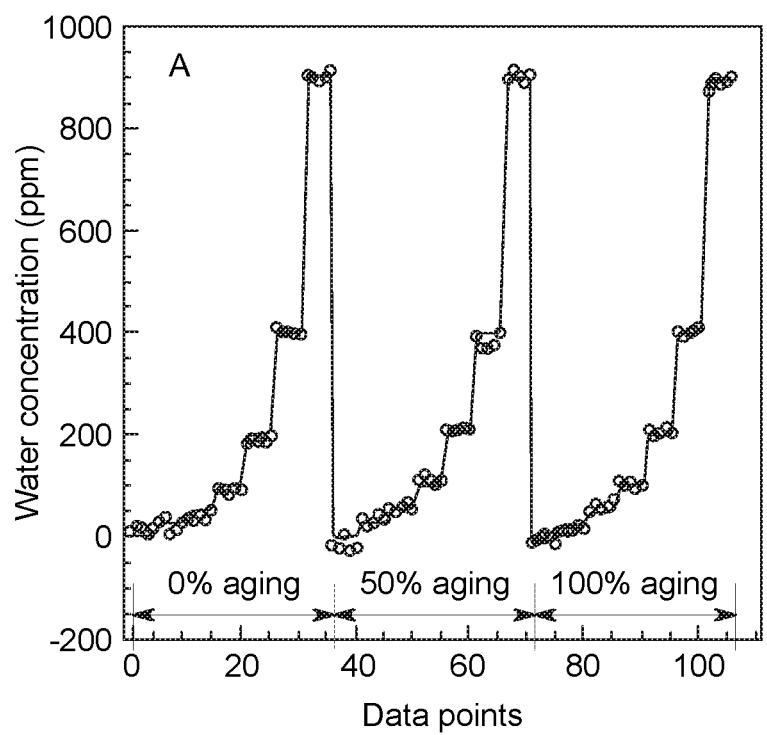
FIG. 49 shows the results of predicted versus actual concentrations for individual different levels of aging.
Figure 50:
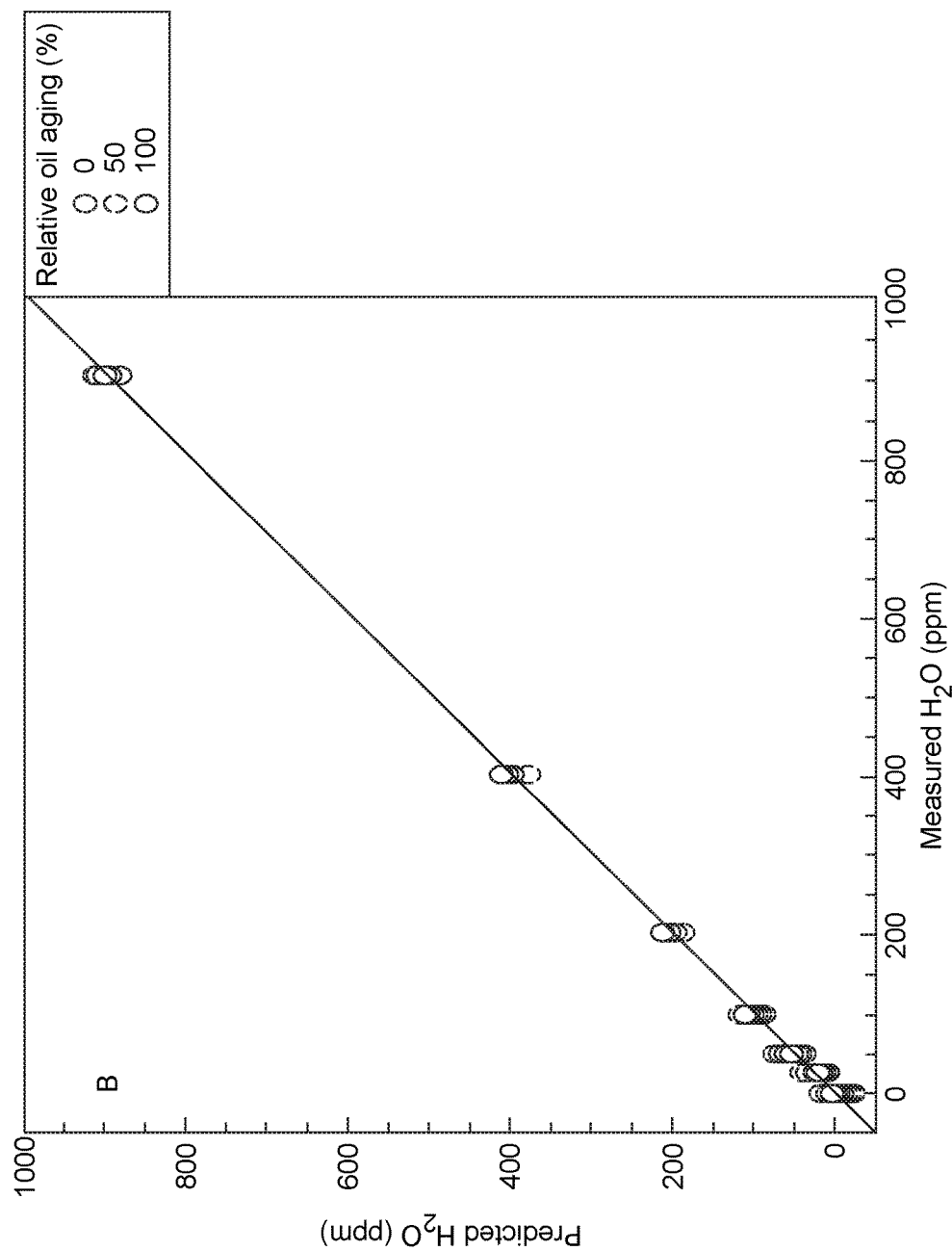
FIG. 50 shows a correlation plot between the actual and predicted water concentrations for three levels of oil aging (e.g., beginning of a recommended oil life, middle of the recommended oil life, or end of the recommended oil life).
Figure 51:
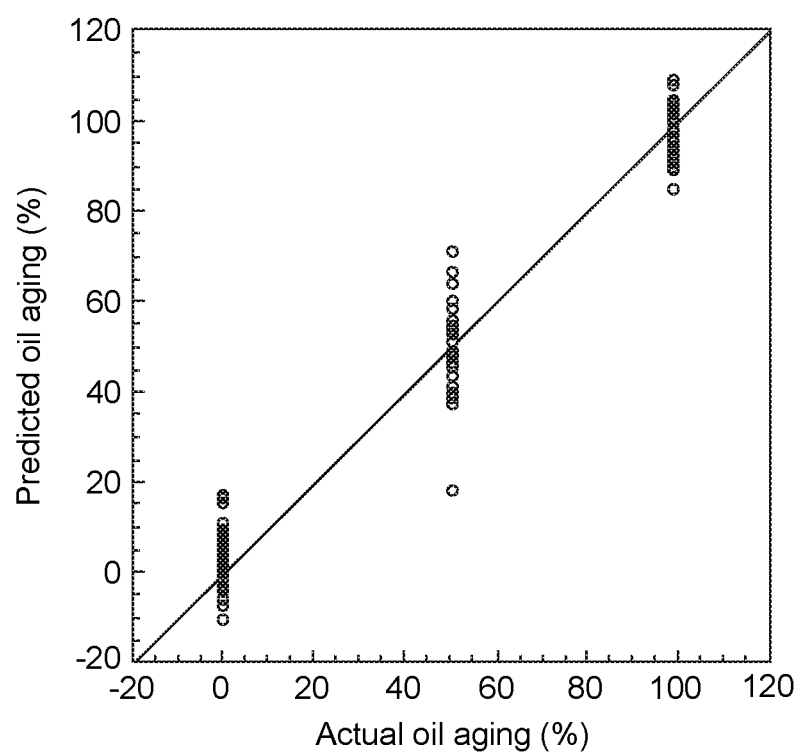
FIG. 51 is a correlation plot between actual and predicted oil aging using the multivariable resonant sensor.

FIG. 48 is a plot depicting the raw responses of the resonance parameters (e.g., F1, F2, Fp, Z1, Z2, and Zp) of the resonant impedance spectra measured by the sensor 5802 (shown in FIG. 43). As shown in FIG. 48, the sensor 5802 responds differently to the water additions depending on the aging levels of the oil samples. A quadratic transfer function was developed based on the raw data obtained in the experiment in order to predict water leaks into the oil. The results of the predicted versus actual concentrations are presented in FIGS. 49 and 50. FIG. 49 shows the results of the predicted versus actual concentrations for individual different levels of aging, and FIG. 50 shows a correlation plot between the actual and predicted water concentrations for the three levels of oil aging (e.g., beginning of a recommended oil life, middle of the recommended oil life, or end of the recommended oil life). The solid plot line represents a quantitative curve or model developed based on a series of experiments using known water concentrations in the oil and known age levels of the oil. The circular data points represent predicted water concentrations and age levels based on resonance parameters extracted or calculated from measured resonant impedance spectral responses of the sensor in contact with fluids of unknown water concentration and unknown age. These results demonstrate that the single developed multivariable sensor discriminates well between water leaks and oil aging and provides the ability to predict water concentrations. FIG. 51 is a correlation plot between actual and predicted oil aging using the sensor, which indicates that the single developed multivariable sensor also discriminates well between oil aging levels and provides the ability to predict oil aging. As a result, the single sensor is able to predict with significant accuracy both the concentration of water in the industrial fluid and the age of the fluid (relative to a recommended fluid life) without the need for multiple sensors to obtain such information.

Figure 52:
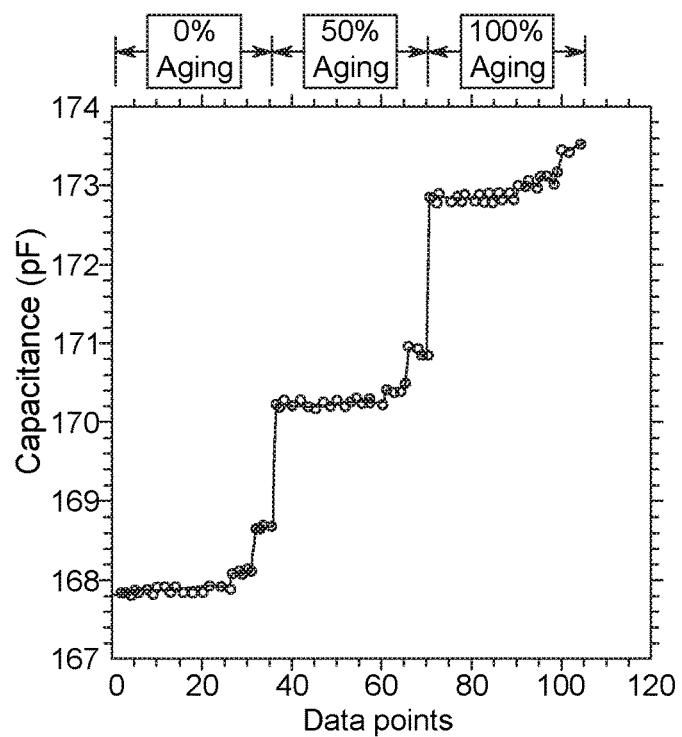
FIG. 52 depicts raw responses of a conventional capacitance sensor to water additions into differently aged oil samples.
Figure 53:
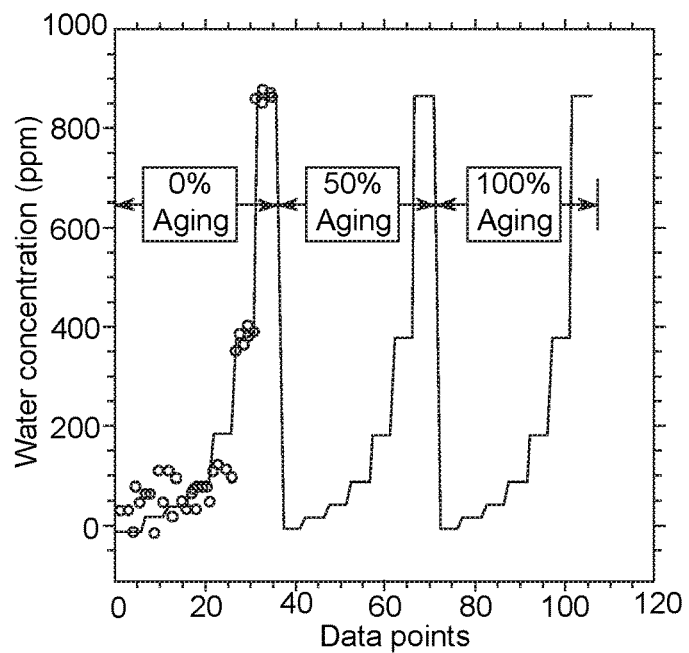
FIG. 53 plots results of predicted vs. actual concentrations of water concentrations for individual different levels of aging measured with a conventional capacitance sensor.

A similar experiment was performed using a conventional capacitance sensor using the same oil and the same water concentrations and aging levels. The results of the experiment indicate that the conventional capacitance sensor does not discriminate between water leaks and oil aging. The conventional capacitance sensor is not able to predict water concentrations at more than one aging level. Measurements were performed simultaneously with the conventional capacitance sensor and the multivariable resonant sensor (e.g., such as the sensor 5802 shown in FIG. 43). FIG. 52 depicts the raw response of the conventional capacitance sensor to water additions into differently aged oil samples. The capacitance sensor responded significantly to differently aged oil samples and less to the water additions into oil. A quadratic transfer function was developed to predict water leaks into fresh oil. Results of the predicted vs actual concentrations of water concentrations for individual different levels of aging measured with a conventional capacitance sensor are presented in FIG. 53. These results demonstrate that a conventional capacitance sensor does not discriminate between water leaks and oil aging and only provides the ability to predict water concentrations in fresh oil.

Figure 54:
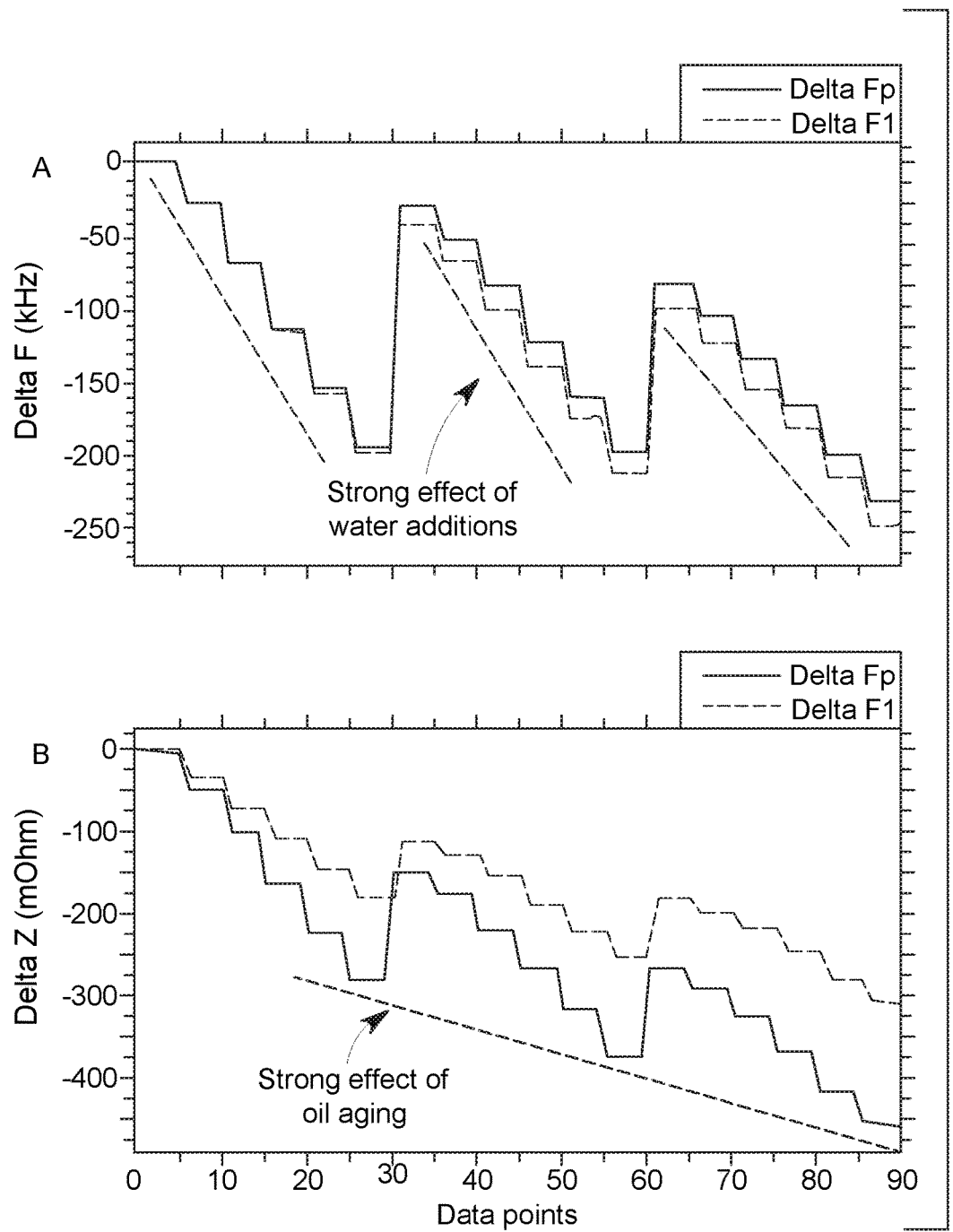
FIG. 54 depicts raw responses of (A) $F_p$, $F_1$, $F_2$ and (B) $Z_p$, $Z_1$, $Z_2$ of the multivariable resonant sensor to water additions into differently aged oil samples.

The performance of the developed multivariable resonant sensor was further benchmarked with the tuning fork sensor in quantitation of water leaks into oil at various stages of oil aging at one temperature. The employed model oil was automotive oil 10W-30 (AutoZone). Water was spiked into oil at 50-ppm levels providing steps of 50, 100, 150, 200, and 250 ppm of total water additions when oil had three levels of aging such as 50, 70, and 100%. FIG. 54 depicts raw responses of (A) $F_p$, $F_1$, $F_2$ and (B) $Z_p$, $Z_1$, $Z_2$ of the multivariable resonant sensor to water additions into differently aged oil samples. The data points corresponding to three levels of aging were from 0 to 30 (aging 50%), from 31 to 60 (aging 70%), and from 61 to 90 (aging 100%). The mileage for aged oil was 5000 miles. The 0% aging was fresh oil; the 100% was oil aged at 5000 miles; the 50% and 70% were 50/50 and 70/30 ratios of fresh and aged oil. The multivariable resonant sensor responded differently to the water additions into differently aged oil samples.

Figure 55A:
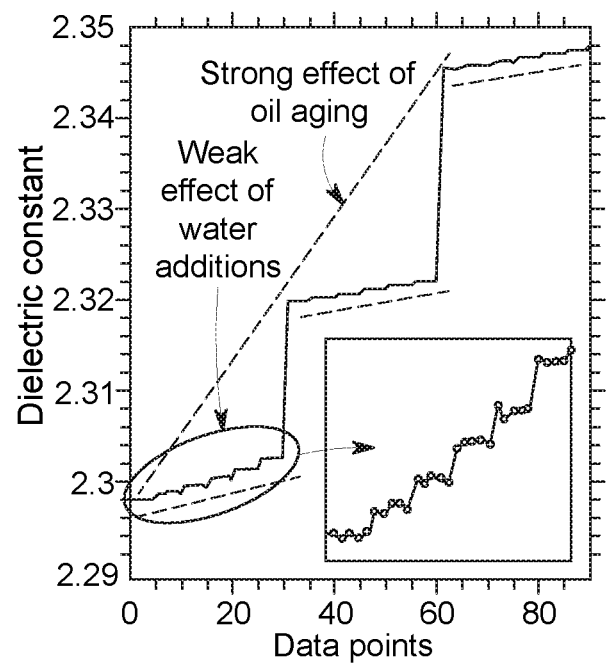
FIGS. 55A-C depict raw dielectric constant, density, and viscosity outputs, respectively, of a tuning fork sensor.
Figure 55B:
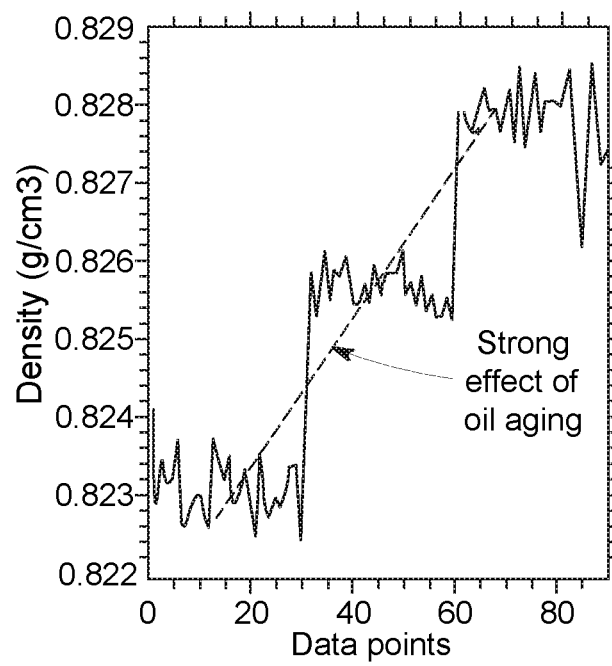
Figure 55C:
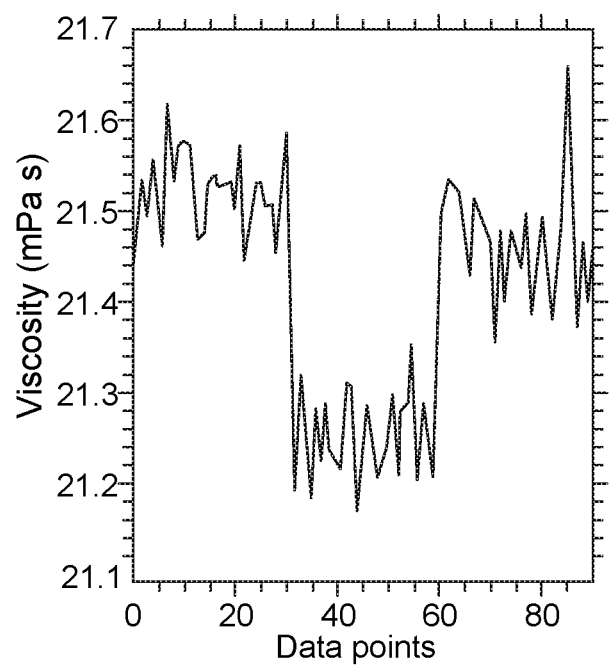

As a benchmark, quantitation of water leaks at various stages of oil aging was performed using the tuning fork. Measurements were performed simultaneously with the tuning fork and the multivariable resonant sensor (e.g., such as the sensor 5802 shown in FIG. 43). FIGS. 55A-C depict the raw dielectric constant, density, and viscosity outputs, respectively, of the tuning fork sensor. The tuning fork sensor responded strongly to differently aged oil samples and relatively much less to the water additions into oil as depicted in FIG. 55A. Response of the tuning fork to oil aging was dominating over the response to water leaks. In particular, dielectric constant response (FIG. 55A) showed strong response to aging (signal jumps at 30 and 60 points) and only relatively small effect of water leaks (small slopes of response over 0-30, 31-60, and 61-90 data points. The density (FIG. 55B) and viscosity (FIG. 55C) outputs showed only responses to aging.

Figure 56:
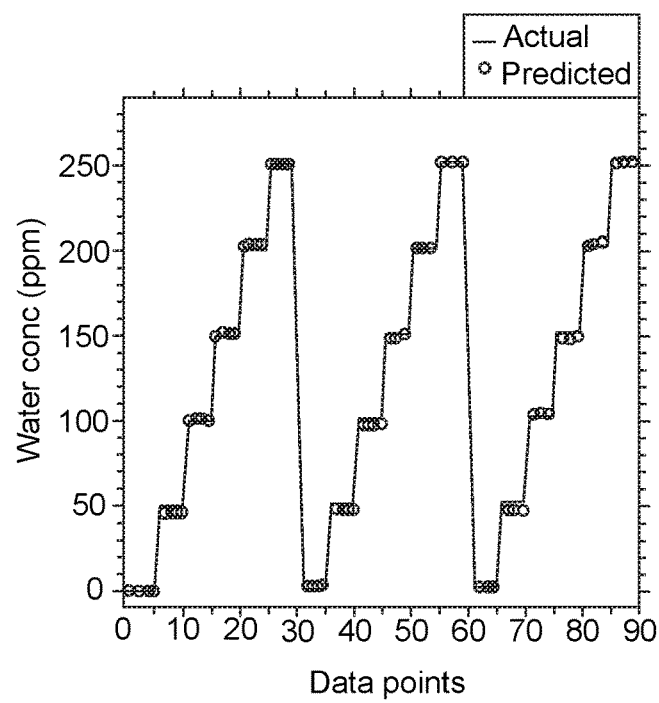
FIG. 56 shows the results of predicted and actual concentrations of water leaks into oil for the multivariable resonant sensor at different oil aging levels.
Figure 57:
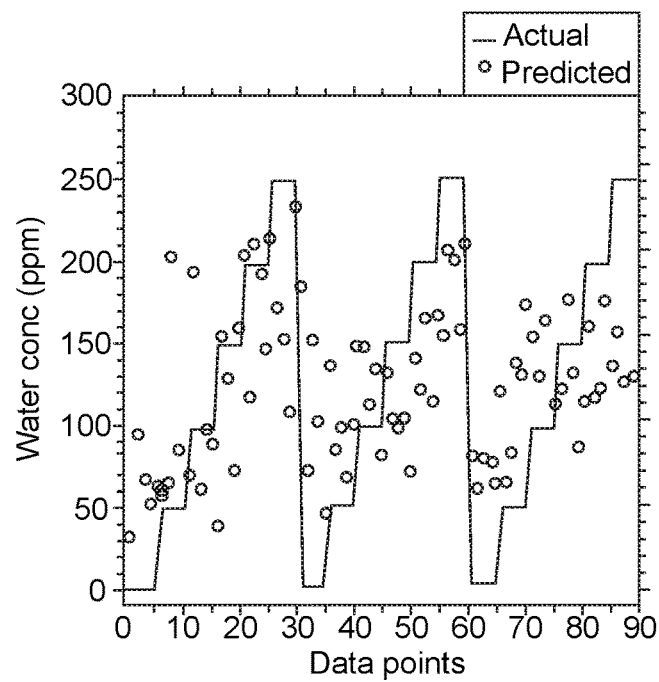
FIG. 57 shows the results of predicted and actual concentrations of water leaks into oil for the conventional tuning fork sensor at different oil aging levels.

Water leaks and oil aging levels were attempted to be quantified using the multivariable resonant sensor (e.g., the sensor 5802 shown in FIG. 43) and the conventional tuning fork sensor. Transfer functions were constructed for each sensor based on their respective outputs. The transfer functions were used to predict water leaks and oil aging levels. The residual prediction errors were evaluated by subtracting actual and predicted values of water leaks and oil aging. FIG. 56 shows the results of predicted and actual concentrations of water leaks into oil for the multivariable resonant sensor at different oil aging levels. These results demonstrate that a single developed multivariable sensor provided the ability to predict water concentrations, as illustrated by the close positioning of predicted values (open circles) to the actual values (solid line) in FIG. 56. FIG. 57 shows the results of predicted and actual concentrations of water leaks into oil for the conventional tuning fork sensor at different oil aging levels. These results demonstrate that the tuning fork sensor was unable to predict water concentrations in oil of different aging levels, as illustrated by the seemingly random scatter of predicted values (open circles) to the actual values (solid line) in FIG. 57.

To determine positions of resonances in the multi-resonant sensor, dielectric properties of fresh and aged oil samples in a broad range of frequencies from 100 Hz to 10 MHz were measured using a dielectric spectroscopy setup consisting of an Agilent 4294A precision impedance analyzer and an Agilent 16452A liquid test fixture. Dielectric spectra were transferred from the 4294A impedance analyzer to a data processing computer using a 4294A data transfer program available from Agilent as a Microsoft Excel macro and was analyzed as described in the 16452A test fixture manual to obtain the real and imaginary parts of the complex dielectric constant ($\varepsilon'$ and $\varepsilon''$, respectively). These measurements were used in the determination of the spectral dispersion properties of oils and allowed the further down selection of operating frequencies for the multi-resonance sensor operation.

Figure 58A:
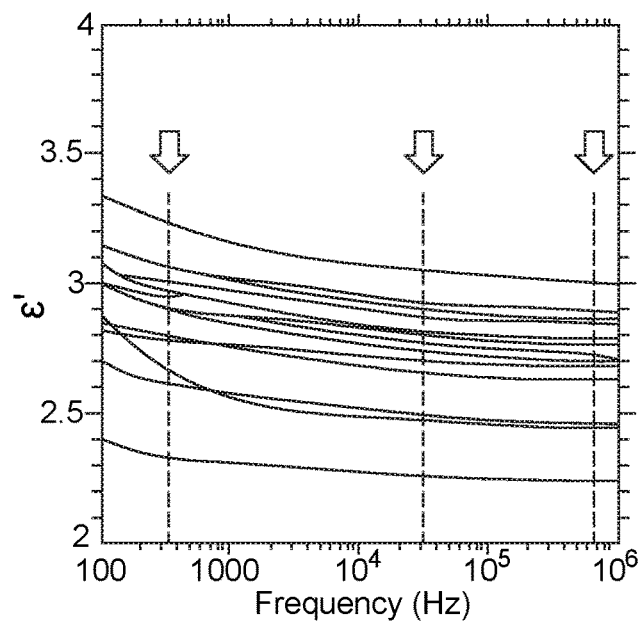
FIGS. 58A-B depict an application of the multiresonant sensor system for the correction for oil aging that shows an example of the selection of operating frequencies of the multiresonant sensor system across the spectral dispersion of locomotive oil.
Figure 58B:
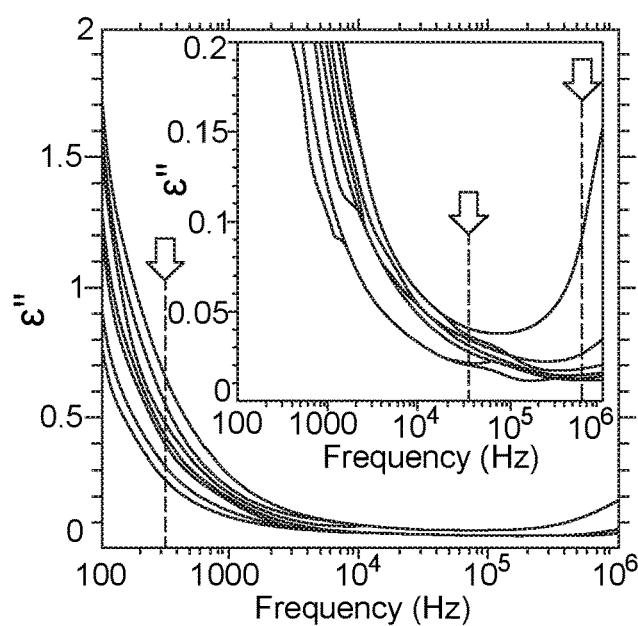
Figure 59A:
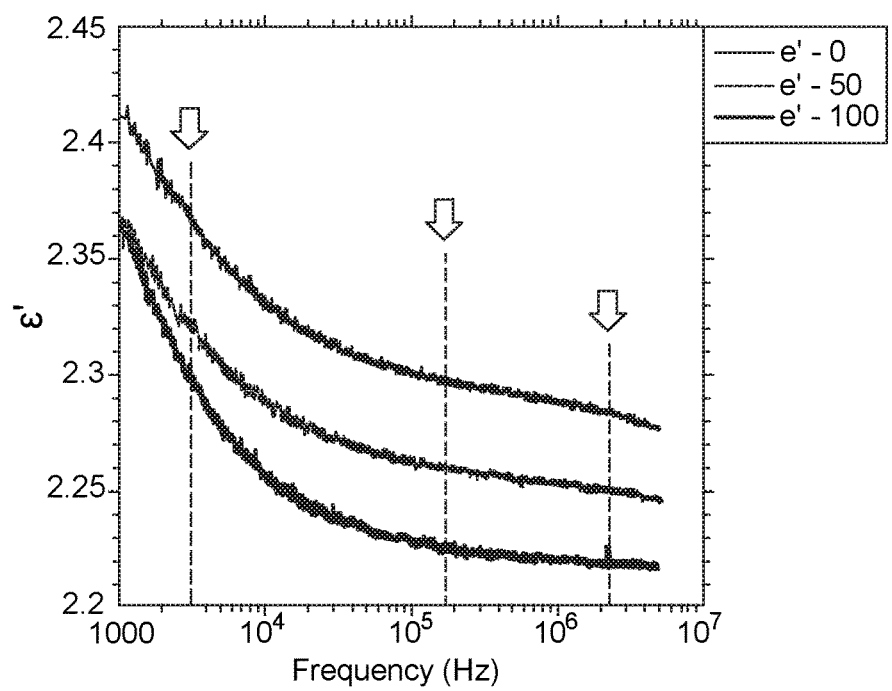
FIGS. 59A-B depict the real and the imaginary portions of the complex permittivity of the employed model automotive oil 10W-30 with three levels of aging such as 0, 50, and 100%.
Figure 59B:
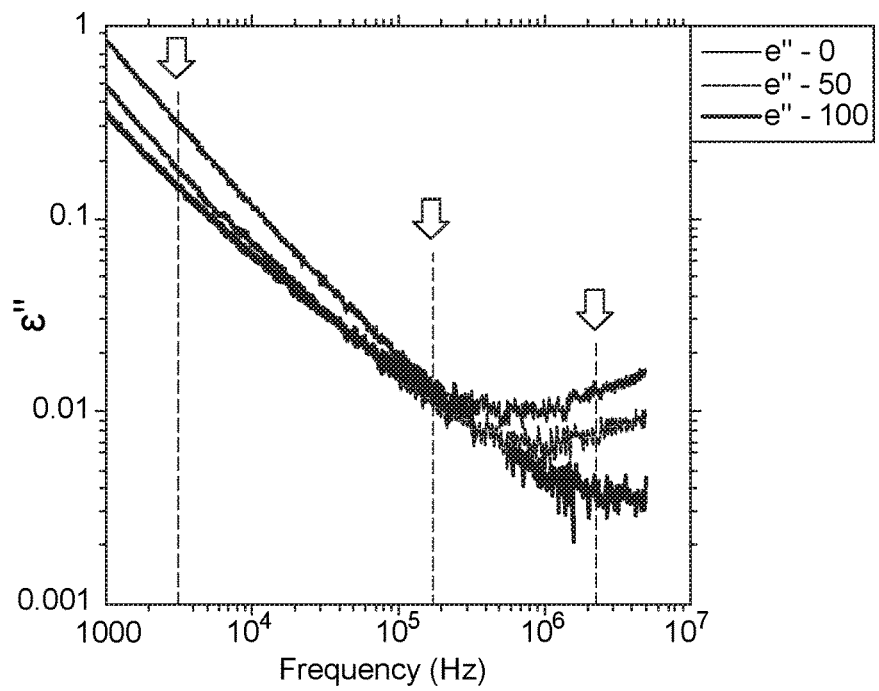

FIGS. 58A and 58B depict an application of the multi-resonant sensor system for the correction for oil aging that shows an example of the selection of operating frequencies of the multiresonant sensor system across the spectral dispersions shown for a range of fresh and used (aged) locomotive oils. FIG. 58A is the real part ($\varepsilon'$) and FIG. 58B is the imaginary part ($\varepsilon''$) of the complex dielectric constant of a locomotive oil. Arrows and dotted lines indicate initially selected regions for the multiresonant sensor operation. The real and the imaginary portions of the complex permittivity are depicted with the initially selected regions for the multiresonant sensor operation. These regions are selected based on the dispersion of ε' and ε" to capture spectral trends upon oil aging. FIGS. 59A and 59B depict the real and the imaginary portions of the complex permittivity of the employed model automotive oil 10W-30 with three levels of aging such as 0, 50, and 100% and illustrates trends of ε' and ε" upon oil aging, which is attractive for the selection of operating frequencies of the multiresonant sensor system. Arrows and dotted lines indicate initially selected regions for the multiresonant sensor operation.

In another experimental example, water leaks into oil were studied during the operation of a helicopter engine. The helicopter engine was a turboshaft CT7 helicopter engine made by GE. Water in the form of an emulsion was added to the oil sump prior to the engine start. A homogenizer was used to emulsify water with the CT7 engine oil. First, the loss of water in the oil during the helicopter engine operation was studied with the near-infrared spectroscopy using a Cary 500i UV-vis-NIR spectrophotometer (Varian, Inc., Santa Clara, Calif.) using quartz cuvettes with a 1-cm path length. Initially, oil samples with known amounts of water were measured to establish the relationship between near-infrared absorbance and water content. Next, samples were taken between the runs of the helicopter engine and analyzed with near-infrared spectroscopy for the presence of residual water. The 500 ppm water was added to the sump of the engine, and then the engine was allowed to run for specified time periods in the ground idle mode. Oil samples were taken between the runs and analyzed with near-infrared spectroscopy for the presence of residual water. The water presence was deduced from the characteristic water absorption band at 1900 nm after the measurement setup calibration with oil-water mixtures with the known water content. The results indicated that for a given concentration of 500 ppm water, water was completely eliminated from the oil in around five minutes on the ground idle. Thus, the water signature could be detected within the first few minutes after the engine start.

Figure 60A:
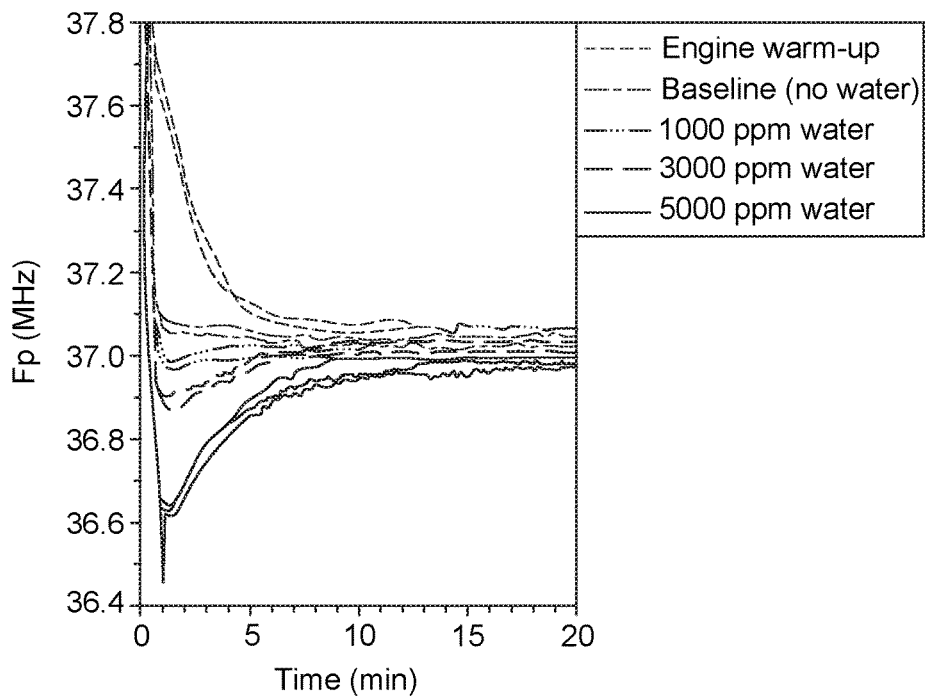
FIGS. 60A-B show the results of triplicate runs with for the engine warm-up, baseline (no added water), and water additions of 1000, 3000, and 5000 ppm, and the correlation between the sensor response and added water concentration, respectively.
Figure 60B:
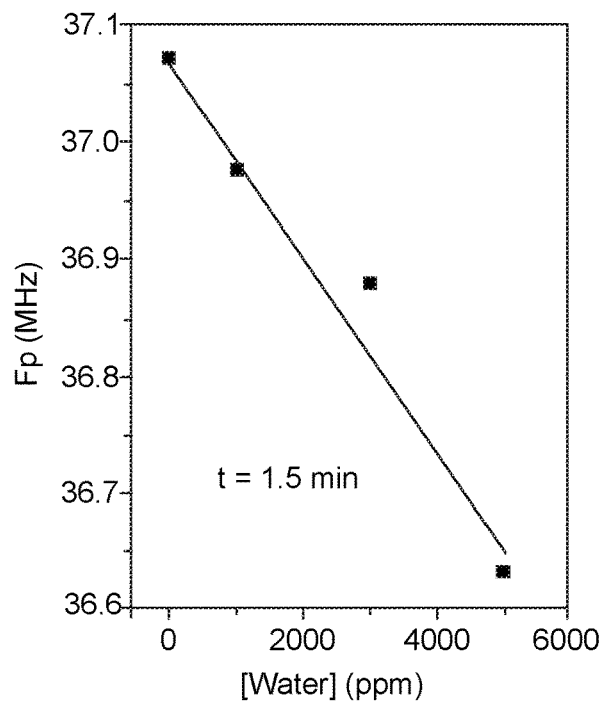

Detection of water concentrations in a turboshaft helicopter engine was further performed using the multivariable resonant sensor (e.g., such as the sensor 5802 shown in FIG. 43). The 4-cm$^2$ 100-μm-IDE-spacing sensor operating at around 38 MHz (in oil) was placed inside a 1-inch T-connector that was a part of a specially installed ⅜" OD bypass oil line connected to the engine to ensure oil flow through the sensor during the engine operation. Benchmarking of the performance of the multivariable resonant sensor was done by comparison with a conventional tuning fork sensor, installed sequentially. Measurements of water leaks were performed by adding water concentrations of 1000, 3000, and 5000 ppm and observing dynamic response patterns. Results of these experiments are summarized in FIG. 60A, which shows the results of triplicate runs with for the engine warm-up, baseline (no added water), and water additions of 1000, 3000, and 5000 ppm. The correlation between the sensor response and added water concentration was established by measuring sensor response after 1.5 min upon water addition, as shown in FIG. 60B.

Figure 61A:
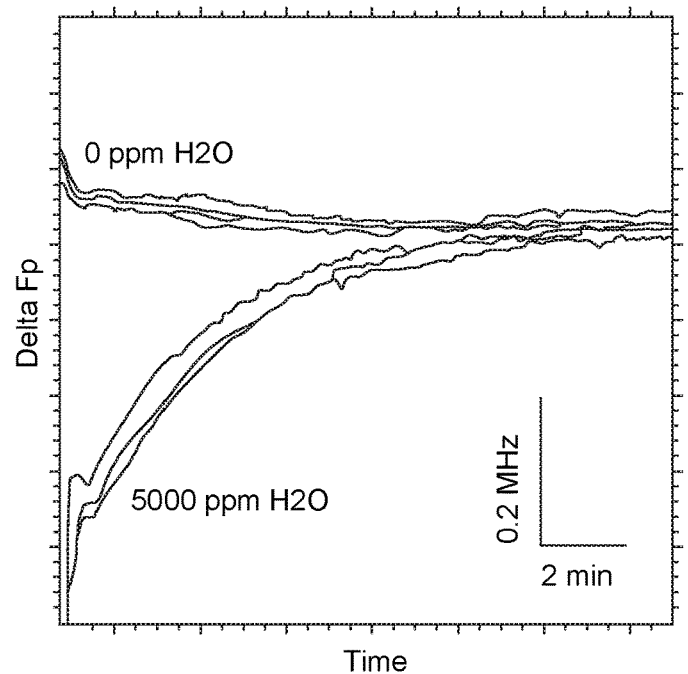
FIGS. 61A-B show responses of an installed multivariable resonant sensor and a tuning fork sensor, respectively, upon testing of engine oil of the turboshaft helicopter with an added 5000 ppm of water and observing dynamic response patterns.
Figure 61B:
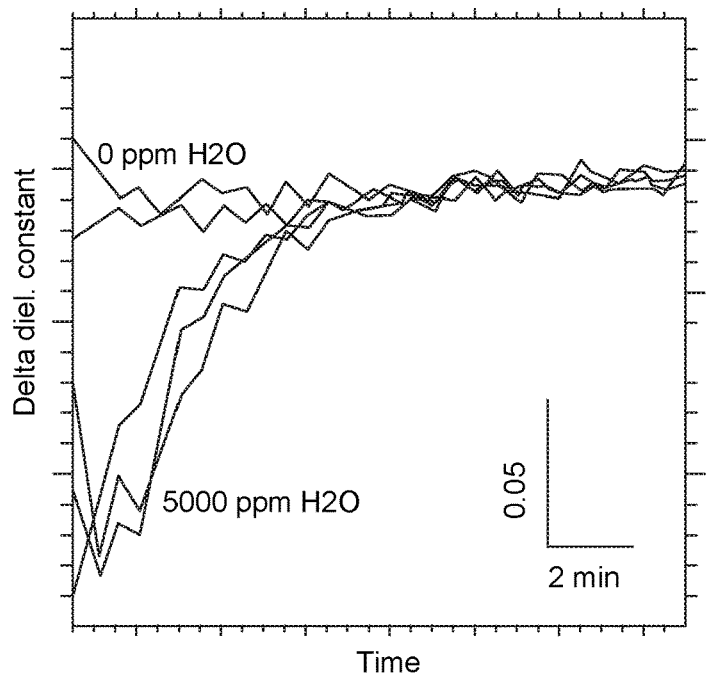

FIGS. 61A and 61B show responses of the installed multivariable resonant sensor and the tuning fork sensor, respectively, upon testing of engine oil of the turboshaft helicopter with an added 5000 ppm of water and observing dynamic response patterns. The tuning fork sensor response shown in FIG. 61B was corrected for the temperature fluctuation during the measurement. The estimated the signal-to-noise ratio of both sensors was taken at their maxima, and the noise levels were taken upon water evaporation at stable response regions during individual runs. As shown in FIG. 61A, the signal-to-noise ratio of the multivariable resonant sensor was in the range of generally 230-525. As shown in FIG. 61B, the signal-to-noise ratio of the tuning fork sensor was in the range of generally 25-60. In FIG. 61B, the dielectric constant increases with the addition of water.

Figure 62:
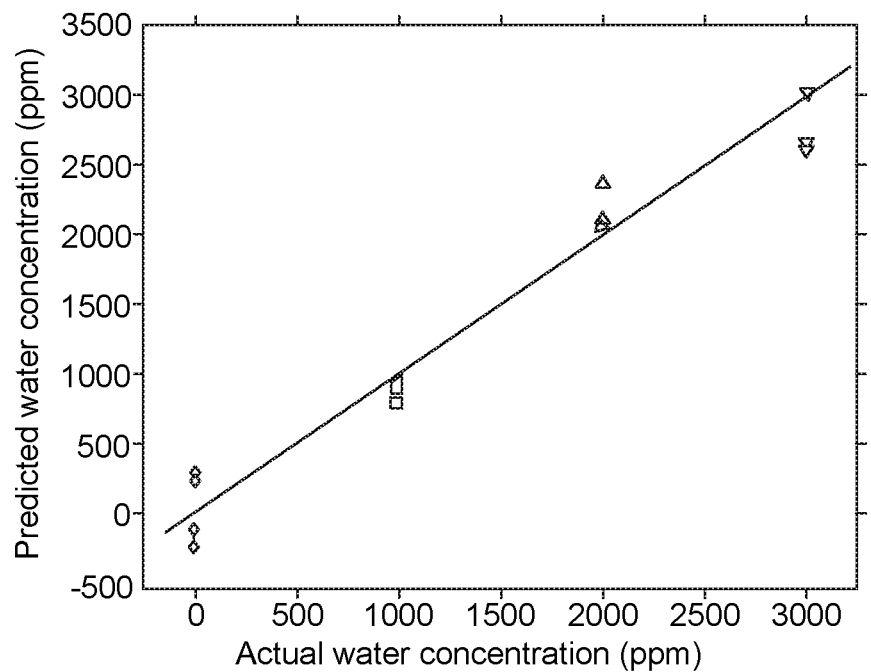
FIG. 62 illustrates results of predicted water concentrations versus actual water concentrations in different types of oils using a single transfer function.

Using an approach of selecting the appropriate frequency ranges as depicted in FIGS. 58A and 58B and FIGS. 59A and 59B, four types of automotive oil were measured with different levels of added water at concentrations of 0 ppm, 1000 ppm, 2000 ppm, and 3000 ppm. The different types of automotive oil were 0W-20, 10W-30, 15W-40, and SAE30. FIG. 62 illustrates results of predicted water concentrations versus actual water concentrations in different types of oils using a single transfer function. The data in FIG. 62 illustrates the ability of the developed sensing methodology to detect and quantify an external contaminant such as water into diverse types of oil without effects of the type of oil.

Figure 63:
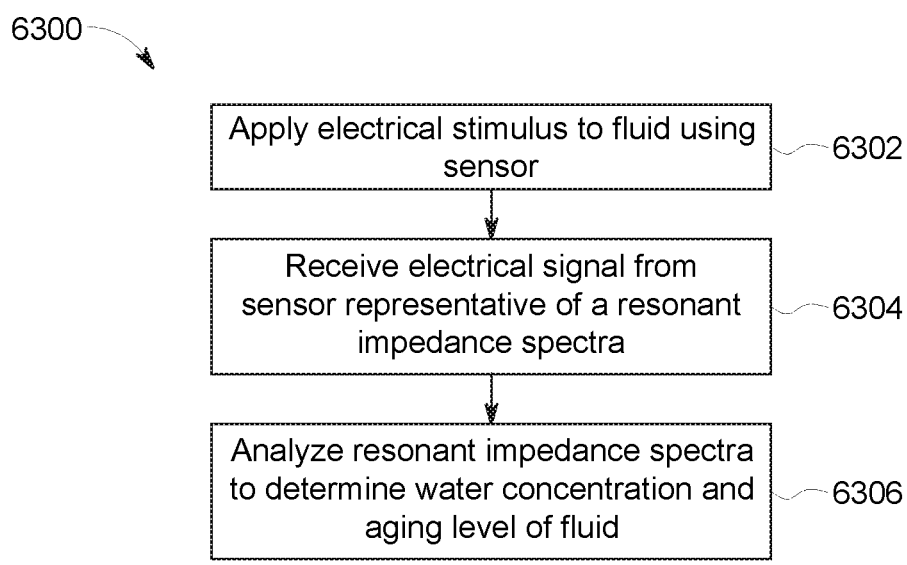
FIG. 63 is a flow chart representative of a method for determining multiple properties of an industrial fluid.

FIG. 63 is a flow chart representative of a method 6300 for determining multiple properties of an industrial fluid. At 6302, an electrical or electromagnetic stimulus is applied to an industrial fluid using a sensor. The "electrical stimulus" may additionally or alternatively be an electromagnetic stimulus. The sensor includes at least one resonant inductor-capacitor-resistor (LCR) circuit configured to generate the electrical stimulus. The electrical or electromagnetic stimulus is applied to the industrial fluid via multiple electrodes at a sensing region of the sensor in operational contact with the industrial fluid. Optionally, the sensor may include multiple LCR circuits that have different resonant frequencies. Applying the electrical or electromagnetic stimulus to the industrial fluid may include generating the electrical or electromagnetic stimulus to incorporate the resonant frequencies of the resonant LCR circuits such that the resonant impedance spectral response is measured over the resonant frequencies of the resonant LCR circuits. The method 6300 may also include tuning the electrical or electromagnetic stimulus generated by the at least one LCR circuit using one or more tuning elements. The tuning elements may include one or more inductors, capacitors, resistors, resonators, or impedance transformers.

At 6304, an electrical or electromagnetic signal is received from the sensor. The electrical or electromagnetic signal is representative of a resonant impedance spectral response of the sensing region in operational contact with the industrial fluid in response to the electrical or electromagnetic stimulus being applied to the industrial fluid. At 6306, the resonant impedance spectral response is analyzed to determine both a water concentration in the industrial fluid and an aging level of the industrial fluid based on the analyzed resonant impedance spectra. Although "water concentration" is mentioned, in other embodiments the concentration may be of another external contaminant other than water. The water or other external contaminant concentration in the industrial fluid and the aging level of the industrial fluid may be determined by comparing the extracted resonance parameters to known resonance parameters associated with various water or other external contaminant concentrations in the industrial fluid and various aging levels of the industrial fluid. The aging level of the fluid is determined by categorizing the fluid as three levels as one of fresh, old, or intermediate. The aging level of the fluid may be also determined by categorizing the fluid with more levels of aging where the number of levels of aging may be 8, 64, 128, or more. The number of aging levels determined by the sensor may depend on the developed transfer function between fluid aging and multivariable sensor response.

The determination of oil aging by levels is important for different applications. For example a two-level aging of oil means that level 1 is a fresh oil and level 2 is aged oil that requires oil replacement or some other action. The higher number of resolution levels of oil aging, the more accurate performed actions can be, including prognostic algorithms to predict the remaining life of oil and/or the machine or an industrial system or site.

Analyzing the resonant impedance spectra may include extracting resonance parameters of the resonant impedance spectra. The resonance parameters are at least some of a frequency position (Fp) and magnitude (Zp) of a real part of the resonant impedance spectra, a resonant frequency (F1) and antiresonant frequency (F2) of an imaginary part of the resonant impedance spectra, an impedance magnitude (Z1) at the resonant frequency (F1) and an impedance magnitude (Z2) at the antiresonant frequency (F2), and a zero-reactance frequency (Fz) at the imaginary part of the resonant impedance spectra.

In an alternative embodiment, the resonant impedance spectra are analyzed to determine both water concentration and acid concentration in the fluid. Acid concentration of an oil is useful for estimating an amount of depletion of additives, an amount of acidic contamination, and/or an amount of fluid degradation. Some industrial fluids such as engine oil may have additives added to the fluids that are designed to increase the stability of the fluids in extreme temperature environments. The additives may be acidic compounds that elevate the acid concentration of the fluid. However, as the fluid ages, the additives deplete over time. The reduced amount of additives in the fluid reduces the acidity or acid concentration of the fluid. On the other hand, acidic contamination and fluid degradation may have the reverse effect of increasing the acid concentration of the fluid. Acidic contamination refers to external acidic components that are undesirably introduced into the fluid via leak paths through the reservoir housing that holds the fluid. For example, acidic components may be introduced into the fluid through a leak path with other external contaminants, such as water. As the amount of acidic contaminants increase, the acid concentration of the fluid increases and the performance or effectiveness of the fluid, such as for providing lubrication and/or heat dissipation, may decrease. The acids in the fluid may reduce the performance of the fluid and/or the machine in which the fluid is used by increasing the viscosity of the fluid and forming gums and resins.

Furthermore, the fluid may degrade over time as the fluid ages, such that the components of the fluid break up into smaller constituents. The rate of degradation may be affected by the high temperatures of the environment and/or the type and amount of additives and contaminants in the fluid. For example, the fluid may degrade at a higher rate once the stabilizing additives are depleted. The additives may include anti-oxidants, such that the fluid oxidizes at a greater rate once the additives are depleted. Typically, as the fluid degrades with age, the fluid may break down into corrosive acids or acidic components which increase the acid concentration of the fluid. The corrosive acids also reduce the performance of the fluid and can cause component failure (e.g., engine failure) if the fluid is not replaced by new fluid.

Monitoring the acid concentration of the fluid over time may be used to determine when to replace the fluid. For example, while a lubricating fluid that contains an acidic additive package is relatively new, the acid concentration of the fluid may gradually decrease over time as the acidic additives are gradually depleted. After the additives are depleted, the acid concentration may gradually increase due to at least one of acidic contaminants that leak into the fluid or fluid degradation. By monitoring the initial decrease and subsequent increase in the acid concentration, the sensing system can be used to predict the concentration of an additive package in the oil, when the additives are depleted, if there is a significant acid contamination, when the fluid should be replaced due to high acid concentration that exceeds a predetermined threshold level, and/or the like. For example, a low acid concentration may indicate that the concentration of the additive package is low or depleted. Based on the information provided by the sensing system, responsive actions may be taken to improve the fluid quality and/or increase the life of the fluid and/or machine in which the fluid is used. For example, additional additives may be added to the fluid responsive to the additives being depleted, the machine may be scheduled for repair and/or replacement responsive to detection of an acid contamination, and/or the fluid may be replaced responsive to determination of a high acid concentration that exceeds the predetermined threshold level.

Acidic components and water are both polar components. Conventional sensors, such as conventional capacitive sensors like the one described with reference to FIG. 52, are not able to discriminate between different polar components in a signal response to identify the individual contributions of water and acidic components in the fluid. However, the multivariable resonant sensor of the embodiments described herein is able to individually detect both water concentration and acid concentration of a non-polar fluid such as oil using only the single sensor.

Figure 64:
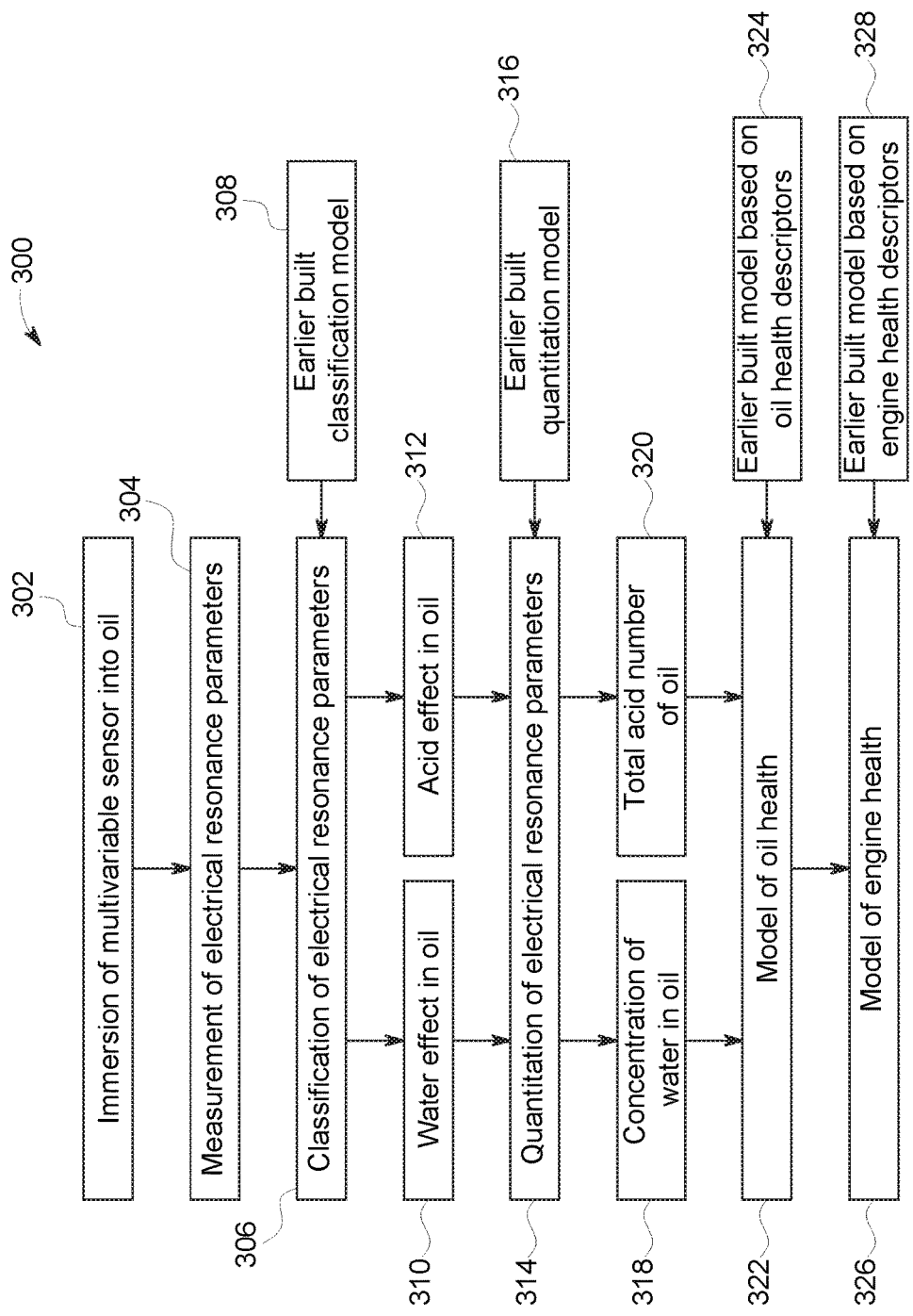
FIG. 64 is a flow diagram of a method for monitoring and assessing a lubricating oil according to another embodiment.

FIG. 64 is a flow diagram of a method 300 for monitoring and assessing a lubricating oil according to another embodiment. Although the method 300 is described with reference to a lubricating oil, the method 300 may be performed on a different industrial fluid other than a lubricating oil. The method 300 shown in FIG. 64 is a modified version of the method 2860 for monitoring oil health shown in FIG. 14. For example, the method 300 may be used to independently monitor a concentration of water in oil and a concentration of acid in oil (e.g., total acid number of oil), while the method 2860 is used to determine a concentration of water in oil, a concentration of fuel in oil, and a temperature of the oil.

At 302, a multivariable resonant sensor (e.g., the sensor 1714 shown in FIG. 2 and/or the sensor 5802 shown in FIG. 43) is immersed into oil. The oil may be used for lubricating a machine having moving parts, such as an engine. The sensor is immersed into the oil such that a sensing region of the sensor is in operational contact with the oil. The sensor includes electrodes and a sensing region circuit electrically connected to the electrodes. The sensor is configured to apply an electrical stimulus to the oil via the electrodes. The electrical stimulus may be generated by the sensing region circuit. The sensing region circuit in an embodiment includes one or more LCR resonant circuits. The electrical stimulus applied to the oil may include multiple electrical fields and/or multiple resonant frequencies. For example, in an embodiment, the sensing region circuit includes four LCR resonant circuits (or tuning elements shown in FIGS. 4 and 5) that have different resonant frequencies. The electrical stimulus has a spectral frequency range that includes the four resonant frequencies of the four LCR resonant circuits.

At 304, electrical resonance parameters are measured responsive to the application of the electrical stimulus to the oil. The electrical resonance parameters are measured by receiving an electrical signal from the sensor that is representative of a resonant impedance response or spectra of the sensing region of the sensor in operational contact with the oil. The electrical signal may be transmitted from the sensor to one or more processors, such as the one or more processors of the sensor reader 5804 shown in FIG. 43. The resonant impedance response shows the response of the sensing region in contact with the oil over the frequency range that includes the multiple resonant frequencies of the LCR resonant circuits. As described above, the resonance parameters for the resonant impedance spectra (e.g., $(f)=Z_{re}(f)+jZ_{im}(f)$) may include one or more of the frequency position $F_p$ and magnitude $Z_p$ of $Z_{re}(f)$, the resonant $F_1$ and antiresonant $F_2$ frequencies, the magnitudes $Z_1$ and $Z_2$ of $Z_{im}(f)$, and zero-reactance frequency $F_z$ of $Z_{im}(f)$. In an embodiment, at least four resonance parameters are extracted from the impedance response. The one or more processors are configured to analyze the resonance parameters to quantitatively determine (e.g., estimate) the concentrations of water and acid in the oil (as shown in steps 306, 308, 310, 312, 314, 316, 318, 320). The one or more processors optionally may also be configured to estimate a health of the oil and/or the machine in which the oil is used based on the concentrations of water and acid in the oil (as shown in steps 322 and 324). Furthermore, the one or more processors may be configured to predict a remaining life of the oil and/or the machine based on the concentrations of water and acid in the oil (as shown in steps 326 and 328).

At 306, the electrical resonance parameters are classified, which may be done using an earlier-built classification model at 308, to assess the water effects in the oil at 310 and the acid effect in the oil at 312. The classification model may be built using spectral resonant parameters of a control group that is accumulated from previously-determined analyses of the effects of water and acid on the same or a similar type of oil. At 314, the electrical resonance parameters may be quantified using an earlier-built quantitation model at 316, to independently determine a concentration of water in the oil at 318 and a concentration of acid in the oil (e.g., a total acid number of the oil) at 320.

In an embodiment, the analysis of the resonant impedance response may be performed by comparing the extracted resonance parameters from the measured resonant impedance response to known resonance parameters of a control group. The parameters in the control group may be recorded resonance parameters of the same or a similar type of oil at various controlled properties of the oil, such as at different specific concentrations of water in the oil and/or different specific concentrations of acid in the oil. For example, a first subset of the resonance parameters in the control group may be associated with the same type of oil having a negligible amount of water and a first concentration of acid; a second subset of the resonance parameters in the control group may be associated with the same type of oil having a first concentration of water and the first concentration of acid; and a third subset of the resonance parameters in the control group may be associated with the same type of oil having the first concentration of water and a negligible amount of acid. The data for the resonance parameters in the control group may be obtained via previous tests in the field and/or in the laboratory. The data for the previous tests may be stored and used to build the classification model and/or the quantitation model.

For example, a series of experiments may be performed using a single multivariable resonant sensor to determine the measured resonance parameters of a resonant impedance spectral response of the sensor in a given type of oil at various concentrations of water and acid of the oil. The concentrations of water and acid are variable that are modified across the series of experiments. The measured resonance parameters for the series of experiments may be plotted as data points on a graph, and may be used to develop the quantitative model that is used to predict the water concentration and the acid concentration of monitored oil. The quantitative model may be a transfer function. Thus, the measured or extracted resonance parameters from a resonance impedance spectral response may be input as variables into the quantitative model to predict water concentration and acid concentration of the tested oil.

In an embodiment, the properties of the oil that is monitored by the sensor may be determined by comparing the extracted resonance parameters from the measured impedance response to the resonance parameters in the control group that are associated with known properties of the oil (e.g., known water and acid concentrations). For example, the water concentration and the acid concentration in the oil may be determined by matching the extracted resonance parameters to a specific subset of resonance parameters in the control group. For example, if the extracted resonance parameters more closely match or align with the resonance parameters of the second subset of resonance parameters described above (relative to the matching or alignment with the resonance parameters of the first and third subsets), then the measured oil is determined to have the first concentration of water and the first concentration of acid. Statistical methods may be used to compare and match the measured resonance parameters to the control group of known resonance parameters. The statistical method used may be a regression analysis, such as a linear regression, a nonlinear regression, or the like. Although only three subsets of resonance parameters are mentioned above, the quantitation model may have more than three subsets in order to provide more accurate determinations of the water concentration and acid concentration in a sample of oil. For example, the one or more processors may be configured to determine the concentration of water in an oil at 10, 30, 50, or more different levels or concentrations, and may be configured to independently determine the concentration of acid within the same oil sample at 10, 30, 50, or more different levels or concentrations in order to provide an accurate determination of both properties.

At 322, the concentrations of water and acid in the oil may be used to generate or update a model of oil health, which may be based on an earlier-built model using oil health descriptors at 324. In general, a relatively high concentration of water and/or a relatively significant increase in the concentration of water in the oil may signal poor oil health. The significant increase in water concentration may indicate a leak condition that should be addressed. Furthermore, a relatively high concentration of acid and/or a relatively significant increase in the acid concentration may signal poor oil health, especially if the oil is not fresh or new. For example, if the oil is new, the high concentration of acid may be at least partially due to the presence of stabilizing additives added to the oil, such that the oil may be in good health. But, as the oil ages and the additives deplete, an increase in acid concentration may indicate the introduction of an acidic contaminant and/or degradation (e.g., oxidation) of the oil, indicating poor oil health. The oil health descriptors may include threshold levels or ranges of water and acid, and may also include threshold rates of change for the concentrations of water and acid. The oil may be considered to have good health if the determined concentrations of water and acid are both within the designated threshold levels. The oil health descriptors may include multiple thresholds for the water concentration and acid concentration. For example, if the acid concentration of the oil exceeds a first threshold, the model of oil health may indicate that the oil should be replaced within a designated period of time (or miles, revolutions, etc.) to avoid the oil degrading to a level of poor health that could damage the machine. Furthermore, if the acid concentration of the oil exceeds a second threshold that is greater than the first threshold, the model of oil health may indicate that the oil has a poor quality and should be replaced immediately without further operation of the machine until the oil is replaced and/or the machine is repaired (e.g., if a contamination leak is detected).

At 326, the concentrations of water and acid in the oil may be used to generate or update a model of the health of the engine (e.g., or another machine in which the oil is disposed), which may be based on an earlier-built model using engine health descriptors at 328. For example, if the engine is operated with a poor quality of oil, the health of the engine may suffer, reducing the expected performance and/or operational lifetime of the engine. On the other hand, if the oil in the engine is maintained in good health such that the oil is replaced before the oil degrades to a poor health condition, then the engine may be determined to have a good health. The health of the oil and the engine may be used to predict the remaining operational lifetimes of the oil and the engine using the models at steps 322 and 326.

Figure 65A:
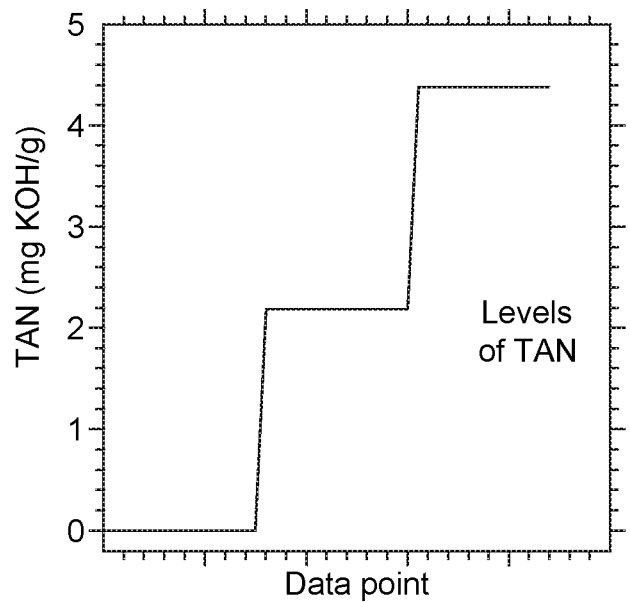
FIGS. 65A-B depict an experimental setup showing three different acid levels in a sample of locomotive engine oil and three different water levels in the sample of oil according to an embodiment.
Figure 65B:
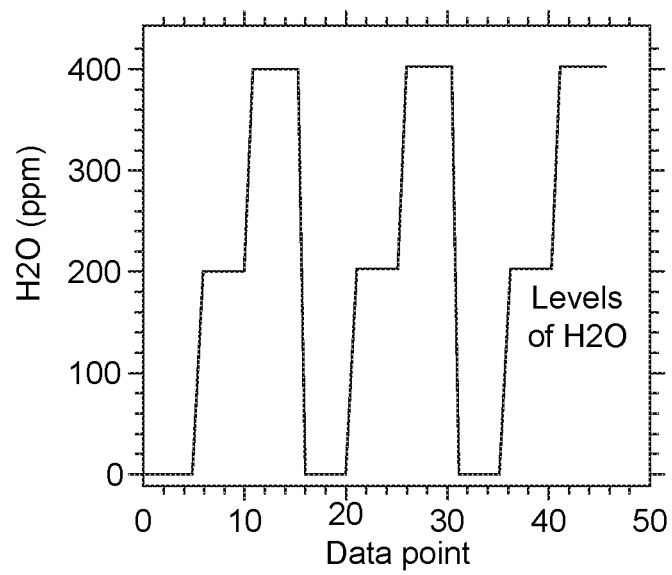

FIGS. 65A and 65B depict an experimental setup showing three different acid levels in a sample of locomotive engine oil and three different water levels in the sample of oil according to an embodiment. The experimental setup was tested to validate the detection of independent changes of two types of polar additives in oil (e.g., acid and water) using the multivariable resonant sensor described herein. The resonant sensor provides simultaneous measurements of at least two outputs. As shown in FIG. 65A, the different levels of total acid number (TAN) in the oil during the experiment were 0, 2, and 4 mg KOH/g, which was prepared using decanoic acid. As shown in FIG. 65B, the different levels of water in the oil were 0, 200, and 400 ppm. The goal of the testing was to resolve various TAN amounts at different levels of water in oil. As shown in FIGS. 65A and 65B, oil samples at each of the different levels of TAN were injected with different amounts of water such that nine different sample scenarios were tested.

Measurements of the resonance impedance of sensors were performed with a network analyzer under computer control using LabVIEW. The network analyzer was used to scan the frequencies over the range of interest and to collect the impedance response from the sensors. Collected impedance data was analyzed using KaleidaGraph (Synergy Software, Reading, Pa.) and PLS Toolbox (Eigenvector Research, Inc., Manson, Wash.) operated with Matlab (The Mathworks Inc., Natick, Mass.). The multivariable response of the resonant transducers originates from the measured whole resonance spectra of the transducer followed by the processing of these spectra using multivariate analysis tools. The resonance impedance spectra $(f)=Z_{re}(f)+jZ_{im}(f)$ of the resonant transducer were measured. Several parameters from the measured (f) spectra were calculated, including the frequency position $F_p$ and magnitude $Z_p$ of $Z_{re}(f)$ and the resonant $F_1$ and antiresonant $F_2$ frequencies, their impedance magnitudes $Z_1$ and $Z_2$ of $Z_{im}(f)$, and zero-reactance frequency $F_Z$ of $Z_{im}(f)$.

Figure 66:
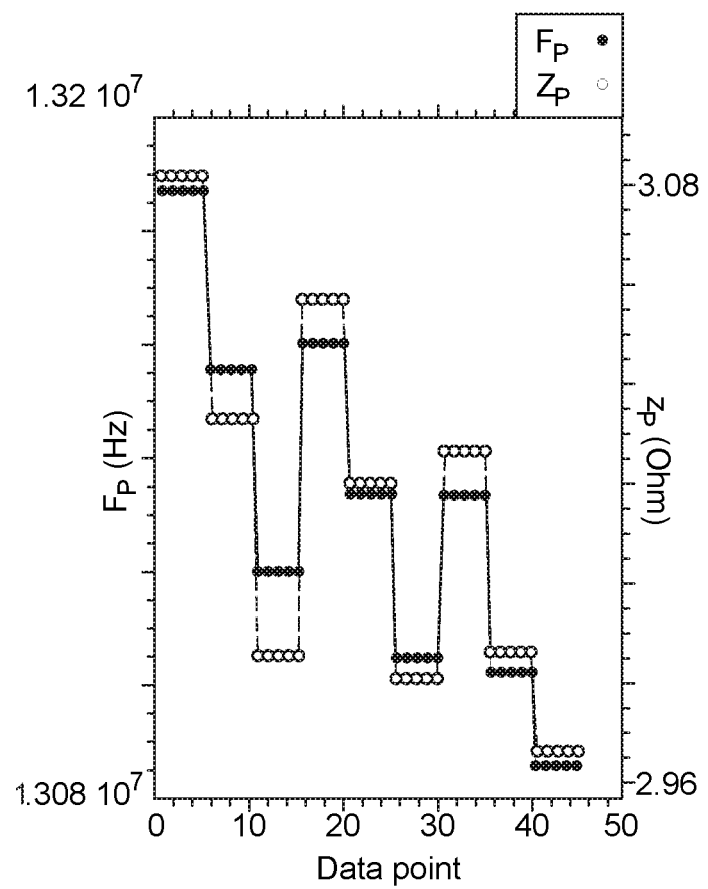
FIG. 66 plots the resonance parameters $F_p$ (in Hz) and $Z_p$ (in Ohm) of the measured impedance response of the oil samples to the electrical stimulus of the multivariable resonant sensor in the experiment described in FIGS. 65A-B.

FIG. 66 plots the resonance parameters $F_p$ (in Hz) and $Z_p$ (in Ohm) of the measured impedance response of the oil samples to the electrical stimulus of the multivariable resonant sensor in the experiment described in FIGS. 65A and 65B.

Figure 67:
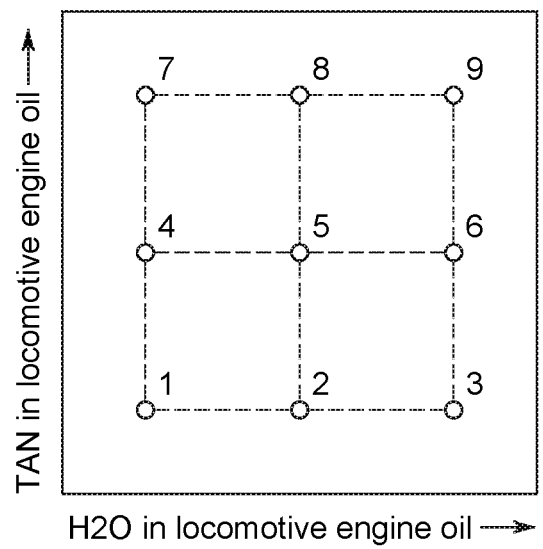
FIG. 67 depicts an experimental grid of nine samples with varying TAN and water levels in locomotive engine oil according to the experiment described in FIGS. 65A-B.

FIG. 67 depicts an experimental grid of nine samples with varying TAN and water levels in locomotive engine oil according to the experiment described in FIGS. 65A and 65B. For example, sample 1 represents the oil sample that includes 0 mg KOH/g TAN and 0 ppm water; sample 2 represents the oil sample including 0 mg KOH/g TAN and 200 ppm water; and sample 3 represents the oil sample including 0 mg KOH/g TAN and 400 ppm water. Samples 4-6 represent the oil samples including 2 mg/KOH/g TAN and 0, 200, and 400 ppm water, respectively. Samples 7-9 represent the oil samples including 4 mg/KOH/g TAN and 0, 200, and 400 ppm water, respectively.

Figure 68:
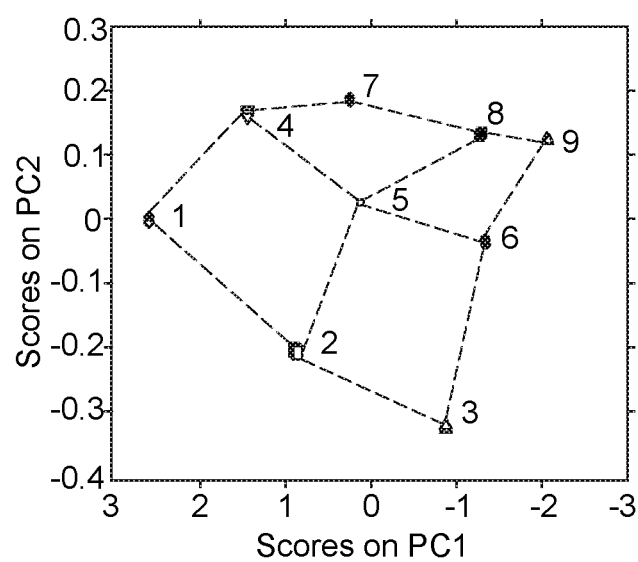
FIG. 68 depicts a scores plot of a developed PCA model illustrating spectral relation between sensor responses to the different types of contamination in the nine oil samples shown in FIG. 67.

FIG. 68 depicts a scores plot of a developed Principal Components Analysis (PCA) model showing Principal component 1 (PC1) vs. Principal component 2 (PC2) illustrating spectral relation between sensor responses to the different types of contamination in the nine oil samples of the locomotive engine oil shown in FIG. 67. As shown in FIG. 68, the experimental grid from FIG. 67 is visible in the scores plot, which indicates an ability to discriminate between all nine points of the experimental grid of samples using the PCA. For example, the experimental grid in FIG. 68 is a distorted version of the grid shown in FIG. 67, but all nine points are visible in the distorted view and have different coordinates in the scores plot.

Figure 69A:
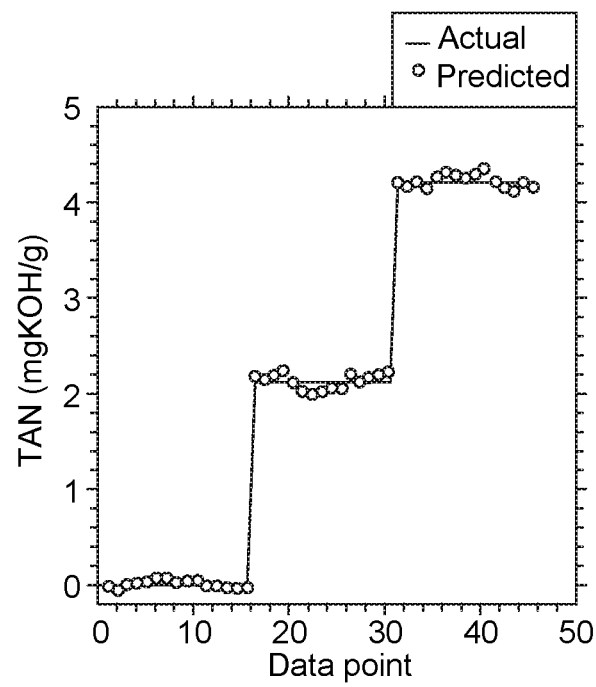
FIGS. 69A-B plot the results of predicted and actual TAN levels for the different samples in locomotive engine oil tested using the multivariable resonant sensor and the residual error of the TAN prediction, respectively.
Figure 69B:
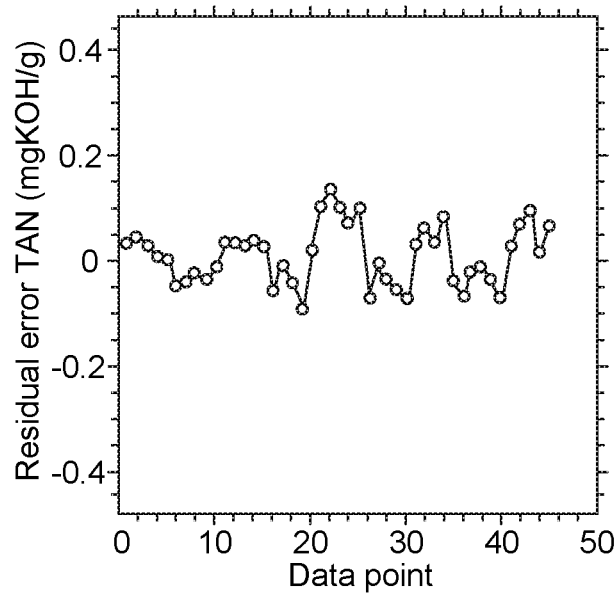

In the experimental methodology, the TAN and water levels were further determined or predicted using a multivariate regression technique. FIG. 69A plots the results of predicted and actual TAN levels for the different samples of oil tested using the multivariable resonant sensor. FIG. 69B plots the residual error of the TAN prediction using the multivariable resonant sensor. The results shown in FIGS. 69A and 69B illustrate that the multivariable sensor quantifies TAN in oil samples having different amounts of water therein with less than ±0.2 mgKOH/g residual error. Therefore, the multivariable resonant sensor is able to predict a TAN level (e.g., an acid concentration) in an oil sample, regardless of whether or not the oil sample includes a non-negligible concentration of water or other polar additives therein.

Figure 70A:
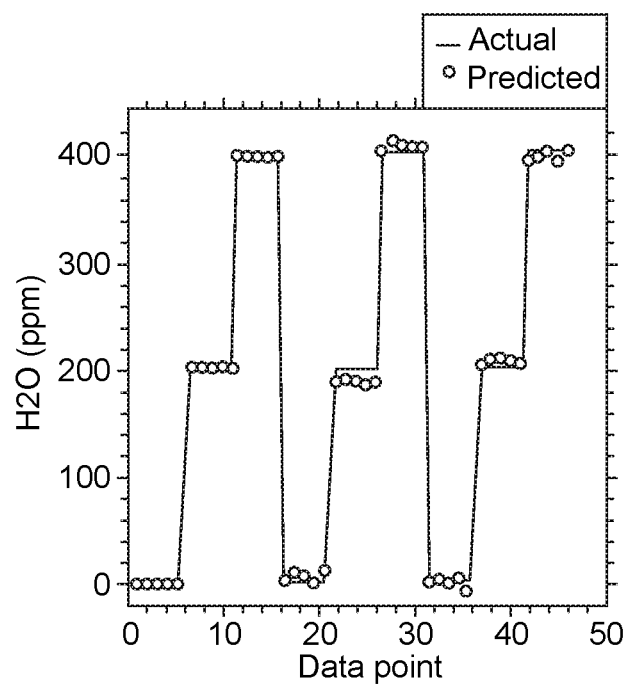
FIGS. 70A-B plot the results of predicted and actual water concentrations in oil for the different samples in locomotive engine oil tested using the multivariable resonant sensor and the residual error of the water concentration prediction, respectively.
Figure 70B:
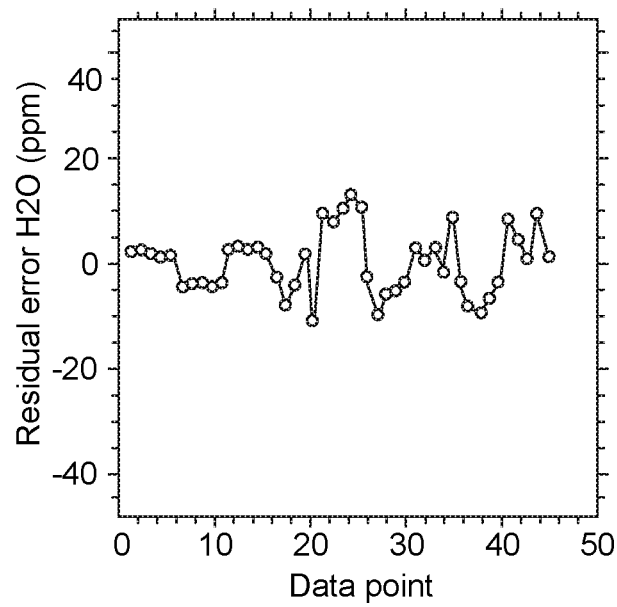

FIG. 70A shows the results of predicted and actual concentrations of water in oil for the different samples of oil tested using the multivariable resonant sensor at different TAN levels. FIG. 70B plots the residual error of the water concentration prediction using the multivariable resonant sensor. The results shown in FIGS. 70A and 70B illustrate that the multivariable sensor quantifies water concentrations in oil samples having different amounts of acid therein with less than ±20 ppm residual error. Therefore, the multivariable resonant sensor is able to predict a concentration of water in an oil sample, regardless of whether or not the oil sample includes a non-negligible concentration of acid or other polar additives therein. Furthermore, the single multivariable resonant sensor is able to predict both a water concentration and a TAN level of an oil sample based on a single spectral impedance response of the sensor in contact with the oil.

In another embodiment, the multivariable resonant sensor described herein is a component of an asset monitoring system that is configured to monitor a machine asset (e.g., an engine, a gearbox, a transmission, a turbocharger, and the like). The asset monitoring system may be configured to determine a health of the machine asset and may take responsive action, such as to provide an alert or automatically schedule maintenance, responsive to determining that the health of the machine asset, or an industrial fluid therein, is below a designated threshold health level. In one or more embodiments, the asset monitoring system may provide a prognostic outlook for the machine asset, such as by estimating a remaining operational lifetime of the machine asset and/or an industrial fluid therein.

Figure 71:
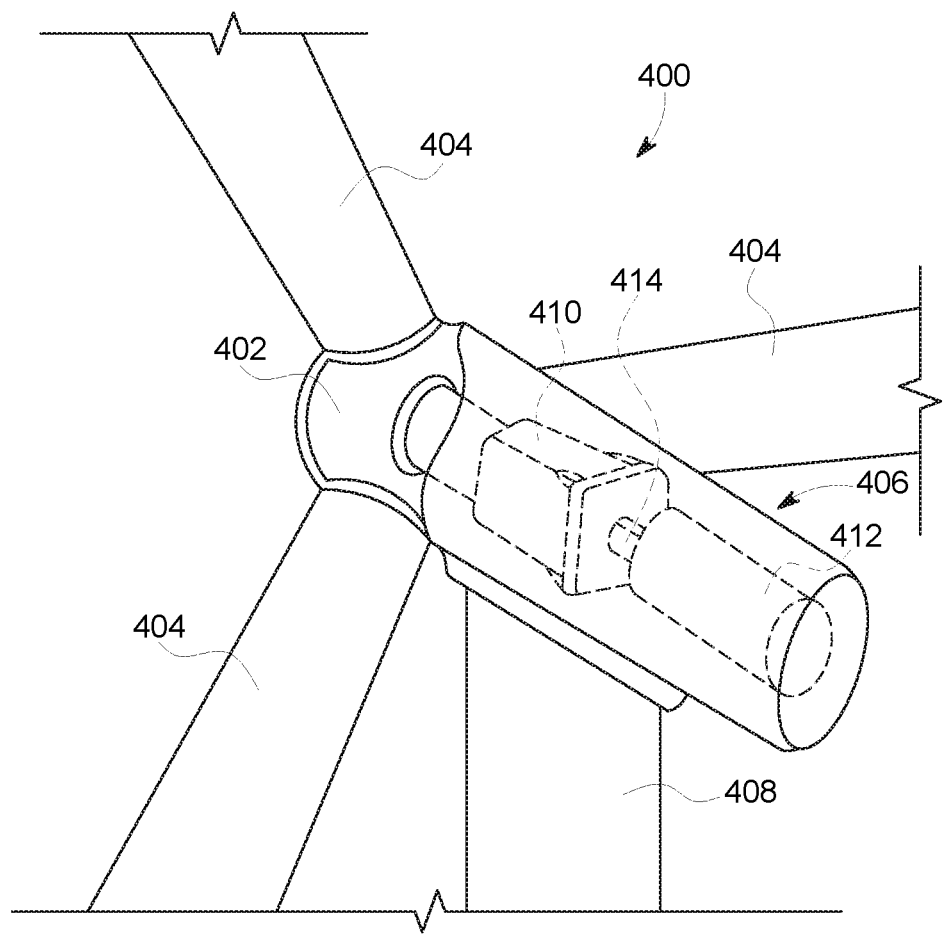
FIG. 71 is a perspective view of a portion of a portion of a rotor system according to an embodiment.

FIG. 71 is a perspective view of a portion of a rotor system 400 according to an embodiment. The rotor system 400 in the illustrated embodiment is a wind turbine or windmill, but in other embodiments the rotor system 400 may be a rotocraft (e.g., a helicopter, an airboat, etc.), a rotary-powered industrial machine, or the like. The rotor system 400 includes a hub 402 with three rotor blades 404 coupled thereto, a power conversion unit 406, and a base 408. The base 408 in the illustrated embodiment is a tower that holds the hub 402, rotor blades 404, and power conversion unit 406 suspended above the ground. The power conversion unit 406 includes a gearbox 410 and a generator 412. The gearbox 410 is mechanically coupled to the hub 402, such that rotational movement of the hub 402 rotates gears within the gearbox 410. The gearbox 410 is mechanically coupled to the generator 412 via a shaft 414. The gearbox 410 rotates the shaft 414, and the generator 412 converts the mechanical energy of the rotating shaft 414 into electrical energy. The electrical energy may be stored in a battery (not shown) within the rotor system 400 and/or transmitted via a conductive power cable (not shown) along the base 408 to a power load or energy storage device remote from the rotor system 400. The gearbox 410 is disposed between the hub 402 and the generator 412, and is configured to control a speed of rotation of the shaft 414 relative to a speed of rotation of the hub 402. Typically, the generator 412 is configured to operate at higher rotational speeds than the hub 402, so the gearbox 410 increases the speed of rotation from the hub 402 to the shaft 414, but the gearbox 410 optionally may be configured to decrease or maintain the speed of rotation instead of increasing the speed of rotation.

Typical oils for gearboxes are synthetic oils such as hydrocarbon oils, polyglycol oils, ester oils, polyalphaolefin oils, and other oils. Oils for gearboxes of wind turbines include polyalphaolefin oils, polyglycol oils, and other oils. For high performance, the synthetic base oil stock is used as the main component and is blended with additives for protection against temperature effects, acid formation, oxidation, and long term wear. Mechanisms of oil aging include depletion of additives and build-up of external contaminants. Examples of external contaminants include molecular contaminants such as water and particulate contaminants such as wear particles. Emulsified and dissolved water in oil induce damage to gearbox components and reduced protection normally provided by lubricating oil. Water in the air within the headspace inside the gearbox accelerates corrosion of gearbox components. High levels of TAN drive the corrosion of seals and hoses of gearbox components. Thus, real-time monitoring of oil health provides the ability to eliminate asset downtime for repair and replacement, and unnecessary premature oil changes.

The gearbox 410 and the generator 412 are machine assets (also referred to herein as assets) of the rotor system 400. The assets of the rotor system 400 may include industrial fluids for lubrication, heat-dissipation, pneumatics, or the like. For example, the gearbox 410 includes oil housed within a reservoir. The oil engages the gears to provide lubrication, reducing the frictional forces between the gears and providing improved efficiency (relative to gearboxes without lubricating fluids). However, as described above, the health of oil may diminish over time due to oil aging and/or the introduction of external contaminants, such as water and acidic components. As the health of the oil declines, not only does the lubricating performance of the oil suffer (e.g., due to oil contamination and aging), but so too may the health of the asset that uses the oil (e.g., the gearbox 410). For example, contaminants such as acids and water may cause, or at least exacerbate, corrosion of the walls of the gearbox 410 that contain the oil. The water and acid may increase the rate of oxidation of the metallic walls of the gearbox 410. The corrosion may result in cracks that allow additional contaminants into the gearbox 410. Eventually, the corrosion may cause the gearbox 410 to operationally fail (e.g., the gears jam or become displaced), which can cause the rotor system to shut down until a replacement gearbox can be installed. The failure of the gearbox 410 due to corrosion may cause damage to other assets and/or components of the rotor system 400, such as the generator 412, increasing the cost of the repairs and possibly extending the down-time of the rotor system 400.

The external contaminant in the oil of the gearbox 410 may be water that enters the oil reservoir from the ambient environment due to condensation. For example, the gearbox 410 may not be hermetically sealed, and leak paths in the gearbox 410 may allow contaminants such as water from the ambient environment to interact with the oil. Besides condensation, water may be introduced into the oil via a coolant leak, equipment cleaning, or as a by-product of a reaction. The amount of water in the oil may vary based on multiple factors including the amount and size of the leak paths (e.g., the accessibility of the oil), the temperature of the oil, and the temperature and relative humidity of the ambient environment. For example, while the rotor system 400 operates, the temperature of the oil may exceed the temperature of the ambient environment and/or an evaporation temperature of water. At least some of the water within the oil may evaporate into the ambient environment, reducing the concentration of water within the oil. Conversely, when the temperature of the oil is less than the evaporation temperature of water, the concentration of water within the oil may increase due to condensation of water from the ambient environment into the oil. The condensation of water into the oil may typically occur when the rotor system is in a non-operating state, as the temperature of the oil decreases relative to the temperature of the oil while the rotor system is in an operating state. In order to avoid the costs associated with reduced performance of the rotor system 400, repairs, shut-downs, and/or reduced operating lifetimes of assets such as the gearbox 410, an asset monitoring system 500 (shown in FIG. 73) is configured to provide real-time monitoring of the health of the lubricating oil in an asset, such as the gearbox 410, and the asset itself.

Figure 72:
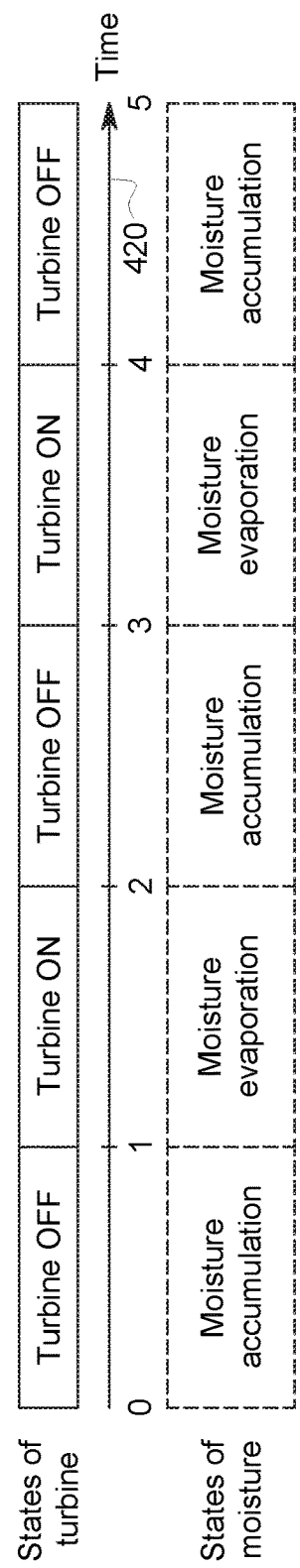
FIG. 72 is a schematic diagram showing a relationship between operating state of the rotor system and a change in water concentration within the oil of the rotor system over time.

FIG. 72 is a schematic diagram showing a relationship between operating state of the rotor system 400 (also referred to as turbine or wind turbine) and a change in water concentration within the oil of the rotor system 400 over time. FIG. 72 plots the state of the turbine and the state of moisture (e.g., water) in the oil along an axis 420 representing time in relative units. During a first time period between times 0 and 1, the turbine is in an OFF or non-operating state. For example, in the non-operating state the rotors 404 and hub 402 shown in FIG. 71 are not rotating, or alternatively are rotating but the gearbox 410 and/or generator 412 are mechanically or electrically disconnected from the hub 402 such that electrical energy is not produced from the rotation of the rotors 404 and hub 402. As shown in FIG. 72, moisture accumulates in the oil between times 0 and 1 (where time is in relative units) while the turbine is in the OFF state. The moisture may accumulate due to condensation from the ambient environment while the temperature of the oil is relatively low. In the subsequent time period between times 1 and 2, the turbine is in an ON or operating state, such that the rotors 404 and the hub 402 rotate and the generator 412 converts the mechanical rotational energy into electrical energy for storage and/or powering a load or a power grid. While the turbine is ON between times 1 and 2, the moisture evaporates from the oil into the ambient environment due to the high temperature of the oil. The diagram in FIG. 72 illustrates a general trend that a concentration of water in the oil of the gearbox 410 increases or accumulates while the turbine 400 is OFF and the concentration of water in the oil decreases via evaporation while the turbine 400 is ON. The rates of water accumulation and/or reduction may change over time based on various factors such as temperature of the oil, temperature and relative humidity of the ambient environment, existing concentration of water in the gearbox 410, size and/or amount of leak paths in the gearbox 410, and the like. For example, if the turbine 400 operates for a sufficient duration and at a sufficient temperature, most if not all of the water may evaporate from the oil such that the rate of moisture evaporation may effectively stop due to the lack of moisture in the oil, although the turbine 400 continues to operate in the ON state.

Since water may accumulate in the oil while the turbine 400 is OFF and evaporates from the oil while the turbine 400 is ON, the concentration of water in oil while the turbine 400 is OFF may be greater than the concentration of water while the turbine 400 is ON. As a result, the corrosive effect of water in the gearbox 410 may be more severe during the periods of time that the turbine 400 is OFF relative to when the turbine 400 is ON and operating. For example, a greater concentration of water in the oil and/or a greater amount of time that the turbine 400 is OFF cause an increased amount of corrosion or degradation of the gearbox 410 relative to a reduced concentration of water in the oil and/or a reduced amount of time that the turbine 400 is OFF. Therefore, the health of the oil and/or the gearbox 410 may be preserved by reducing the amount of water that is introduced into the oil and/or reducing the amount of time that the turbine 400 is OFF, such as by operating the turbine 400 in the ON state for longer durations of time. The asset monitoring system 500 (shown in FIG. 73) is configured to continuously (e.g., at set time intervals) monitor the operating states of the turbine 400 and the concentration of one or more polar analytes, such as water, in the oil to determine the health of the oil and the gearbox 410.

Figure 73:
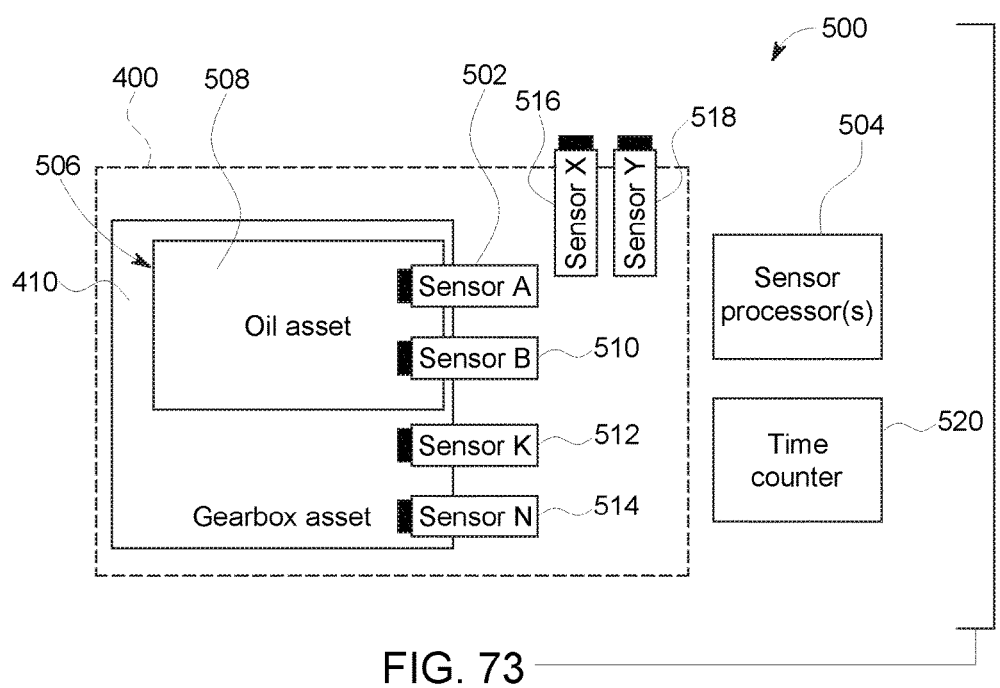
FIG. 73 is a schematic diagram of an asset monitoring system according to an embodiment.

FIG. 73 is a schematic diagram of an asset monitoring system 500 according to an embodiment. The asset monitoring system 500 includes at least a resonant sensor 502 (e.g., Sensor A shown in FIG. 73) and one or more sensor processors 504 operatively connected to the resonant sensor 502. The asset monitoring system 500 is configured to monitor an asset of the rotor system 400, which in the illustrated embodiment is the gearbox 410. The gearbox 410 defines a reservoir 506 that contains a lubricating oil 508 for lubricating the various gears and other moving components of the gearbox 410. The resonant sensor 502 is mounted to the gearbox 410 in operational contact with the oil 508. The asset monitoring system 500 is configured to provide real-time monitoring of the health of the oil 508 and the gearbox 410. The asset monitoring system 500 may be configured to use the determined health of the oil 508 and/or the gearbox 410 to predict a remaining operational life of the oil 508 and/or the gearbox 410. Furthermore, the asset monitoring system 500 may be configured to take responsive actions based on the determined health of the oil 508 and/or the gearbox 410, such as automatically scheduling maintenance, providing an alert or message to an operator representative of the health status, and/or prohibiting operation of the rotor system 400 until maintenance is performed.

One or more technical effects of the asset monitoring system 500 is the ability to provide maintenance on an asset based on a health or condition of the asset, such that the maintenance is performed when necessary. The asset monitoring system 500 is configured to avoid problems associated with monitoring the asset only on a fixed schedule, such as every twelve months, every six months, or every three months. For example, such maintenance may require an operator manually accessing the gearbox to inspect the health of the oil and the gearbox. If the oil and gearbox are determined to be in good health during an inspection, the effort and cost of manually inspecting the gearbox are unnecessary. On the other hand, leaks can quickly cause damage to the gearbox and the oil therein, and the fixed maintenance schedule may not be able detect a poor health condition of the oil and/or the gearbox in time to prevent reduced performance of the rotor system and/or damage to the rotor system. The asset monitoring system 500 is configured to continuously monitor the health of the oil and/or the gearbox, such as by obtaining a measurement every second, every minute, every hour, every day, or any other predetermined time interval. By estimating the remaining operational life of the oil and/or gearbox, the asset monitoring system 500 allows an operator to plan for future maintenance, such as by ordering replacement parts and scheduling a maintenance appointment, before such maintenance is necessary. Furthermore, by taking an automatic responsive action upon detecting a poor health of the oil and/or gearbox (instead of waiting until regularly-scheduled maintenance), the asset monitoring system 500 is configured to reduce damage to the gearbox which extends the operational lifetime of the gearbox and/or other components of the rotor system. Therefore, the condition-based maintenance provided by the asset monitoring system 500 provides the ability to operate the wind turbine more reliably and to avoid costly shut-downs and repairs.

The resonant sensor 502 is configured to measure a concentration of at least one polar analyte in the oil 508. The resonant sensor 502 may be the same or at least similar to the sensor 5802 shown and described in FIG. 43. For example, the sensor 502 has a sensing region circuit that includes at least one LCR resonant circuit, and optionally includes multiple LCR resonant circuits having different resonant frequencies relative to each other. The sensing region circuit is configured to generate an electrical stimulus that is applied to the oil via electrodes of the sensor 502. The electrical stimulus applied to the oil is generated over a spectral frequency range that includes or incorporates the resonant frequencies of the resonant LCR circuits. The sensor 502 generates the electrical stimulus having multiple different frequencies in order to obtain a measurement of one or more polar analytes in the oil.

The sensor 502 is communicatively connected to the one or more sensor processors 504. For example, the sensor 502 may be wirelessly connected to the one or more sensor processors 504, such as via inductive coupling, or may be conductively connected to the one or more sensor processors 504, such as via a wired connection. The one or more sensor processors 504 may be components of the sensor reader 5804 shown in FIG. 43 and/or the reader 2659B shown in FIGS. 11 and 12. Although shown in FIG. 73 as one discrete component or device, the one or more sensor processors 504 may include multiple processors that are distributed in different devices or housings. For example, one processor 504 may be disposed in a sensor reader proximate to the sensor 502, and another processor 504 of the sensor processors 504 may be disposed remotely, such as in a remote server that is not disposed on the rotor system 400.

The sensor 502 is configured to transmit an electrical signal to the one or more processors 504. The electrical signal is representative of an impedance response of the sensor 502, in contact with the oil, to the electrical stimulus. The impedance response is measured over the resonant frequencies of a single or multiple LCR resonant circuits of the sensor 502. As described above (e.g., with reference to FIGS. 8, 14, 63, 64, etc.), the one or more sensor processors 504 are configured to receive the electrical signal from the resonant sensor 502 and analyze the impedance response to determine a concentration of the polar analyte in the oil. The one or more sensor processors 504 may analyze the impedance response by extracting (e.g., calculating) resonance parameters from the impedance response, such as Fp, Zp, F1, F2, Z1, Z2, and/or Fz.

The one or more polar analytes that are measured by the sensor 502 are at least one of an oil-aging compound or an external contaminant. Examples of oil-aging compounds may include stabilizing additives added to the oil and acidic components that are produced during the chemical breakdown of the oil and/or the stabilizing additives added to the oil. Examples of external contaminants include water, acids, metallic particles, and the like that enter the reservoir 506 via leak paths in the gearbox 410 or generated within the gearbox 410. As described above with reference to FIGS. 64-70B, each measurement of the impedance response of the oil to an electrical stimulus pulse may be used to determine a concentration of water and/or a concentration of acid (e.g., total acid number) in the oil. Therefore, the sensor 502 can be used to determine a measurement of the concentration of water, the concentration of acid, or both based on the impedance response to an electrical stimulus. In one embodiment, the sensor 502 and processors 504 may monitor the water concentration only, and in another embodiment the sensor 502 and processors 504 may monitor the water concentration and the acid concentration or just the acid concentration.

The sensor 502 and one or more processors 504 are configured to monitor the concentration of the one or more polar analytes of interest in the oil over time by obtaining multiple different measurements of the concentration at different times. For example, in an embodiment, the sensor 502 and the one or more processors 504 may periodically measure the concentration of a selected polar analyte in order to track changes of the concentration of the selected polar analyte over time. For example, the sensor 502 and one or more processors 504 may obtain a measurement of the concentration at regular intervals that are no greater than five minutes in duration (between measurements). The concentration of the selected polar analyte may be measured every two minutes, every minute, every thirty seconds, every ten seconds, every second, or the like. The concentration of the polar analyte is measured periodically by the sensor 502 applying an electrical stimulus having multiple different frequencies to the oil at a regular time interval. The one or more processors 504 are configured to analyze the impedance response of the oil (e.g., the sensor in contact with the oil) to each application of the electrical stimulus to determine the concentration of the polar analyte at multiple different times. For example, a first determined concentration of the polar analyte is associated with a first time that the sensor 502 applies a first electrical stimulus to the oil, and a second determined concentration of the polar analyte is associated with a second time (e.g., such as thirty seconds after the first time) that the sensor 502 applies a second electrical stimulus to the oil. The relatively high frequency of measurements, compared to monthly or bi-yearly measurements for example, allows the asset monitoring system 500 to provide early detection of, and remedial responses to, contaminant leaks, poor oil health and/or gearbox health, and the like. By obtaining measurements of the concentration of the one or more selected polar analytes in the oil at multiple different times, the asset monitoring system 500 can monitor and track how the concentration changes during an operational life of the gearbox.

The asset monitoring system 500 optionally may include one or more additional sensors configured to monitor various properties of the oil, the rotor system, and/or the ambient environment. For example, in the illustrated embodiment, the asset monitoring system 500 includes a temperature sensor 510 (e.g., Sensor B) that is mounted to the gearbox 410 and/or disposed within the reservoir 506. The temperature sensor 510 is in operational contact with the oil 508 and is configured to monitor a temperature of the oil 508 over time. For example, the temperature sensor 510 may measure the temperature of the oil 508 periodically, such as every second, every ten seconds, every thirty seconds, every minute, or the like. The temperature sensor 510 optionally may measure the temperature of the oil 508 with the same or similar periodicity as the resonant sensor 502. In one embodiment, the temperature sensor 510 may be a part of the sensor 502 and share the same housing and communication components with the sensor 502.

As shown in FIG. 73, the asset monitoring system 500 further includes additional sensors that are configured to monitor relevant properties of the oil 508, the gearbox 410, and the ambient environment. For example, the asset monitoring system 500 may include a temperature sensor 512 (e.g., Sensor K) and a vibration sensor 514 (e.g., Sensor N) mounted to the gearbox 410. The temperature sensor 512 is configured to monitor a temperature of the gearbox 410. The temperature sensors disclosed herein may be thermocouples, resistive temperature devices, infrared sensors, bimetallic devices, silicon diodes, thermometers, change of state sensors, or the like. The vibration sensor 514 is configured to monitor vibration of the gearbox 410 and/or the rotor system 400. The vibration sensor 514 may be or include an accelerometer, a piezoelectric component, a piezoresistive component, a variable capacitance component, and/or a servo sensor.

The asset monitoring system 500 may also include a temperature sensor 516 (e.g., Sensor X) and a humidity sensor 518 (e.g., Sensor Y) mounted to the rotor system 400 remote from the gearbox 410. The temperature sensor 516 is configured to monitor a temperature of the ambient environment, and the humidity sensor 518 monitors the relative and/or absolute humidity of the ambient environment. The humidity sensor 518 may be a capacitive-based electronic hygrometer, a resistive-based electronic hygrometer, or the like. All of the sensors 502, 510, 512, 514, 516, 518 of the asset monitoring system 500 are communicatively coupled to the one or more sensor processors 504 via a wireless or wired connection. For example, the sensors 502, 510, 512, 514, 516, 518 are configured to obtain measurements of the corresponding properties and transmit the measurements in the form of electrical signals having data parameters to the one or more sensor processors 504 for data collection and analysis. The sensors 510, 512, 514, 516, 518, other than the resonant sensor 502, may be optional. In other embodiments, the asset monitoring system 500 may have greater or less than the six sensors shown in FIG. 73, and/or may include at least one different type of sensor than the types of sensors described, such as an optical sensor, an electromagnetic sensor (e.g., a Hall effect sensor), or the like.

Some of the sensors of the asset monitoring system 500 may be configured to monitor properties that are used to determine the operating state of the rotor system 400. For example, the temperature sensor 510 in the oil 508, the temperature sensor 512 on the gearbox 410, and the vibration sensor 514 may be used by the sensor processor(s) 504 to monitor whether the rotor system 400 is in the ON (or operating) state or the OFF (or non-operating) state. Such sensors 510, 512, 514 are referred to herein as operating condition sensors, as the sensors 510, 512, 514 are used to detect when the rotor system 400 is in the operating state and when the rotor system 400 is in the non-operating state. For example, if the vibration sensor 514 detects that the gearbox 410 is vibrating at an amount, characterized as a frequency or intensity, that exceeds a corresponding vibration threshold, the one or more sensor processors 504 may determine that the rotor system 400 is in the operating state because operation of the rotor system 400 may cause vibration due to the moving components. Conversely, if the vibration sensor 514 detects that the vibration of the gearbox 410 is below the vibration threshold, then the rotor system 400 may be determined to be in the non-operating state.

In another example, if at least one of the temperature of the oil 508 or the temperature of the gearbox 410 exceeds a corresponding threshold temperature, the one or more sensor processors 504 may determine that the rotor system 400 is in the operating state because operation of the rotor system 400 generally heats the gearbox 410 and the oil 508 therein. Conversely, detection of the temperature of the oil 508 or the temperature of the gearbox 410 falling below the corresponding threshold temperature may indicate that the rotor system 400 is in the non-operating state because the gearbox 410 and the oil 508 therein may generally cool down responsive to the rotor system 400 shutting down. Optionally, the corresponding threshold temperatures may vary dependent on the temperature of the ambient environment as detected by the temperature sensor 516. For example, the one or more sensor processors 504 may analyze the temperature difference between the ambient environment and the oil 508 and/or the gearbox 410. For example, if the ambient environment is hotter than an average or median temperature, then the corresponding threshold temperature may be raised to account for the temperature change of the oil 508 and/or gearbox 410 attributable to the ambient environment. Furthermore, if the ambient environment is colder than the average or median temperature, then the corresponding threshold temperature may be lowered.

In other embodiments, additional or different sensors may be used to determine and monitor the operating state of the rotor system 400, such as an optical sensor, an electromagnetic sensor, an angular rotation sensor, or the like. The asset monitoring system 500 may be configured to continuously monitor the operating state of the rotor system 400 over time to determine durations of time periods that the rotor system 400 is ON, durations of time periods that the rotor system 400 is OFF, the frequency at which the rotor system 400 switches operating states, and the like. In an embodiment, the asset monitoring system 500 includes a time counter 520 that is configured to keep a record of time. The one or more processors 504 are configured to determine the durations in each of the ON and OFF operating states and the frequency of switching based on received parameters from the operating condition sensors and the time counter 520. Although the time counter 520 is shown in FIG. 73 as a separate and discrete component or device relative to the sensor processor(s) 504, the time counter 520 optionally may be an integral component of the one or more sensor processors 504. For example, at least one of the one or more processors 504 and the time counter 520 may be contained within a same computer or server. As described with reference to FIG. 72, different processes occur while the rotor system 400 is in the ON state relative to when the rotor system 400 is in the OFF state, such as water condensation and accumulation in the oil while the rotor system 400 is in the OFF state. Therefore, the information about the times, durations, and frequency that the rotor system 400 is in the OFF state may be used to determine the health of the oil 508 and the gearbox 410, because the corrosion of the gearbox 410 due to water may be more severe when the rotor system 400 is in the OFF state due to the higher water concentration.

Figure 74:
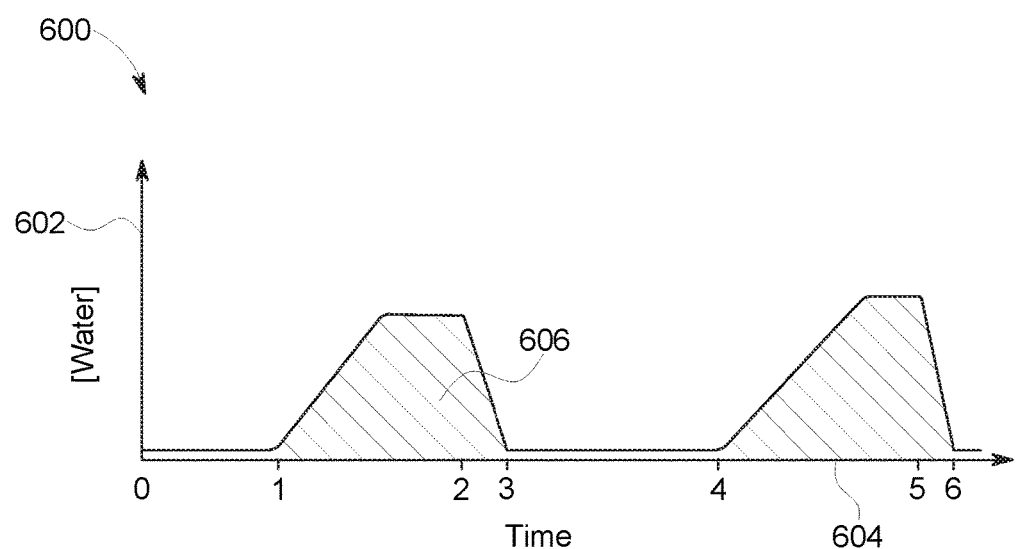
FIG. 74 is a plot of a concentration of water in oil over time according to an embodiment.

FIG. 74 is a plot 600 of a concentration of water in oil over time according to an embodiment. The y-axis 602 represents the concentration of water in oil, which may be in parts per million or the like. The x-axis 604 represents time. The duration of the x-axis 604 from times 0 to 6 may be days, weeks, months, or years. The time values 1 to 6 shown in FIG. 74 are not representative of regular, uniform time intervals, such that the time between times 1 and 2 is greater than the time between times 2 and 3. The oil may be the oil 508 within the gearbox 410 of the rotor system 400 shown in FIG. 73. In an embodiment, water is a polar analyte that is measured by the resonant sensor 502 and one or more sensor processors 504 shown in FIG. 73. The resonant sensor 502 and the one or more processors 504 are configured to measure the concentration of water within the oil at multiple times during the operational life of the gearbox (e.g., by applying an electrical stimulus to the oil at different times and analyzing the resonant impedance spectral responses to the electrical stimuli). The resonant sensor 502 and the one or more processors 504 may measure the concentration of water within the oil periodically at a regular interval, such that the data obtained can be plotted as shown in FIG. 74.

As shown in FIG. 74, between times 0 and 1, the concentration of water is at a negligible amount, such that no water or only a residual amount of water is present in the oil. The time period between times 0 and 1 may represent a time period that the rotor system is in the operating (e.g., ON) state. For example, while the rotor system operates, the temperature of the oil may be sufficiently high that water from the ambient environment does not condense into the oil and water previously within the oil evaporates, resulting in a negligible amount of water. Between times 1 and 2, the concentration of water increases to a non-negligible amount. For example, the concentration of water increases and then generally levels off. The time period between times 1 and 2 may represent a time period that the rotor system is in the non-operating (e.g., OFF) state. For example, after the rotor system shuts down, the temperature in the oil may decrease towards the temperature of the ambient environment. As described with reference to FIG. 72, when the temperature of the oil is sufficiently low, water from the ambient environment may accumulate in the oil due to condensation and other known factors, causing the illustrated increase in the concentration of water. The concentration of water may level off due to various factors, such as the humidity of the ambient environment, the temperature of ambient environment, the temperature of the oil, and properties of the oil such as water solubility of the oil.

Between times 2 and 4, the concentration of water in the oil decreases until the concentration of water is at a negligible amount from time 3 to time 4. The time period between times 2 and 4 may represent another time period that the rotor system is operating. In an initial period between times 2 and 3, the concentration of water in the oil decreases, which may be attributable to an increased temperature of the oil as the rotor system warms up and operates. The time period between times 2 and 3 may include a warm-up period of the rotor system. For example, as the oil heats up, the temperature of the oil may exceed an evaporation threshold temperature, causing the water in the oil to evaporate into the ambient environment or the headspace of the gearbox. Between times 3 and 4, most if not all of the water in the oil at time 2 has evaporated. Between times 4 and 5, the concentration of water in the oil increases again due to the rotor system switching back to the non-operating state. The rotor system may switch to the non-operating state based on weather conditions, such that the rotor system may be switched OFF responsive to severe weather or a lack of wind. Optionally, the rotor system additionally or alternatively be switched OFF responsive to a lack of a need for electrical power, such as if an electrical grid does not need the rotor system to generate electrical power. Furthermore, the rotor system may be switched OFF due to maintenance or other scheduled tasks. At time 5, the rotor system may be switched ON again, which causes the resulting decrease in the concentration of water shown in the plot 600 after time 5.

A high concentration of water in the oil of the gearbox generally reduces the health of the gearbox and the oil relative to a negligible amount of water in the oil. For example, the water causes corrosion of the gearbox and also increases oxidation and breakdown of various components in the oil, such as stabilizing additives. As shown in FIG. 74, the time periods in which the rotor system is OFF, such as between times 1 and 2 and between times 4 and 5, have a higher concentration of water relative to the time periods that the rotor system is ON, such as between times 0 and 1, 2 and 4, and after time 5. Therefore, the health of the oil and the health of the gearbox deteriorate more, due to water in the oil, when the rotor system is OFF than when the rotor system is ON.

In one or more embodiments, the one or more sensor processors 504 (shown in FIG. 73) are configured to calculate a degradation value for the gearbox based on the concentration of one or more polar analytes of interest in the oil as a function of time. The degradation value represents a level of asset degradation. The degradation value is inversely proportional to the health and remaining life of the asset, such as the gearbox and/or the oil within the gearbox. For example, a low degradation value may represent a relatively healthy oil and/or gearbox with a long remaining life, and a high degradation value represents a relatively unhealthy oil and/or gearbox with a short remaining life. The remaining life represents an estimated amount of time before the asset should be replaced or repaired to avoid causing poor performance of the rotor system and/or damage to other components of the rotor system. The degradation value typically increases over time as the asset ages and the quality or health of the asset decreases. Optionally, the one or more processors 504 may calculate a degradation value of the oil and a separate degradation value of the gearbox. For example, an oil change in the gearbox may trigger a reset of the degradation value of the oil without resetting the degradation value of the gearbox.

The degradation value is calculated based on the concentration of the polar analyte in oil over time during the operating life of the asset. For example, in embodiments in which water is the polar analyte of interest, the degradation value may be calculated as the product of the water concentration and the duration of time. Since the concentration of water in the oil fluctuates over time due to condensation, evaporation, and the like, the degradation value may be calculated as the integral of the water concentration over time during the life of the asset. The integral is calculated to determine the area under the curve 606 shown in the plot 600 of FIG. 74. Since the water concentration may be measured periodically by the resonant sensor, the one or more processors may integrate using the trapezoidal rule to approximate the area under the curve 606 using the periodic measurements of water concentration in the oil. The degradation value of an asset can only increase or stay the same over time, such that the degradation value of the asset at time 5 is greater than the degradation value of the same asset earlier in time, such as at time 4.

The degradation value is proportional to the concentration of water, so the degradation value increases when there is a non-negligible water concentration, which usually occurs when the rotor system is non-operating and the temperature of the oil is relatively cool. Due to the trend between water concentration in oil and operating state of the rotor system, in an embodiment, the degradation value may be calculated based on the concentration of water in the oil during the time periods that the rotor system is in the non-operating state. For example, the degradation value may be calculated as the integral of the concentration of water between times 1 and 2 and between times 4 and 5. The times that the rotor system switches between operating states, such as at time 1 and at time 2, may be determined based on one or more of the operating condition sensors of the rotor system, such as the vibration sensor 514, the temperature sensors 510, 512, or the like. In an alternative embodiment, the one or more sensor processors 504 may calculate the degradation value of the asset based on the entire duration from times 0 to 6 shown in FIG. 74, such as by calculating the integral of the concentration of water over the entire time period from 0 to 6. By including the entire duration in the calculation, some intermediate time periods in which the rotor system is operating while water is still present in the oil, such as between times 2 and 3 and times 5 and 6, are accounted for in the calculation of the degradation value.

In another embodiment, the one or more sensor processors 504 may calculate the degradation value of the asset based on temperature of the oil as monitored by the temperature sensor 510 (shown in FIG. 73). For example, the degradation value may be calculated based on the concentration of water in oil measured during time periods that the temperature of the oil is less than an evaporation threshold temperature. The evaporation threshold temperature of water in the oil may be approximately 60 or 80 or 100 degrees Celsius, depending on the vapor pressure of the ambient environment. Such time periods in which the oil temperature is less than the evaporation threshold temperature may be associated with the time periods that the rotor system is non-operating, such as between times 1 and 2 and between times 4 and 5. It is recognized that the time periods in which the oil temperature is less than the evaporation threshold temperature may be offset at least slightly from the time periods that the rotor system is non-operating due to warming up and cooling down of the oil. For example, after switching from the operating state to the non-operating state, there may be a lag period before the oil temperature cools to a temperature below the evaporation threshold temperature and water from condensation begins to accumulate in the oil. Similarly, after switching from the non-operating state to the operating state, there may be another lag period before the oil temperature exceeds the evaporation threshold temperature and the concentration of water in the oil begins to decrease due to evaporation.

In one or more embodiments herein, the calculation of the degradation value for the oil and/or the gearbox may account for intermediate states or sub-states of the asset system, such as turbine start, turbine warm-up, turbine cool-down, and turbine stop. For example, the degradation value may be calculated as the concentration of the polar analyte in the oil during time periods in which the rotor system is non-operating and during time periods in which the rotor system is warming up, since significant water may remain in the oil as the rotor system warms up after switching into the operating state from the non-operating state. The intermediate states of the rotor system may be determined using the one or more operating condition sensors, such as a temperature sensor, a vibration sensor, or the like.

Figure 75:
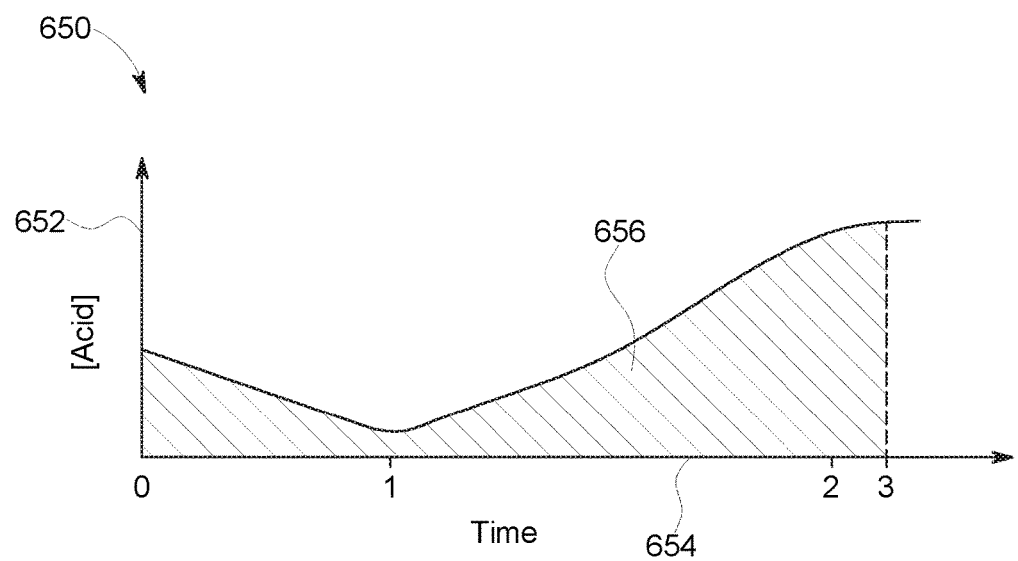
FIG. 75 is a plot of a concentration of acid in oil over time according to an embodiment.

FIG. 75 is a plot 650 of a concentration of acid in oil over time according to an embodiment. The y-axis 652 represents the concentration of acid in oil, which may be in parts per million or the like, and/or the total acid number (TAN) of the oil as an equivalent of mg KOH/g. The x-axis 654 represents time. The duration of the x-axis 654 from times 0 to 2 and beyond may be months or years. The time values 1 and 2 shown in FIG. 75 are not representative of regular, uniform time intervals. Between times 0 and 1, the concentration of acid in the oil slowly decreases, which may be due to depletion of stabilizing additives in the oil. The stabilizing additives may be or include acidic compounds, such that the acid concentration in the oil may decrease as the additives are depleted due to use of the oil in the gearbox. Between times 1 and 2, the concentration of acid in the oil increases due to one or more factors, such as breaking down of the oil into acidic compounds, introduction of acidic contaminants, and the like. For example, the oil may break down more rapidly after time 1 due to the lack of stabilizing additives in the oil due to depletion. The concentration of acid in the oil may begin to level out after time 2. A greater level of acid in the oil, particularly after the additives have depleted, can increase the amount of degradation of the oil and/or the gearbox. For example, the acid can cause corrosion of the gearbox and oxidation or other chemical reactions with different compounds in the oil, reducing the health of the gearbox and the oil. The detrimental effect of the acid in the oil is more severe at time 2 than at times 0 and 1 due to the greater concentration of acid in the oil at time 2 and the lack of stabilizing additives.

In an embodiment in which acid is the polar analyte of interest, the degradation value may be calculated as the product of the water concentration and the duration of time. Since the concentration of acid in the oil changes over time, the degradation value may be calculated as the integral of the acid concentration over time during the life of the asset. The integral is calculated to determine the area under the curve 656 between times 0 and 3 as shown in the plot 650 of FIG. 75.

Optionally, the degradation value of the asset (e.g., the gearbox and/or the oil in the gearbox) may account for degradation due to both water and acid. For example, a first component of the degradation value may be based on the concentration of water over time and a second component of the degradation value may be based on the concentration of acid over time. The first and second components may be weighted differently (e.g., using respective constants) in order to factor in the relative effect that each polar analyte has on the degradation of the asset. For example, the water may have a more severe detrimental effect on the asset than the acid, so the first component of the degradation value attributable to the water may be weighted greater than the weight of the second component of the degradation value attributable to the acid. Alternatively, the second component of the degradation value attributable to the acid may be weighted greater than the first component attributable to the water or the two components may be weighted equally.

Figure 76:
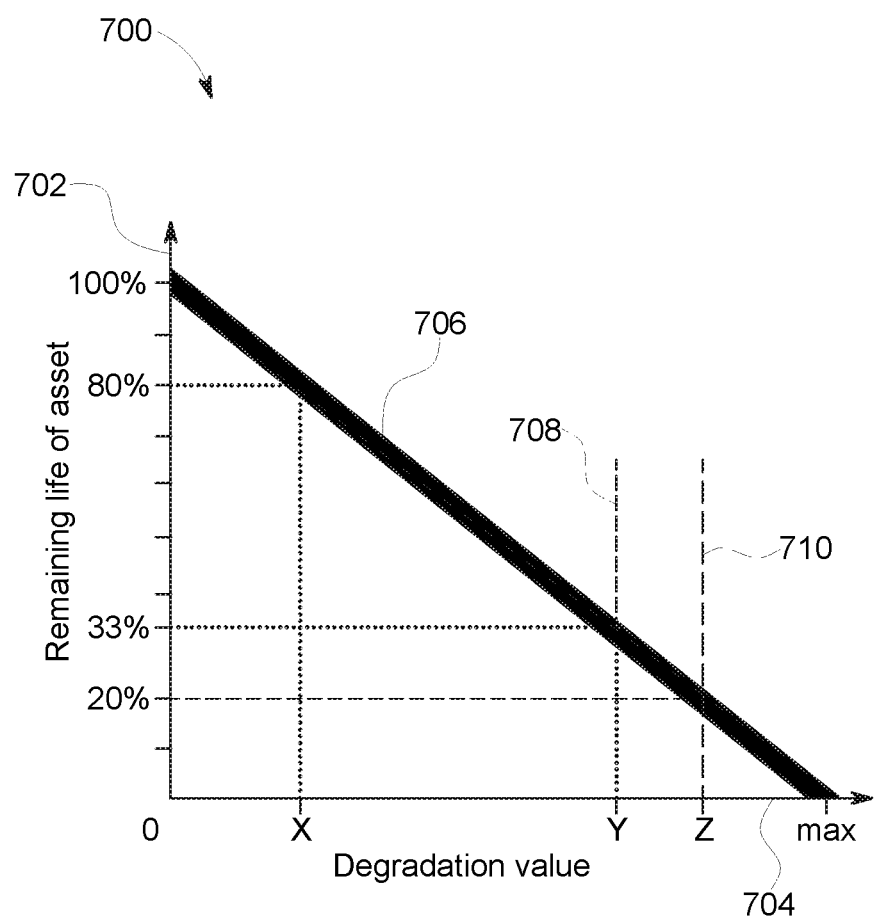
FIG. 76 is a plot of a remaining life of an asset over a degradation value of the asset according to an embodiment.

FIG. 76 is a plot 700 of a remaining life of an asset over a degradation value of the asset according to an embodiment. The y-axis 702 represents the remaining life of the asset, as demarcated by percentage of the remaining life. The x-axis 704 represents the degradation value. The degradation value may have units such as $ppm_{analyte}$, $ppm_{analyte}*hour$, or $ppm_{analyte}/hour$, or alternatively may be unitless. The x-axis 704 extends from 0 to a max degradation value. Although only three different values X, Y, and Z are marked on the x-axis 704 between 0 and the max degradation value, the x-axis 704 may have any number of values. The plot 700 includes a plot line 706 that shows the relationship between the remaining life of the asset and the degradation value. As shown in FIG. 76, the plot line 706 has a negative slope, which indicates that the remaining life of the asset is inversely proportional to the degradation value. For example, a new asset, such as fresh oil and/or a new gearbox, has 100% remaining life and a degradation value of 0. As the degradation value of the asset increases, the estimated remaining life of the asset decreases as shown by the plot line 706. In an embodiment, one or more processors (e.g., the one or more sensor processors 504 shown in FIG. 73) may generate the function (e.g., slope) of the plot line 706 based on historical data that compares calculated degradation values to monitored amounts of time remaining in a life of a similar asset. For example, the plot line 706 may represent a transfer function that associates calculated degradation values to corresponding percentages of remaining life of the asset based on historical data.

In an embodiment, after calculating the degradation value of an asset, the one or more processors may be configured to estimate the remaining amount of time in the operational life of the asset by plugging the degradation value into the function represented by the plot line 706 to yield an estimated remaining life of the asset. For example, as shown in FIG. 76, a degradation value of X for the gearbox translates to an estimated 80% of the life of the gearbox remaining. In another example, a greater degradation value of Y translated to an estimated 33% of the life of the gearbox remaining. During use of the asset, the degradation value gradually increases, moving along the x-axis 704 from 0 towards the max degradation value. The rate at which the degradation value increases (e.g., moves along the x-axis 704) is based on factors such as the concentration of the one or more polar analytes in the oil and the length of time that the one or more polar analytes are present in the oil. For example, a first oil with a greater concentration of water and a greater amount of time that the water is in the oil would predictably degrade faster (e.g., reaching the max degradation value quicker) than a second oil having a lower concentration of water and a reduced amount of time that the water is present in the oil. Providing an estimate of the remaining life of an asset, such as a gearbox or oil within the gearbox, allows for planning maintenance in advance. Therefore, the maintenance is performed when desirable or necessary, instead of performing the maintenance before necessary (which may be wasteful) or after the maintenance is necessary (which may be harmful to performance or other components of the rotor system). The one or more processors may convey the estimated remaining life of the asset to an operator, such as via transmitting a message containing the estimated remaining life to a computer, workstation, or personal handheld device.

In one or more embodiments, the one or more processors may monitor the degradation value of an asset relative to one or more designated degradation thresholds. The one or more degradation thresholds may be selected based on historical data of the similar assets. The degradation thresholds may be stored in memory of the one or more processors. The degradation thresholds are designed to trigger the one or more processors to take remedial actions to prevent reduced performance of the rotor system, extended shut-downs, and/or damage to the rotor system. Therefore, responsive to the degradation value of an asset exceeding a designated degradation threshold, the one or more processors are configured to automatically take a specified remedial action. For example, the processors may schedule maintenance for the rotor system, such as to change the oil in the gearbox, repair the gearbox, or replace the gearbox or a part thereof. The processors may be communicatively coupled to a computer, server, or operating system that schedules maintenance for the asset.

Additionally, or alternatively, the remedial action of the processors may be to provide an alert for an operator to schedule or perform maintenance for the rotor system. For example, the processors may trigger a message that is displayed to the operation via a workstation display screen or a handheld device display screen (e.g., a cell phone, tablet, wearable device, or the like). The alert for the operator may include visual text and/or graphics on a display, audible sounds or speaking via a speaker, and/or vibrations. Additionally, or alternatively, the remedial action may be to prohibit additional operation of the rotor system until maintenance is performed on the rotor system. The prohibition of operation of the rotor system may include the processors controlling the rotor system in the operating state to shut down and/or preventing the rotor system in the non-operating state from switching to the operating state. The rotor system may be prohibited from operating to protect the other components of the rotor system from possible damage due to the degraded oil and/or gearbox. For example, the rotor system is prohibited from operating to prevent a corroded gearbox from breaking down and damaging the generator, the hub connected to the rotors, or other components of the rotor system. The one or more processors may prevent the rotor system from operating by transmitting a message to a controller device of the rotor system and/or by triggering a switch that deactivates the operation of the rotor system.

Optionally, the one or more processors may monitor the degradation value of an asset relative to multiple degradation thresholds. For example, a first degradation threshold 708 may be the degradation value Y shown in FIG. 76, and a second degradation threshold 710 may be the degradation value Z, which is greater than the value Y. The first degradation threshold 708 is at 33% of the remaining life of the asset, and the second threshold 710 is at 20% of the remaining life of the asset. Responsive to the degradation value exceeding the first degradation threshold 708, the processors may be configured to schedule replacement of the oil within the gearbox and/or provide an alert to schedule replacement of the oil within the gearbox. Replacing the oil in the gearbox may reduce the rate at which the gearbox degrades due to the reduced corrosive contaminants in the healthy oil. In an embodiment, responsive to the degradation value exceeding the second degradation threshold 710, the processors may be configured to schedule servicing of the gearbox (e.g., repair or replacement of the gearbox) and/or provide an alert to schedule servicing of the gearbox. Although not shown in FIG. 76, a third degradation threshold greater than the value Z may be associated with 10%, 5%, 2%, or 1% of the remaining life of the asset. Upon exceeding the third degradation threshold, the one or more processors may be configured to prevent additional operation of the rotor system until after maintenance is performed on the rotor system.

Figure 77:
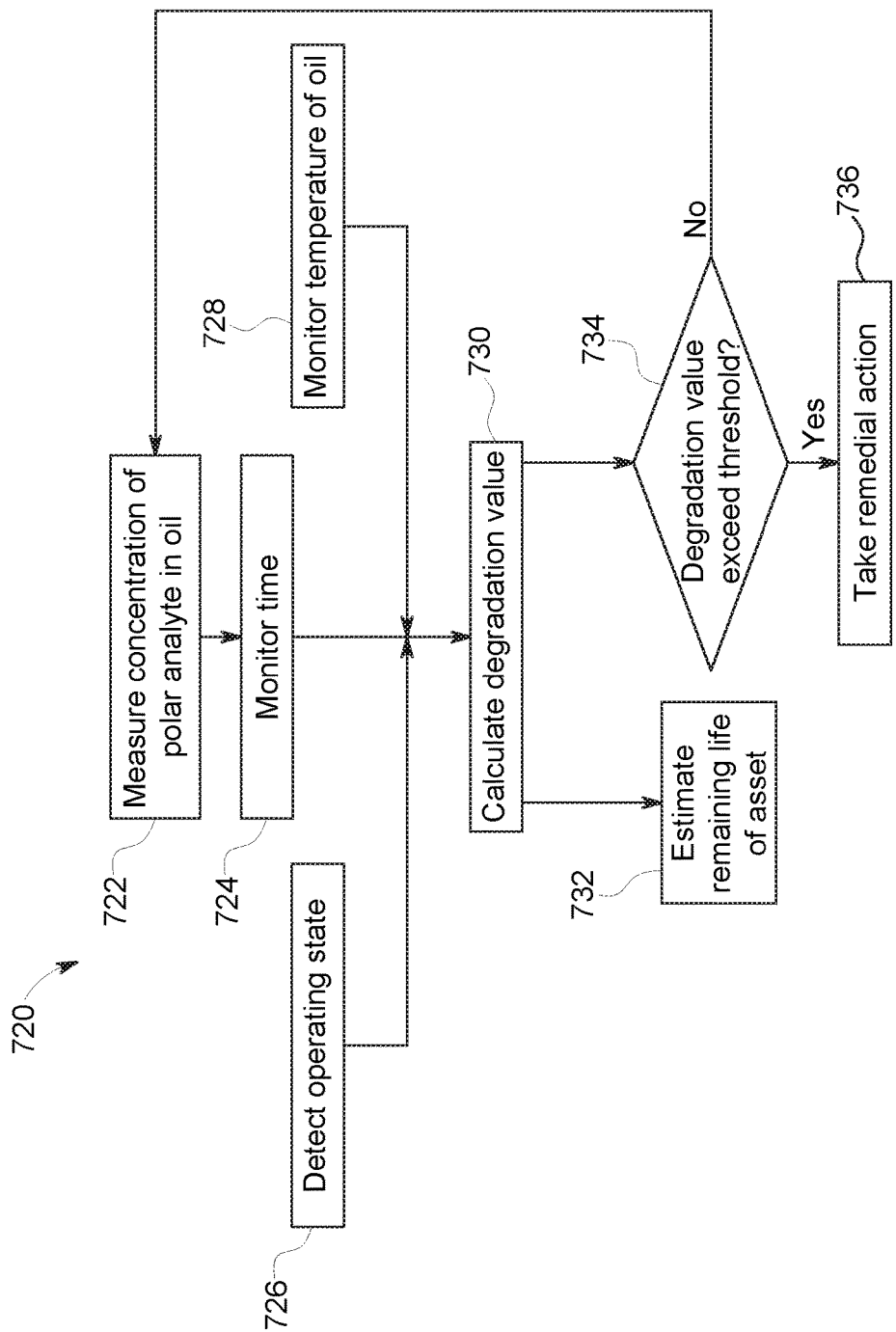
FIG. 77 is a flow chart of a method for monitoring an asset in a rotor system according to an embodiment.

FIG. 77 is a flow chart of a method 720 for monitoring an asset in a rotor system according to an embodiment. The asset may be a gearbox of the rotor system, oil within the gearbox, or another component or fluid of the rotor system. In the illustrated embodiment, the asset is the gearbox. At 722, a concentration of a polar analyte in the oil of the gearbox is measured. The polar analyte may be at least one of water or acid (e.g., an acidic component within the oil). The concentration may be measured by a multivariable resonant sensor and one or more processors, such as the multivariable resonant sensor 502 and the one or more processors 504 shown in FIG. 73. A measurement of the concentration may be obtained at different times during the operational life of the asset, such as periodically at a regular interval of one measurement every thirty seconds, every one minute, every two minutes, or the like. For each measurement, the multivariable resonant sensor generates an electrical stimulus having multiple different frequencies that is applied to the oil in contact with the multivariable resonant sensor, and an electrical signal representative of a resonant impedance spectral response to the electrical stimulus is conveyed to the one or more processors. The one or more processors analyze the impedance response and extract or calculate resonant parameters from the impedance response to determine the concentration of the polar analyte in the oil at the time that the electrical stimulus is applied to the oil. At 724, the time is monitored, such as via the time counter 520 shown in FIG. 73. Therefore, the measured concentrations of the polar analyte can be associated with time to track the concentration of the polar analyte over time.

Steps 726 and 728 are optional, such that the method 720 may be performed without either of steps 726 or 728, with both steps 726 and 728, or with only one of the steps 726 and 728. At 726, the operating state of the rotor system is detected, such as whether the rotor system is in an operating state or a non-operating state. In the case of a wind turbine, the wind turbine operates when the hub and rotors rotate and the generator generates electrical energy from the mechanical rotation of the hub and rotors. The operating state of the rotor system may be detected via an operating condition sensor, such as a vibration sensor mounted to the rotor system, an optical sensor that monitors the rotation of the hub and/or rotors, or an electromagnetic sensor that detects the flow of current from the generator. At least some of the measurements of the concentration of the polar analyte in the oil may be obtained while the rotor system is in the non-operating state. At 728, the temperature of the oil within the gearbox is monitored, such as via a temperature sensor.

At 730, a degradation value for the asset is calculated based on the concentration of the polar analyte in the oil as a function of time. The degradation value may be calculated by one or more processors, such as the one or more sensor processors 504 shown in FIG. 73. The degradation value may be calculated based on the concentration of the polar analyte, and how the concentration changes, over time during the operating life of the asset. For example, the degradation value may be calculated as an integral of the concentration of the polar analyte in the oil over a time period that the concentration measurements are obtained. Optionally, if the polar analyte is water, the degradation value for the asset is calculated, at least in part, based on measurements of the concentration of water in the oil that are obtained during time periods that the rotor system is non-operating as determined in step 726. The detrimental effect of water in the oil may be more significant in the non-operating state relative to the operating state because water can accumulate in the oil due to condensation when the rotor system is not operating. Optionally, the degradation value may be calculated based, at least in part, on measurements of the concentration of the polar analyte in the oil that are obtained during time periods that the temperature of the oil is less than an evaporation threshold temperature as determined in step 728. For example, the detrimental effect of the polar analyte in the oil may be more significant when the temperature of the oil is below the evaporation threshold temperature because the polar analyte may be present. At a higher temperature of the oil above the evaporation threshold temperature, the polar analyte may evaporate from the oil, reducing the concentration of the analyte as well as the associated harmful effects of the analyte.

At 732, a remaining amount of time in the operational life of the asset is estimated based on the degradation value for the asset. The remaining amount of time is inversely proportional to the degradation value as described above with reference to FIG. 76. The estimated remaining life of the asset may be conveyed to an operator and/or to a remote control facility and used for planning future maintenance or other service for the rotor system.

At 734, a determination is made whether the degradation value exceeds a designated degradation threshold. The one or more processors may determine whether one or more set degradation thresholds are exceeded. If at least one degradation threshold is exceeded by the calculated degradation value, then flow proceeds to 736 and remedial action is automatically taken. For example, the remedial action may include scheduling maintenance for the rotor system (e.g., such as to replace the oil within the gearbox or replace the gearbox or a component thereof), providing an alert to schedule maintenance for the rotor system, and/or prohibiting operation of the rotor system until maintenance is performed on the rotor system. If, on the other hand, the degradation value does not exceed a designated degradation threshold, flow may return to step 722 for additional monitoring of the polar analyte concentration in the oil.

Figure 78:
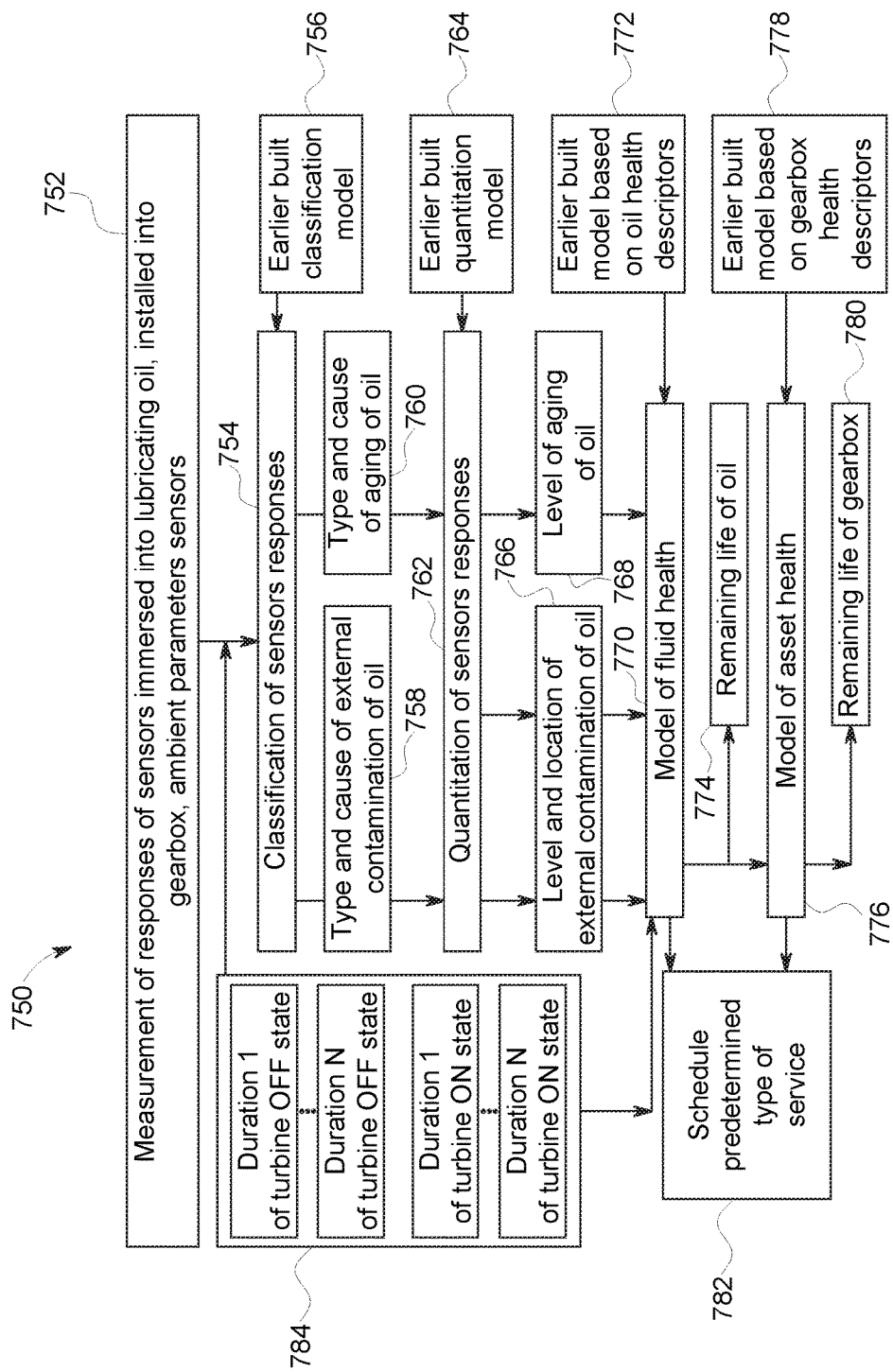
FIG. 78 is a flow chart of a method for predictive assessment of oil health and gearbox health according to an embodiment.

FIG. 78 is a flow chart of a method 750 for predictive assessment of oil health and gearbox health according to an embodiment. The method 750 may be similar to the method 720 of monitoring an asset in a rotor system shown in FIG. 77. The method 750 may include some of the same steps from the method 300 for monitoring and assessing a lubricating oil shown in FIG. 64 and/or the method 2860 for monitoring oil health shown in FIG. 14, and such steps are not described in detail with reference to FIG. 78.

At 752, various measurements are obtained from different sensors, including sensors immersed into lubricating oil (e.g., resonant sensor and/or temperature sensor), sensors installed into the gearbox (e.g., vibration sensor and/or temperature sensor), and/or ambient-parameter sensors (e.g., temperature sensor and/or humidity sensor). At 754, the sensor responses are classified by using a predetermined, earlier saved classification model at 756. At 758 and 760, determination of the individual effects of oil-aging compounds and external contaminants in gearbox oil is made. For example, the type and cause of external contamination of oil, such as acid or water, is determined at 758, and the type and cause of oil aging is determined at 760. At 762, the sensors responses are quantified by using a predetermined, earlier saved quantitation model at 764 to quantify the individual effects of oil-aging compounds and external contaminants in gearbox oil. For example, at 766 the level and location of external contamination of oil is determined, and at 768 the level of aging of the oil is determined.

At 770, a model of fluid health is generated and/or updated using an earlier-built model based on oil health descriptors at 772. The oil health descriptors may be based on sensor responses to changes in the properties of the oil, the gearbox, and/or the ambient environment. The obtained sensor responses are compared to the model of fluid health to estimate the remaining life of the oil at 774. At 776, a model of asset health (e.g., health of the gearbox) is generated and/or updated using an earlier-built model based on gearbox health descriptors at 778. The gearbox health descriptors may be based on sensor responses to changes in the properties of the oil, the gearbox, and/or the ambient environment. The obtained sensor responses are compared to the model of asset health to estimate the remaining life of the gearbox at 780. The oil health descriptors may include level and type of external contaminant such as water, molecularly dissolved water, dispersed (emulsified) water, wear particles, water in the air within the headspace of the gearbox, dust particles, and other external contaminants. The gearbox or asset health descriptors may include corrosion state, wear state of the gearbox or asset, and the like. Oil health descriptors and/or gearbox or asset health descriptors may also include time of operation since the previous maintenance of the gearbox or asset and time periods when the gearbox or asset was in ON and OFF states. In an embodiment, the model of the fluid health and/or the model of the asset health are used to schedule a predetermined type of service for the rotor system at 782. For example, if a calculated amount of degradation of the gearbox based on the model of fluid health and/or the model of asset health exceeds a designated threshold, the predetermined type of service may be scheduled. The type of service may include replacing the oil in the gearbox, repairing or servicing the gearbox, replacing the gearbox, or the like. The type of service that is scheduled may be based on the extent of degradation of the gearbox, ranging from replacing the oil responsive to a first level of degradation to replacing the entire gearbox responsive to a second, greater level of degradation.

In an embodiment, the time periods in which the rotor system (e.g., turbine) is in various operating states are monitored at 784, such as via a global time counter and one or more sensors that detect the operating state of the rotor system. For example, the rotor system may cycle between an operating or ON state and a non-operating or OFF state. The durations of time in each ON state and each OFF state are monitored. Optionally, other intermediate states of the turbine may also be monitored, such as turbine start, turbine warm-up, turbine cool-down, and turbine stop. The durations of time in each of the operating states may be used to classify the sensor responses at 754 and/or determine the model of fluid health at 770.

Sensors that may be utilized to accomplish the method 750 (for predictive assessment of oil health and gearbox health) may have several operational characteristics such as the ability to detect oil aging, the ability to detect the presence of water in oil, the ability to resolve oil aging vs presence of water, and the ability to separately quantify a level of oil aging vs the concentration of water in the oil.

The applicability of developed electrical resonators for prognostic monitoring of polar analytes in oil was experimentally tested and demonstrated as described with reference to FIGS. 79A-82. In the experimental setup, the polar analyte tested was water, and the asset was a helicopter engine. Oil contamination by water occurred when the oil was at ambient temperature. Then, the asset was started and the oil temperature increased with the simultaneous removal of water by water evaporation from the heated oil. During the dynamic startup of the asset, water was detected and quantified, providing the opportunity for prognostics of the asset.

In the experimental demonstration, a CT7 turboshaft helicopter engine was used to detect water dynamics in oil upon heating. The electrical resonator sensor (e.g., the resonant sensor 502 shown in FIG. 73) was operating at ~38 MHz (in oil) and was placed inside a 1-inch T-connector that was a part of a specially installed ⅜" outer diameter bypass oil line connected to the engine to ensure oil flow through the sensor during the engine operation. Water in the form of emulsion was added to the oil sump prior to the engine start. The homogenizer was used to emulsify water with the CT7 engine oil. An Agilent E5062A network analyzer was used to acquire the sensor response. Reference measurements of water content in oil were done using near-infrared spectroscopy. The near-infrared measurements of water content in a CT7 helicopter engine oil were carried out using a Cary 500i UV-vis-NIR spectrophotometer (Varian, Inc., Santa Clara, Calif.) using quartz cuvettes with a 1-cm pathlength. Initially, oil samples with known amounts of water were measured to establish the relationship between near-infrared absorbance and water content. Next, samples were taken between the runs of the CT7 helicopter engine and analyzed with near-infrared spectroscopy for the presence of residual water. The resonant sensor responses to different concentrations of water in oil were obtained by adding water concentrations of 1000, 3000, and 5000 ppm and observing the dynamic response patterns of the resonant sensor. The results of these experiments are summarized in FIG. 60A.

Figure 79A:
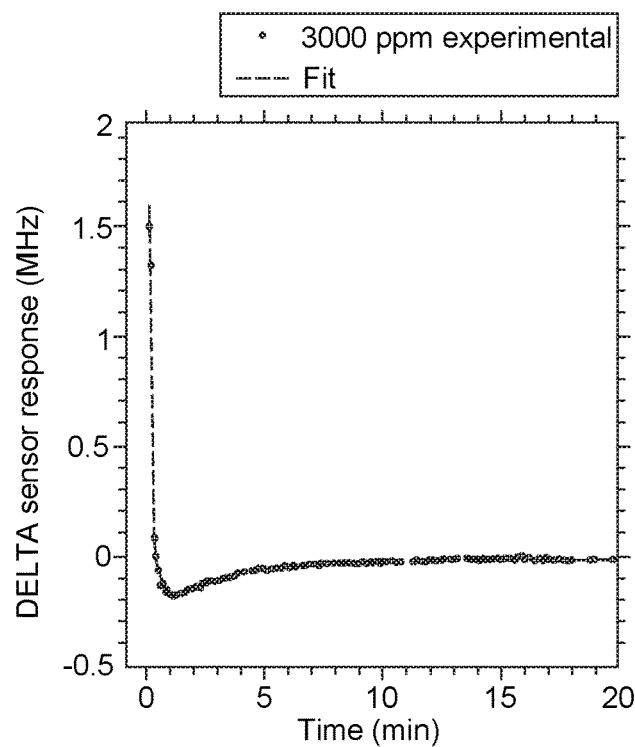
FIGS. 79A-B depict a developed two exponential-function using the response of the resonant sensor to 3000 ppm of water in oil according to an experimental test.
Figure 79B:
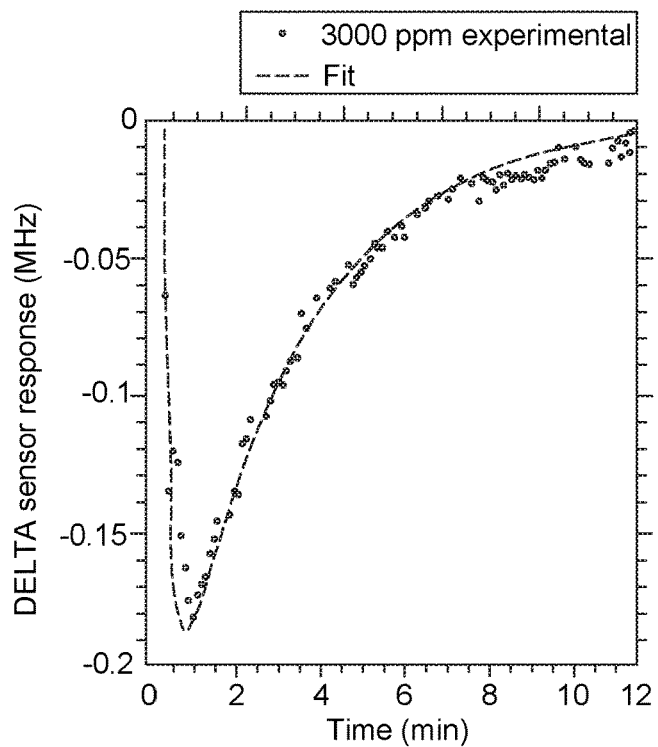

Water evaporation was fitted with a function that was a sum of two exponentials and a residual offset: [sensor] $=a1*\exp(-time/a2)+b1*\exp(-time/b2)+c1$. The first exponential $a1*\exp(-time/a2)$ describes heating of the oil upon engine start. The second exponential $b1*\exp(-time/b2)$ describes water evaporation from the oil upon engine start. The residual offset $c1$ describes any instabilities of the sensor. FIGS. 79A and 79B depict the developed two exponential-function using the response of the resonant sensor to 3000 ppm of water in oil. FIG. 79A shows the response in a time scale between 0 and 20 minutes and a response scale between −0.5 MHz and 2 MHz. FIG. 79B shows the response in a shorter time scale between 0 and 12 minutes and a reduced response scale between −0.2 MHz and 0 MHz in order to show greater detail of the fit.

Figure 80A:
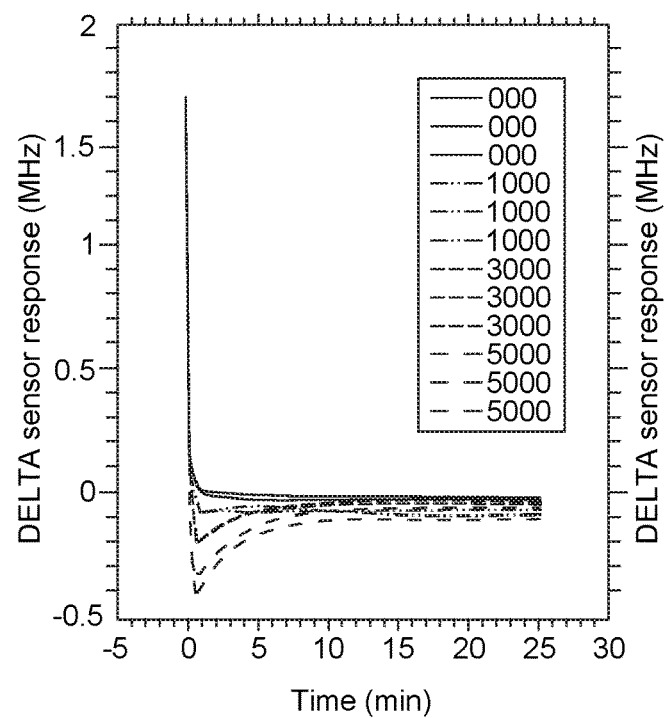
FIGS. 80A-C plot sensor response results for two exponential-function fits with runs containing 0, 1000, 3000, and 5000 ppm of water at two different response scales and the first derivative of the fits, respectively.
Figure 80B:
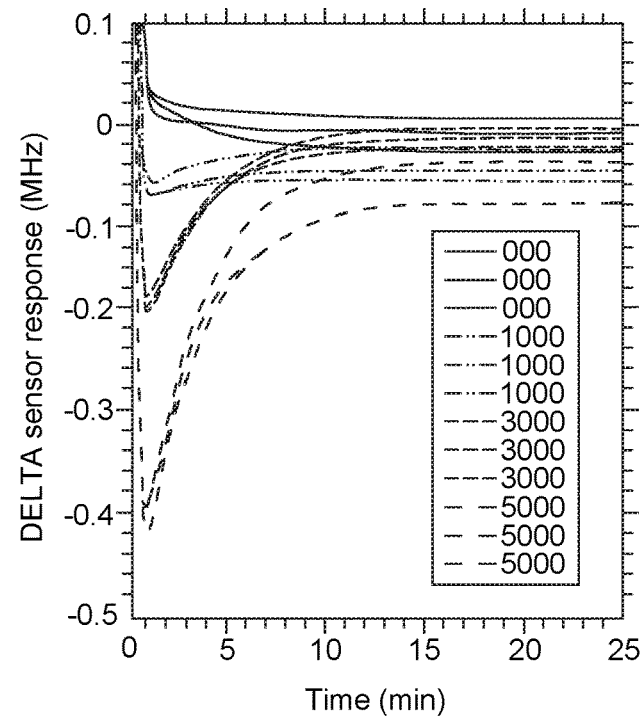
Figure 80C:
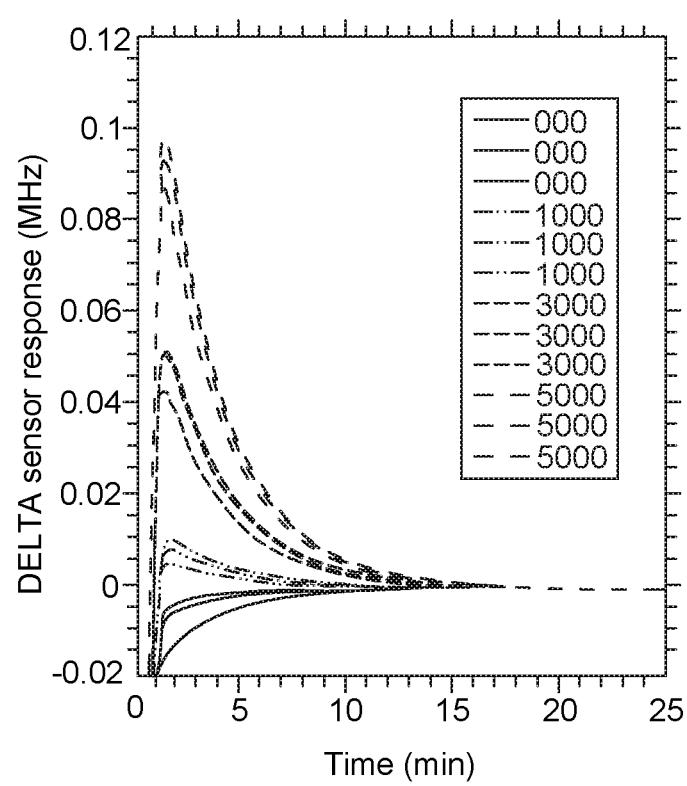

Two exponential-function fits were obtained for all replicates of measurements. Results for the two exponential-function fits with runs containing 0, 1000, 3000, and 5000 ppm of water are depicted in FIGS. 80A and 80B. FIG. 80A shows the sensor response scale from −0.5 MHz to 2 MHz. FIG. 80B shows the sensor response scale from −0.5 MHz to 0.1 MHz. The first derivative was further taken of all fits to reduce variability of the sensor quantitation due to the residual offsets, and the first derivative data is plotted in FIG. 80C to reduce the variability of the sensor quantitation due to residual effects.

Figure 81A:
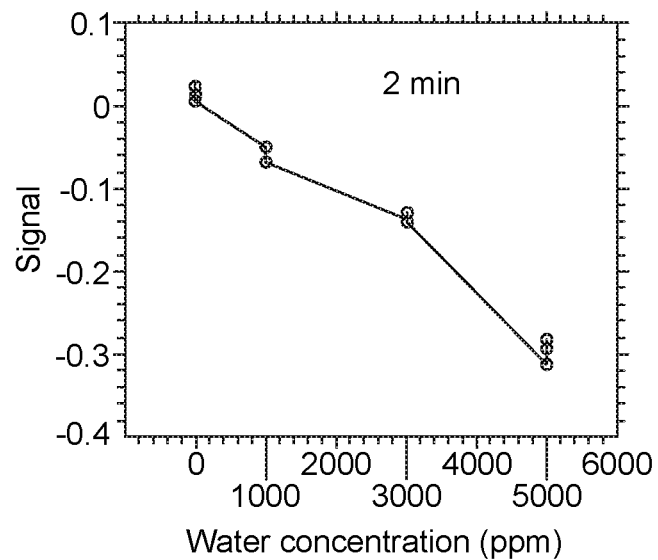
FIGS. 81A-B plot signals from the sensor response fits at 2 min and 10 min after the engine start.
Figure 81B:
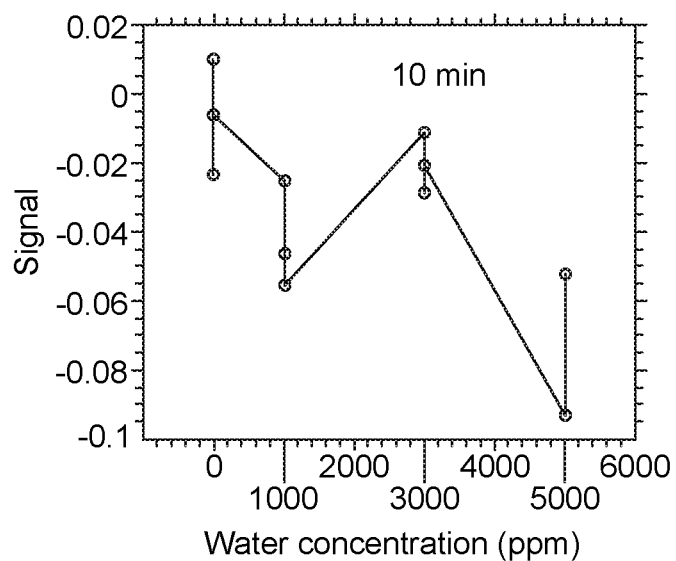
Figure 82A:
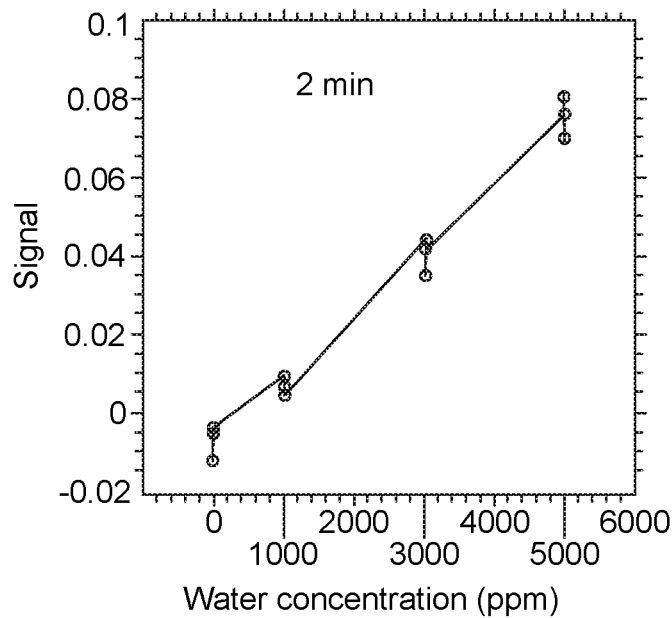
FIGS. 82A-B plot signals from the derivative of the sensor response fits at 2 min and 10 min after the engine start.
Figure 82B:
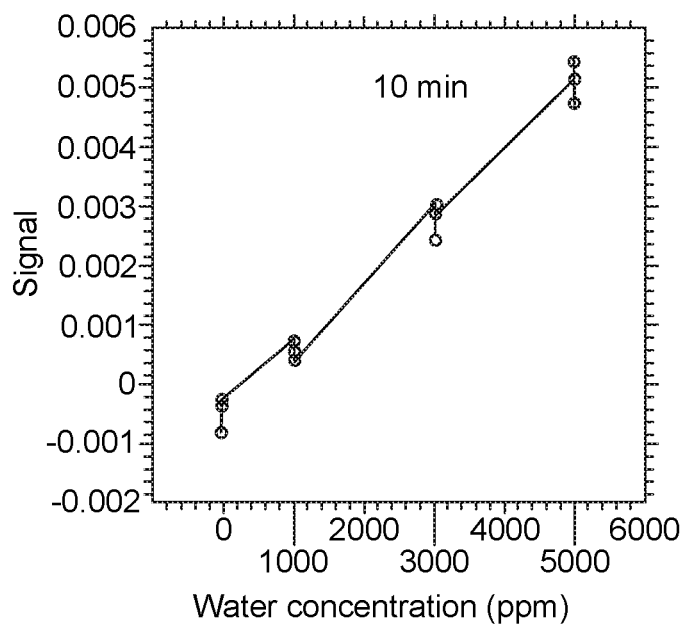

Signals from the sensor response fits were further plotted at 2 min and 10 min after the engine start as shown in FIGS. 81A and 81B, respectively. Such data analysis provided the ability to assess the reproducibility of measurements. Signals from the sensor response fits at 2 min were inversely proportional to the water concentrations in oil as shown in FIG. 81A. However, signals from the sensor response fits at 10 min had significant scatter due to the residual sensor offsets as shown in FIG. 81B. This scatter problem was eliminated by taking the first derivative of the sensor response. Signals from the derivative of the sensor response fits were plotted at 2 min and 10 min after the engine start as shown in FIGS. 82A and 82B, respectively. As shown in FIG. 82A, signals at 2 min were proportional to the water concentrations in oil. As shown in FIG. 82B, a similar sensor precision was obtained at 10 min relative to the sensor precision at 2 min, indicating elimination of the scatter due to the residual sensor offsets.

Figure 83:
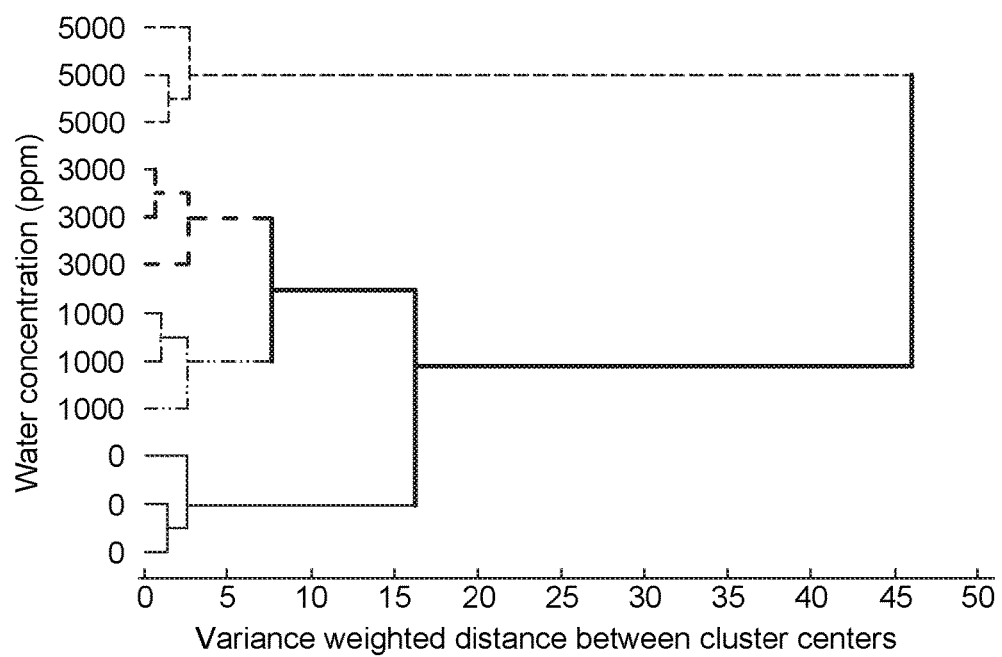
FIG. 83 illustrates a hierarchical cluster analysis dendrogram of sensor responses to 0, 1000, 3000, and 5000 ppm of water in oil.

Hierarchical cluster analysis of sensor responses to 0, 1000, 3000, and 5000 ppm of water in oil was further performed. This technique classifies samples using complete dynamic profiles. A hierarchical cluster analysis dendrogram is illustrated in FIG. 83. The hierarchical cluster analysis dendrogram was obtained using Ward's method that shows the Euclidean distance between trials. The Ward's method is a minimum variance method, which takes into consideration the minimum amount of variance between the samples and analytes to define a cluster. FIG. 83 depicts results of the Hierarchical cluster analysis of sensor responses to 0, 1000, 3000, and 5000 ppm of water in oil and illustrates good separation between sensor responses to different water concentrations.

Figure 84A:
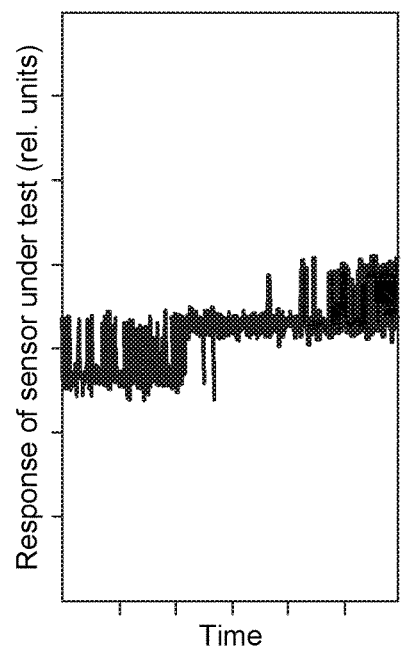
FIGS. 84A-E plot responses of various sensors to TAN additions in wind turbine gearbox oil.
Figure 84B:
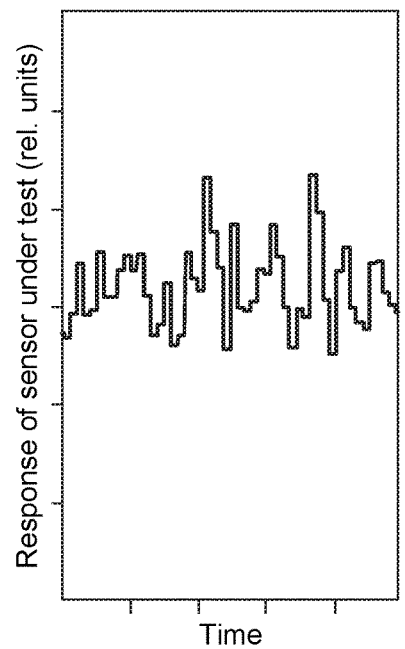
Figure 84C:
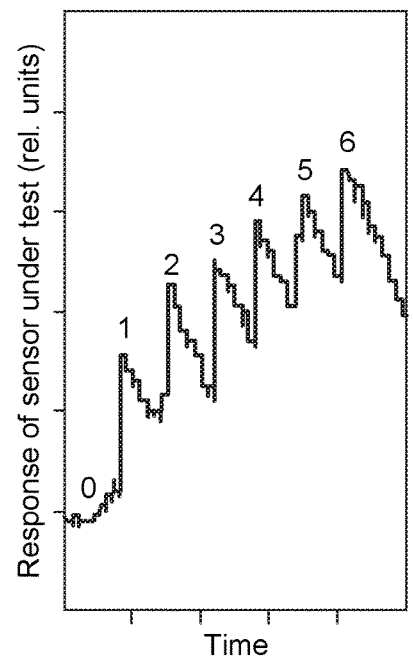
Figure 84D:
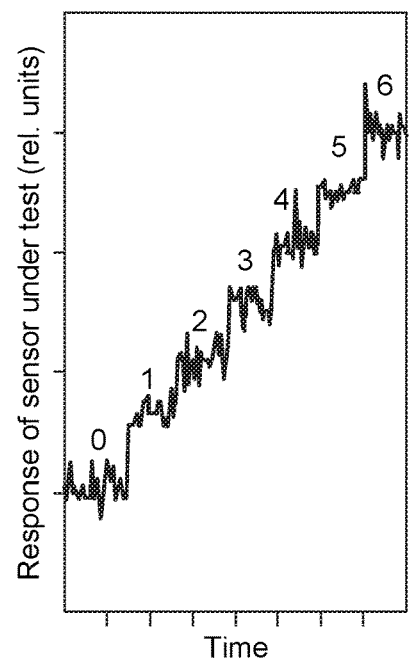
Figure 84E:
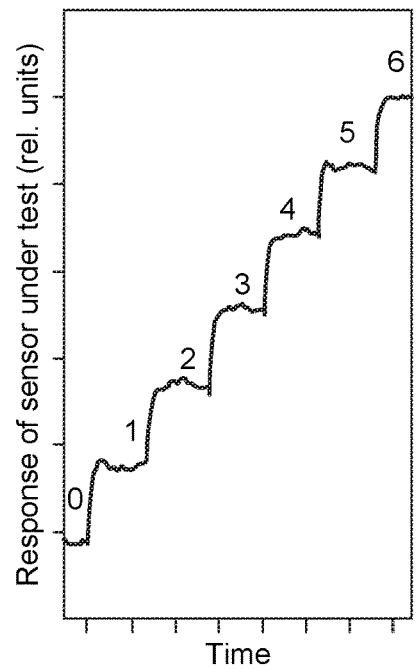

FIGS. 84A-E plot responses of various sensors to TAN additions in wind turbine gearbox oil. The multivariable resonant sensor described herein was tested with three other types of sensors. A benchmarking of performance of the four oil sensors was performed using a Castrol Optigear Synthetic X 320 gearbox oil for wind turbines. A first benchmark sensor (e.g., Sensor I) is shown in FIG. 84A. The first benchmark sensor measures molecularly-dissolved water in oil, and uses a capacitor with an air-humidity sensing film as the sensing principle. A second benchmark sensor (e.g., Sensor II) is shown in FIGS. 84B and 84C and includes two different sensing principles. The second benchmark sensor includes a capacitor with an air-humidity sensing film for sensing molecularly-dissolved water in oil. The second benchmark sensor also operates using a four-frequency impedance for sensing general changes of the chemistry of oil. A third benchmark sensor (e.g., Sensor III) is shown in FIG. 84D. The third benchmark sensor measures viscosity, density, and dielectric constant, and operates using an electro-mechanical resonator (e.g., tuning fork). The multivariable resonant sensor (e.g., Sensor IV) is shown in FIG. 84E. The resonant sensor measures external contaminants in oil and internal oil aging using a high-frequency electrical multivariable resonator.

The performances of the four sensors were compared by testing sensor responses to additions of TAN, additions of molecularly-dissolved water at both relatively low concentrations and relatively high concentrations, and additions of both TAN and molecularly-dissolved water. All measurements were performed at a constant oil temperature of 75 degrees C. All sensors were positioned in a common manifold and were exposed to the same oil and contaminants during experiments.

In a first experiment, decanoic acid was used to increase TAN in six levels resulting in TAN values of 1.3, 2.6, 3.9, 5.1, 6.4, and 7.6 mg KOH/g (referred to herein as TAN levels 1-6). The time between additions of TAN was approximately 10 minutes. FIGS. 84A-E depict responses of the three benchmark sensors and the multivariable resonant sensor to the TAN additions at the TAN levels 1-6 (e.g., the first experiment). Sensor I, the first benchmark sensor having a capacitor with air-humidity sensing film, did not respond to TAN additions, as shown in FIG. 84A. Sensor II, the second benchmark sensor with four frequencies of impedance response, did not respond to TAN additions, as shown in FIG. 84B. However, the capacitor with air-humidity sensing film of Sensor II responded to TAN additions with a response shown in FIG. 84C. Sensor III, the third benchmark sensor with a dielectric response, responded to TAN additions but with poor a signal-to-noise ratio, as shown in FIG. 84D. Sensor IV, the multivariable resonant sensor described herein responded to TAN additions with good signal-to-noise ratio shown in FIG. 84E, indicating an ability to detect all of the TAN additions.

Figure 85A:
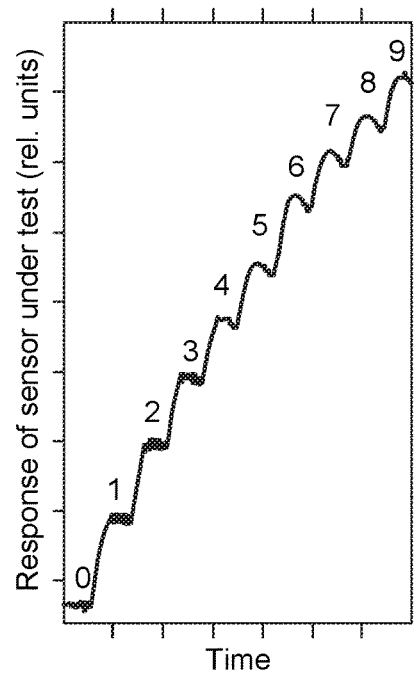
FIGS. 85A-E plot responses of various sensors to additions of molecularly dissolved water in wind turbine gearbox oil at relatively low concentrations.
Figure 85B:
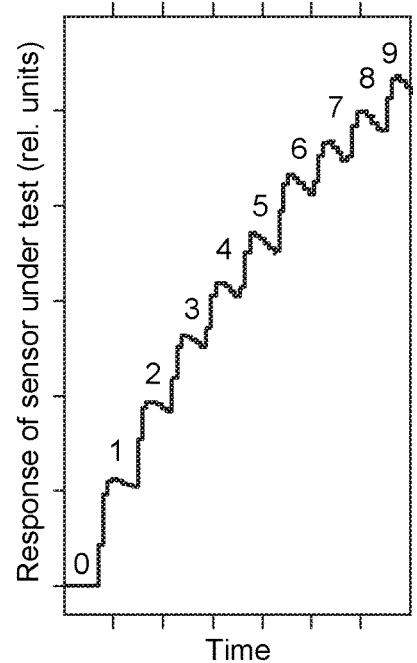
Figure 85C:
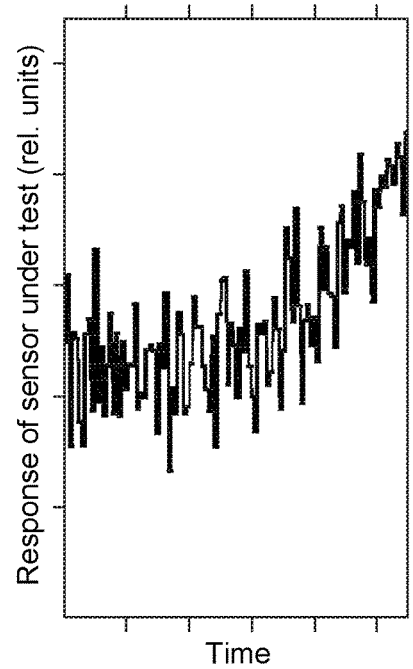
Figure 85D:
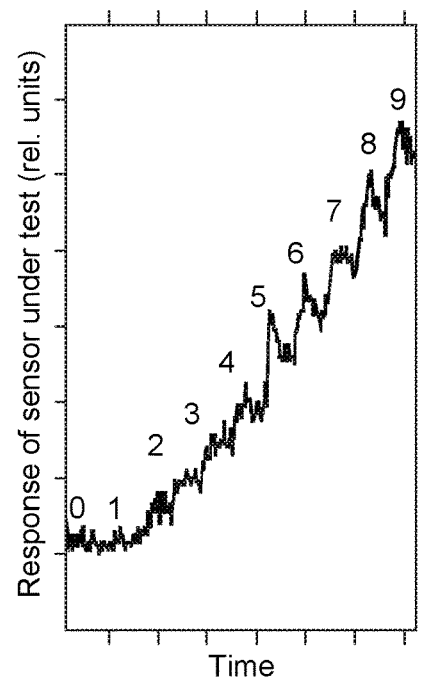
Figure 85E:
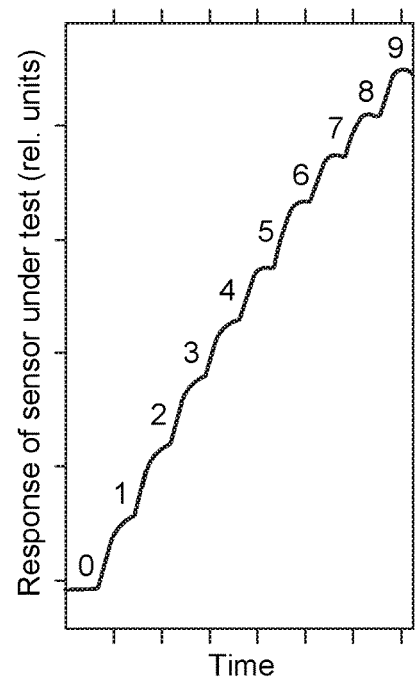

In a second experiment, water was added to generate nine levels of increasing concentrations of molecularly-dissolved water at relatively low concentrations of 28, 56, 83, 111, 139, 167, 194, 222, and 250 ppm (referred to as dissolved water levels 1-9). The time between additions of water was approximately 12 minutes. FIGS. 85A-E plot responses of the various sensors (e.g., the benchmark sensors I-III and multivariable resonant sensor IV) to the additions of molecularly dissolved water in wind turbine gearbox oil at relatively low concentrations. These additions were approximating the range of the molecularly dissolved water at relatively low concentrations. As shown in FIG. 85A, Sensor I responded with a good signal-to-noise ratio to water additions being able to resolve well all steps of water additions. Sensor II, with its capacitor with air-humidity sensing film, also responded with a good signal-to-noise ratio to water additions being able to resolve well all steps of water additions, as shown in FIG. 85B. The impedance response of Sensor II at four frequencies did not produce significant response to water additions, as shown in FIG. 85C. Sensor III responded to water additions with poor signal-to-noise ratio, as shown in FIG. 85D. The multivariable resonant sensor (Sensor IV) responded to water additions with a good signal-to-noise ratio, as shown in FIG. 85E, indicating an ability to resolve well all steps of water additions.

Figure 86A:
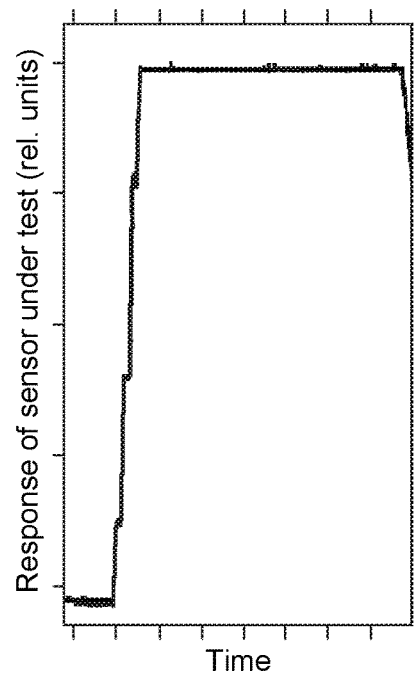
FIGS. 86A-E plot responses of sensors to additions of molecularly dissolved water in wind turbine gearbox oil at relatively low and high concentrations FIGS. 87A-B plot an effect of molecularly dissolved water and TAN in wind turbine gearbox oil on Fp and Zp parameter sensor responses, respectively.
Figure 86B:
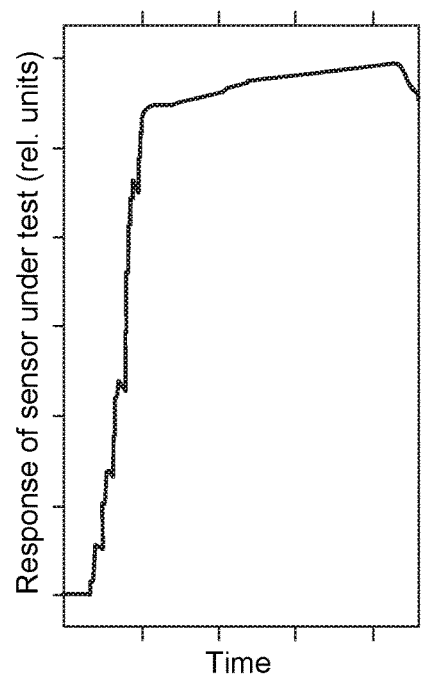
Figure 86C:
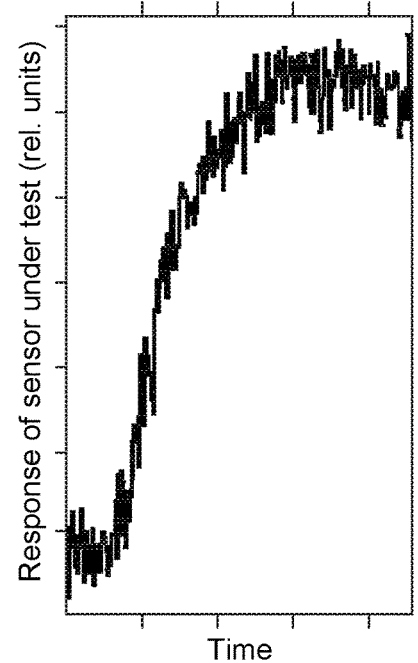
Figure 86D:
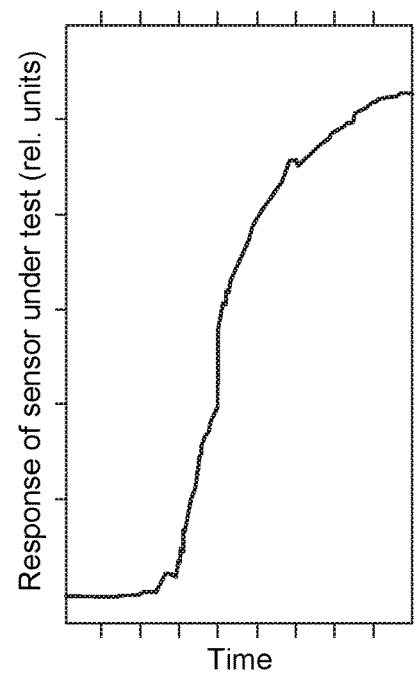
Figure 86E:
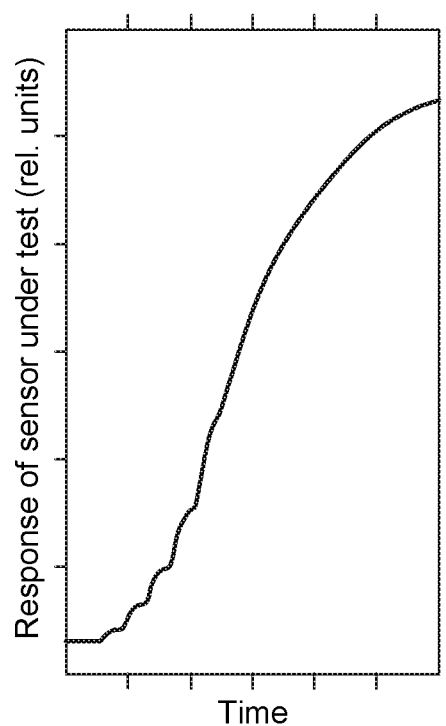

In a third experiment, water was also added to generate seven levels of increasing concentrations of water at both relatively low and high concentrations of 28, 83, 167, 306, 528, 972, and 1639 ppm (referred to as dissolved water levels 1-7). The time between additions of water was approximately 12 minutes. FIGS. 86A-E plot responses of the sensors (e.g., benchmark sensors I-III and multivariable resonant sensor IV) to additions of molecularly dissolved water in wind turbine gearbox oil at relatively low and high concentrations. Sensor I with its capacitor with air-humidity sensing film, as shown in FIG. 86A, saturated upon additions of relatively high concentrations of dissolved water. Sensor II, with its capacitor with air-humidity sensing film, responded to water additions with saturation upon additions of relatively high concentrations of dissolved water, as shown in FIG. 86B. The impedance measurements of Sensor II provided response to water additions with relatively poor signal-to-noise ratio, as depicted in FIG. 86C. The Sensor III with its dielectric constant response responded to water additions with a good signal-to-noise ratio as shown in FIG. 86D. The multivariable resonant sensor (Sensor IV) responded to water additions with a good signal-to-noise ratio as shown in FIG. 86E, indicating an ability to resolve well all steps of water additions.

In a fourth experiment, decanoic acid and water were added to generate nine levels of combination TAN and water concentrations. The nine levels include level 1 (0 mg KOH/g and 0 ppm), level 2 (0 mg KOH/g and 28 ppm), level 3 (0 mg KOH/g and 56 ppm), level 4 (3.9 mg KOH/g and 0 ppm), level 5 (3.9 mg KOH/g and 28 ppm), level 6 (3.9 mg KOH/g and 56 ppm), level 7 (7.6 mg KOH/g and 0 ppm), level 8 (7.6 mg KOH/g and 28 ppm), and level 9 (7.6 mg KOH/g and 56 ppm).

To discriminate between TAN and water, at least two partially independent responses (e.g., outputs) from a sensor may be required, where both responses have an adequate signal-to-noise ratio. In the fourth experiment, Sensor I had only one output from its capacitor with air-humidity sensing film and did not have capability to respond to TAN. Thus, Sensor I was unable to discriminate between TAN and water. Sensor II had only one output from its capacitor with air-humidity sensing film and four frequencies of impedance response. Sensor II responded to water but did not respond to TAN. Thus, Sensor II was also unable to discriminate between TAN and water. Sensor III had only one output from its dielectric readout that responded to water and TAN. Thus, Sensor III was unable to discriminate between TAN and water. The multivariable resonant sensor (Sensor IV) has several outputs, as described in FIG. 8, that respond differently to water and TAN.

Figure 87A:
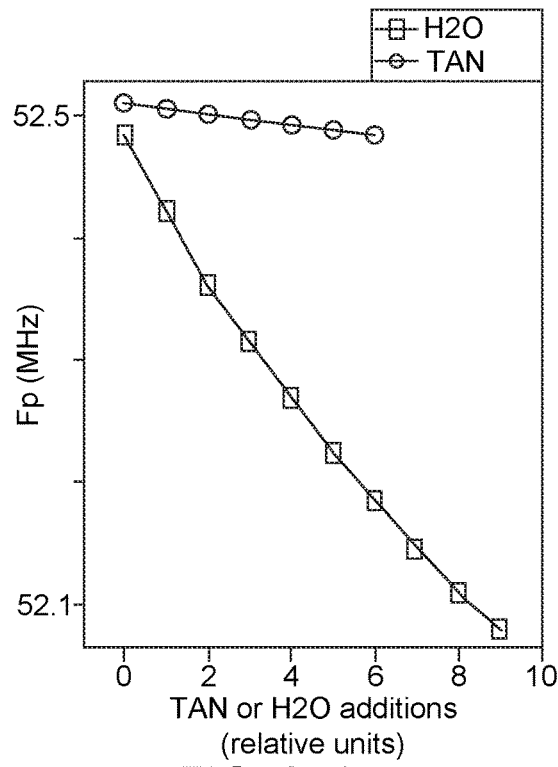
Figure 87B:
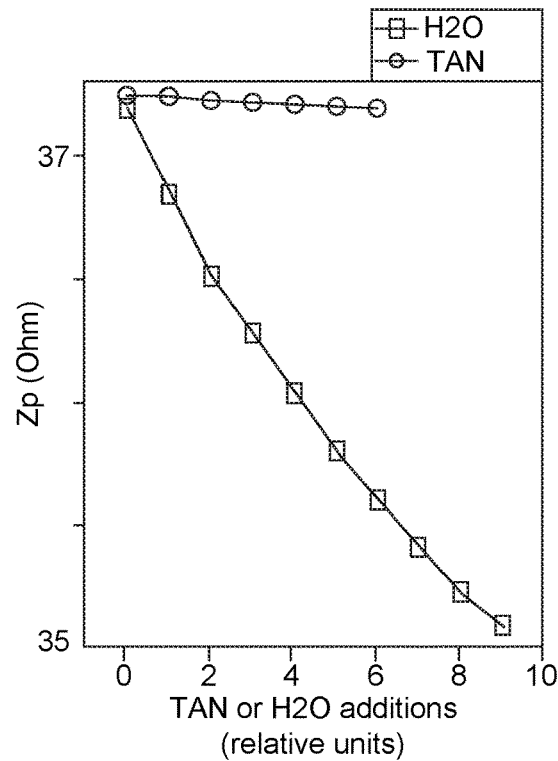

FIGS. 87A-B plot an effect of molecularly dissolved water and TAN in wind turbine gearbox oil on Fp and Zp parameter sensor responses, respectively. FIGS. 87A-B depict responses Fp and Zp of the multivariable resonant Sensor IV when Sensor IV was exposed to six levels of TAN and nine levels of molecularly dissolved water. The six levels of TAN were 1.3, 2.6, 3.9, 5.1, 6.4, and 7.6 mgKOH/g. The nine levels of molecularly dissolved water were 28, 56, 83, 111, 139, 167, 194, 222, and 250 ppm. The effect of water was clearly visible in the Fp response shown in FIG. 87A and the Zp response shown in FIG. 87B, based on the slopes of the response curves as a function of different water concentrations. The effect of TAN was also clearly visible in the Fp response shown in FIG. 87A and negligible in the Zp response shown in FIG. 87B (due to the reduced slope of the Zp response as a function of different TAN concentrations). This difference in response sensitivities of Fp and Zp to TAN allows the Sensor IV to discriminate between TAN and water. TAN and water was quantitatively discriminated using Sensor IV by multivariate processing of the sensor responses (e.g., described with reference to FIG. 8) using a multivariate transfer function. For each of the steps of TAN and water, three data points were used in the regions of the steady-state response of the sensor.

Figure 88A:
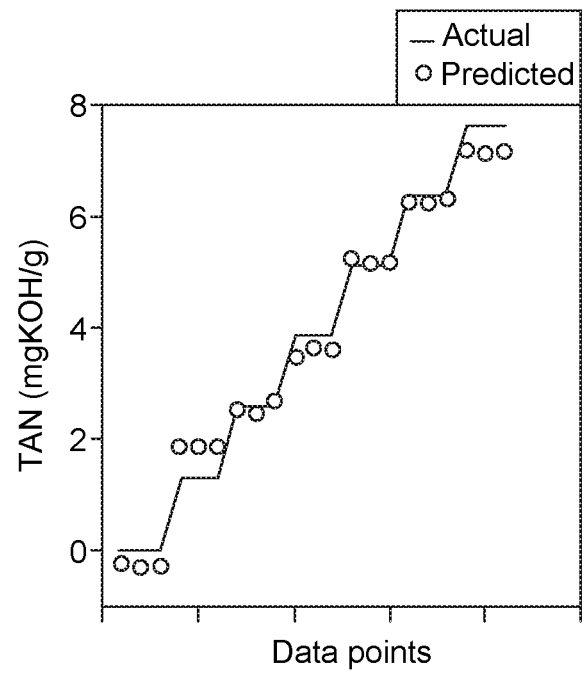
FIGS. 88A-B plot measured concentrations and predicted concentrations of TAN in wind turbine gearbox oil and water in wind turbine gearbox oil, respectively.
Figure 88B:
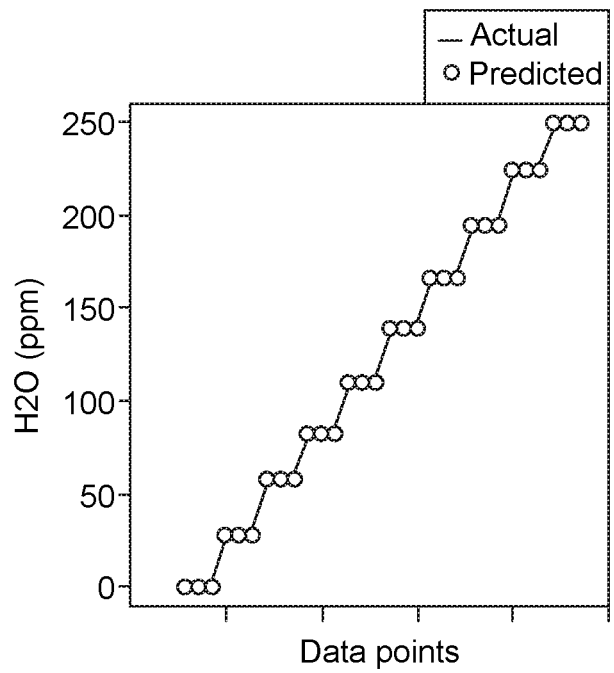
Figure 89A:
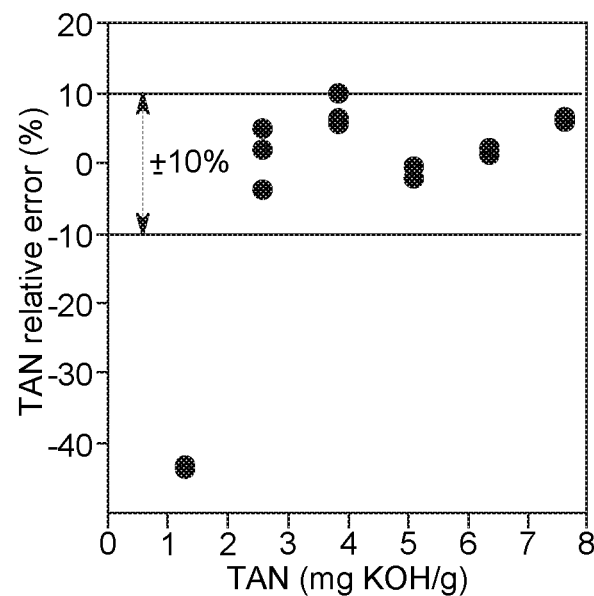
FIGS. 89A-B plot prediction errors between actual and predicted concentrations of TAN in wind turbine gearbox oil and water in wind turbine gearbox oil, respectively.
Figure 89B:
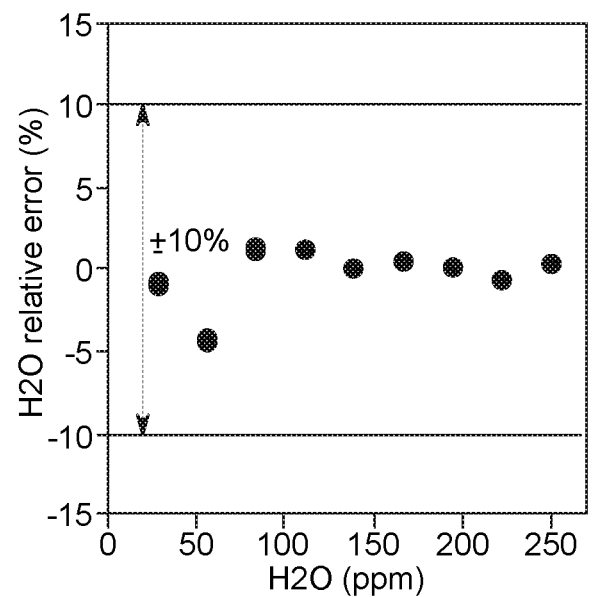

FIGS. 88A-B plot measured concentrations and predicted concentrations of TAN in wind turbine gearbox oil and water in wind turbine gearbox oil, respectively, using the multivariable resonant sensor. FIG. 88A depicts the actual (measured) concentrations of TAN in oil (solid line) and predicted concentrations (open circles). FIG. 88B depicts the actual (measured) concentrations of water in oil (solid line) and predicted concentrations (open circles). FIGS. 89A-B plot prediction errors between actual and predicted concentrations of TAN in wind turbine gearbox oil and water in wind turbine gearbox oil, respectively, using the multivariable resonant sensor. The percent error is calculated relative to the actual measured value. The errors in FIGS. 89A-B are typically +/−10% or less in the predicted values of TAN and water with the exception of one very low TAN value shown in FIG. 89A.

Figure 90:
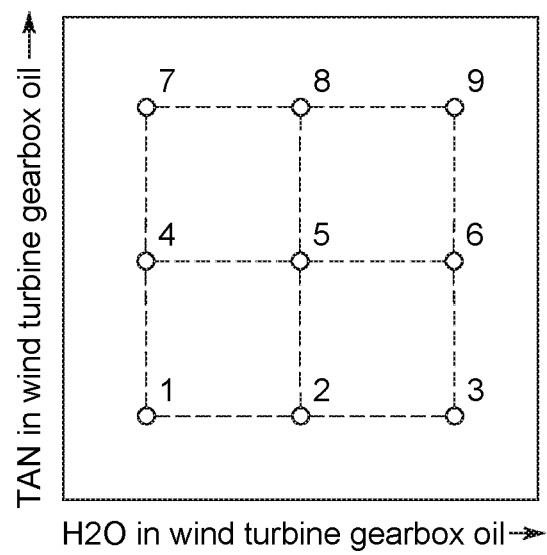
FIG. 90 depicts an experimental grid of nine levels with varying TAN and water levels in wind turbine gearbox oil.
Figure 91:
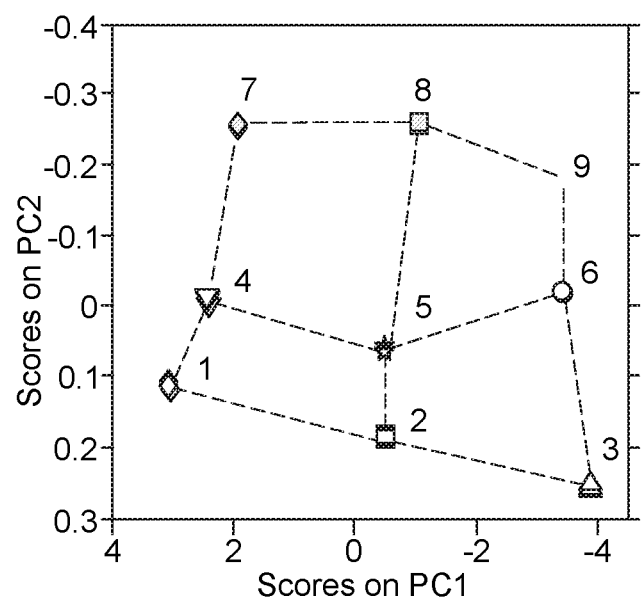
FIG. 91 depicts a scores plot of a developed PCA model illustrating spectral relation between sensor responses to the different types of contamination in the nine oil samples shown in FIG. 89.

FIG. 90 depicts an experimental grid of nine levels with varying TAN and water levels in wind turbine gearbox oil. Additions of TAN and molecularly dissolved water were performed in nine levels resulting in a combination of TAN (mgKOH/g) and water (ppm) concentrations: level 1 (0 mgKOH/g and 0 ppm), level 2 (0 mgKOH/g and 28 ppm), level 3 (0 mgKOH/g and 56 ppm), level 4 (3.9 mgKOH/g and 0 ppm), level 5 (3.9 mgKOH/g and 28 ppm), level 6 (3.9 mgKOH/g and 56 ppm), level 7 (7.6 mgKOH/g and 0 ppm), level 8 (7.6 mgKOH/g and 28 ppm), and level 9 (7.6 mgKOH/g and 56 ppm). FIG. 91 depicts a scores plot of a developed PCA model illustrating spectral relation between multivariable resonant sensor responses to the different types of contamination in the nine oil samples shown in FIG. 90. The scores plot shows Principal component 1 (PC1) vs. Principal component 2 (PC2) illustrating spectral relation between sensor responses to the different types of contamination in the nine oil samples shown in FIG. 90. As shown in FIG. 91, the experimental grid from FIG. 90 is visible in the scores plot, which indicates an ability to discriminate between all nine points of the experimental grid of samples using the PCA. For example, the experimental grid in FIG. 91 is a distorted version of the grid shown in FIG. 90, but all nine points are visible in the distorted view and have different coordinates in the scores plot.

Figure 92A:
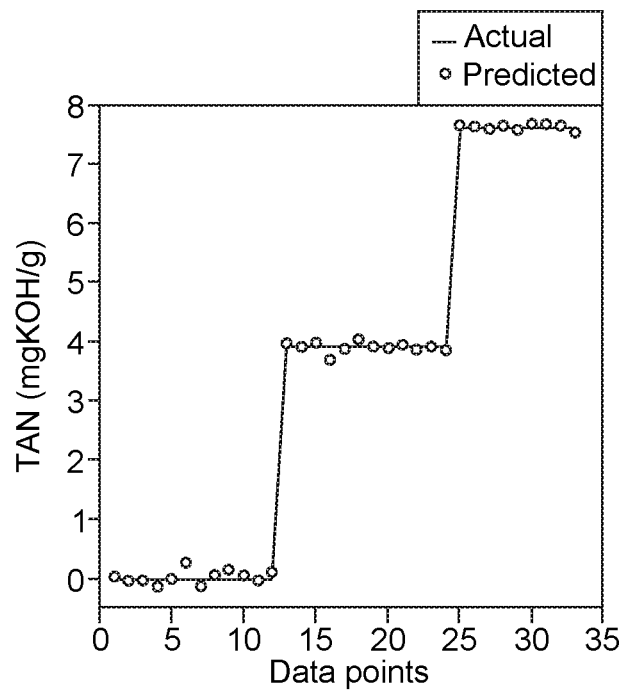
FIGS. 92A-B plot the results of predicted and actual TAN levels for different samples of wind turbine gearbox oil tested using the multivariable resonant sensor, and the residual error of the predicted TAN, respectively.
Figure 92B:
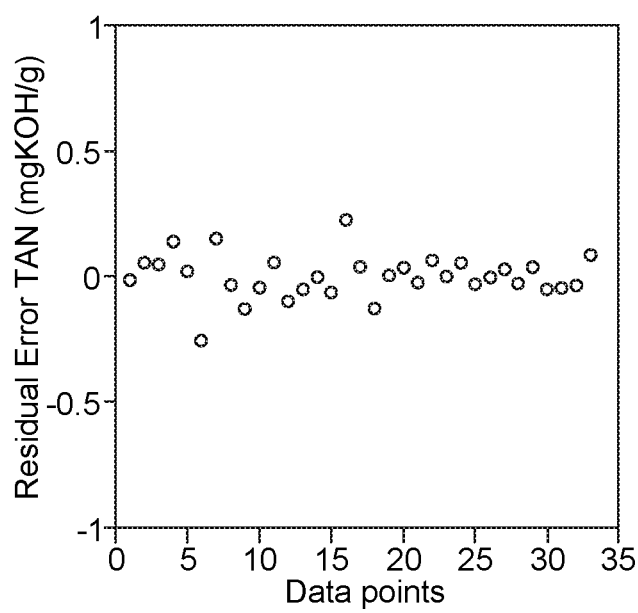

In the experimental methodology, the TAN and water levels were further determined or predicted using a multivariate regression technique. FIG. 92A plots the results of predicted and actual TAN levels for the different samples of oil tested using the multivariable resonant sensor. FIG. 92B plots the residual error of the TAN prediction using the multivariable resonant sensor. The results shown in FIGS. 92A and 92B illustrate that the multivariable sensor quantifies TAN in wind turbine gearbox oil samples having different amounts of water therein with less than ±0.25 mgKOH/g residual error. Therefore, the multivariable resonant sensor is able to predict a TAN level (e.g., an acid concentration) in a wind turbine gearbox oil sample, regardless of whether or not the oil sample includes a non-negligible concentration of water or other polar additives therein.

Figure 93A:
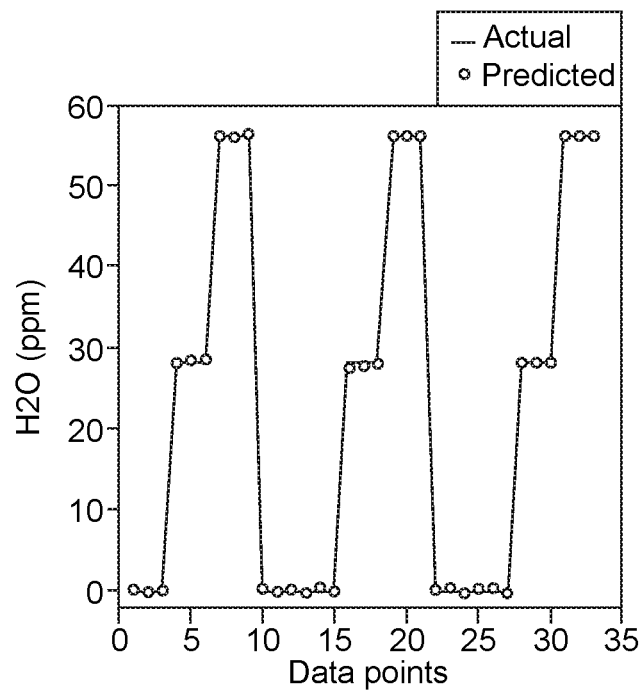
FIGS. 93A-B plot the results of predicted and actual water concentrations in oil for different samples of wind turbine gearbox oil tested using the multivariable resonant sensor, and the residual error of the predicted water concentrations, respectively.
Figure 93B:
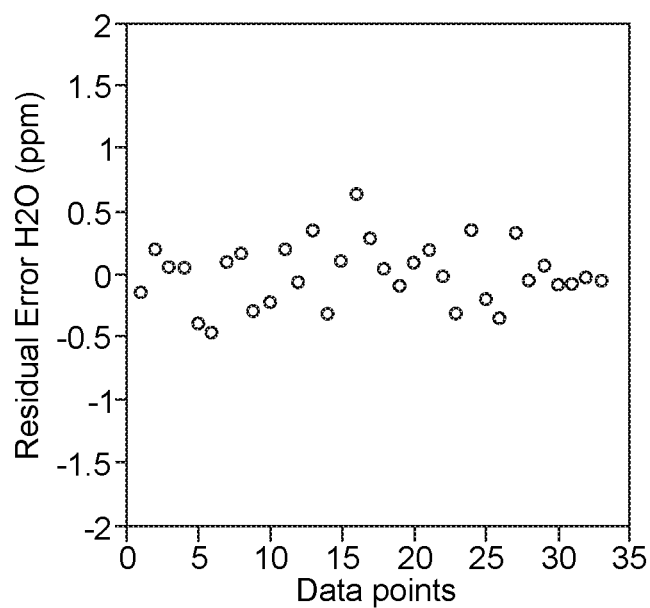

FIGS. 93A-B plot the results of predicted and actual water concentrations in oil for different samples of wind turbine gearbox oil tested using the multivariable resonant sensor, and the residual error of the predicted water concentrations, respectively. FIG. 93A shows the results of predicted and actual concentrations of water in wind turbine gearbox oil for the different samples of oil tested using the multivariable resonant sensor at different TAN levels. FIG. 93B plots the residual error of the water concentration prediction using the multivariable resonant sensor. The results shown in FIGS. 93A and 93B illustrate that the multivariable sensor quantifies water concentrations in oil samples having different amounts of acid therein with less than ±1 ppm residual error. Therefore, the multivariable resonant sensor is able to predict a concentration of water in a wind turbine gearbox oil sample, regardless of whether or not the oil sample includes a non-negligible concentration of acid or other polar additives therein. Furthermore, the single multivariable resonant sensor is able to predict both a water concentration and a TAN level of a wind turbine gearbox oil sample based on a single spectral impedance response of the sensor in contact with the wind turbine gearbox oil.

In an embodiment, a system is provided that includes a resonant sensor and one or more processors. The resonant sensor is configured to be in contact with oil within a gearbox of a rotor system. The sensor includes electrodes and a sensing region circuit that is configured to generate electrical stimuli at different times during an operational life of the gearbox. Each electrical stimulus has multiple different frequencies that are applied to the oil via the electrodes. The one or more processors are configured to receive multiple electrical signals from the resonant sensor. The electrical signals are representative of impedance responses of the oil to the electrical stimuli. The one or more processors are configured to analyze the impedance responses and determine a concentration of a polar analyte in the oil at each of the different times based on the impedance responses. The one or more processors are further configured to calculate a degradation value for the gearbox based on the concentration of the polar analyte in the oil. Responsive to the degradation value exceeding a designated degradation threshold, the one or more processors are configured to at least one of schedule maintenance for the rotor system, provide an alert to schedule maintenance for the rotor system, or prohibit operation of the rotor system until maintenance is performed on the rotor system.

Optionally, the resonant sensor is a multivariable sensor.

Optionally, the resonant sensor individually quantifies a concentration of at least one contaminant in the oil and a level of aging of the oil.

Optionally, the resonant sensor individually quantifies a concentration of molecularly dissolved water and a concentration of dispersed water in the oil.

Optionally, the polar analyte in the oil is at least one of an acidic component or water.

Optionally, the polar analyte in the oil is water. The system further includes a temperature sensor configured to monitor a temperature within the gearbox. The one or more processors are configured to calculate the degradation value for the gearbox based on the concentration of water in the oil during time periods that the temperature within the gearbox is less than an evaporation threshold temperature.

Optionally, the polar analyte in the oil is water. The system further includes a vibration sensor mounted to the rotor system. The vibration sensor is configured to detect that the rotor system is in a non-operating state based on an amount of vibration of the rotor system. The one or more processors are configured to calculate the degradation value for the gearbox based on the concentration of water in the oil during time periods that the rotor system is in the non-operating state.

Optionally, the resonant sensor is configured to generate the electrical stimuli periodically at intervals no greater than five minutes in duration in order for the one or more processors to periodically determine the concentration of the polar analyte in the oil during the operational life of the gearbox.

Optionally, the one or more processors are configured to calculate the degradation value as an integral of the concentration of the polar analyte in the oil over a time period in which the electrical stimuli are applied to the oil.

Optionally, the one or more processors are further configured to estimate a remaining amount of time in the operational life of the gearbox based on the degradation value for the gearbox. The remaining amount of time is inversely proportional to the degradation value.

Optionally, the one or more processors are configured to analyze the impedance response by extracting resonance parameters of the impedance response. The resonance parameters include one or more of a frequency position (Fp) and magnitude (Zp) of a real part of the impedance response, a resonant frequency (F1) and antiresonant frequency (F2) of an imaginary part of the impedance response, an impedance magnitude (Z1) at the resonant frequency (F1) and an impedance magnitude (Z2) at the antiresonant frequency (F2), and a zero-reactance frequency (Fz) at the imaginary part of the impedance response.

Optionally, the sensing region circuit of the resonant sensor includes at least one inductor-capacitor-resistor (LCR) resonant circuit.

Optionally, the system includes the rotor system, and the rotor system is a wind turbine.

In another embodiment, a method is provided that includes obtaining multiple measurements of a concentration of at least one polar analyte in oil within a gearbox of a rotor system. The measurements are obtained at different times during an operational life of the gearbox via a resonant sensor in operational contact with the oil. The resonant sensor includes electrodes and a sensing region circuit that is configured to generate an electrical stimulus having multiple different frequencies that are applied to the oil via the electrodes. The concentration of the at least one polar analyte in the oil is determined based on an impedance response of the oil to the electrical stimulus. The method also includes calculating a degradation value for the gearbox based on the concentration of the at least one polar analyte in the oil within the gearbox. Responsive to the degradation value exceeding a designated degradation threshold, the method includes at least one of scheduling maintenance for the rotor system, providing an alert to schedule maintenance for the rotor system, or prohibiting operation of the rotor system until maintenance is performed on the rotor system.

Optionally, the measurements of the concentration of the at least one polar analyte in the oil are obtained periodically at intervals no greater than five minutes in duration.

Optionally, the method further includes detecting that the rotor system is in a non-operating state. At least some of the measurements of the concentration of the polar analyte in oil are obtained while the rotor system is in the non-operating state.

Optionally, the designated degradation threshold is a first degradation threshold. Responsive to the degradation value exceeding the first degradation threshold, the method includes at least one of scheduling replacement of the oil within the gearbox or providing an alert to schedule replacement of the oil within the gearbox.

Optionally, responsive to the degradation value exceeding a second degradation threshold that is greater than the first degradation threshold, the method includes at least one of scheduling servicing of the gearbox or providing an alert to schedule servicing of the gearbox.

Optionally, the at least one polar analyte in the oil that is measured is at least one of an acidic component or water.

Optionally, the degradation value is calculated as an integral of the concentration of the at least one polar analyte in the oil over a time period that the measurements of the concentration are obtained.

Optionally, the method further includes estimating a remaining amount of time in the operational life of the gearbox based on the degradation value for the gearbox. The remaining amount of time is inversely proportional to the degradation value.

Optionally, the at least one polar analyte that is measured is water and the method further comprises monitoring a temperature of the oil within the gearbox. The degradation value for the gearbox is calculated based on measurements of the concentration of water in the oil that are obtained during time periods that the temperature of the oil is less than an evaporation threshold temperature.

Optionally, the at least one polar analyte that is measured is at least one of molecularly dissolved water or dispersed water.

Optionally, obtaining multiple measurements of the concentration of the at least one polar analyte in oil includes individually measuring a concentration of molecularly dissolved water in the oil and individually measuring a concentration of dispersed water in the oil.

Optionally, obtaining multiple measurements of the concentration of the at least one polar analyte in oil includes individually measuring a concentration of at least one contaminant in the oil and individually measuring a level of aging of the oil.

Optionally, the method further includes analyzing the impedance response of the oil to the electrical stimulus to determine both a concentration of at least one contaminant in the oil and a concentration of an additive package in the oil based on the impedance response.

In another embodiment, a system is provided that includes a resonant sensor, one or more processors, and an operating condition sensor. The resonant sensor is configured to be in contact with oil within a gearbox of a rotor system. The sensor includes electrodes and a sensing region circuit that is configured to generate electrical stimuli at different times during an operational life of the gearbox. Each electrical stimulus has multiple different frequencies that are applied to the oil via the electrodes. The one or more processors are configured to receive multiple electrical signals from the resonant sensor. The electrical signals are representative of impedance responses of the oil to the electrical stimuli. The one or more processors are configured to analyze the impedance responses and determine a concentration of water in the oil at each of the different times based on the impedance responses. The operating condition sensor is mounted to the rotor system. The operating condition sensor is configured to detect when the rotor system is in a non-operating state and when the rotor system is in an operating state. The one or more processors are configured to calculate a degradation value for the gearbox based on the concentration of water in the oil during time periods that the rotor system is in the non-operating state. Responsive to the degradation value exceeding a designated degradation threshold, the one or more processors are configured to at least one of schedule maintenance for the rotor system, provide an alert to schedule maintenance for the rotor system, or prohibit operation of the rotor system until maintenance is performed on the rotor system.

Optionally, the operating condition sensor is at least one of a vibration sensor, a temperature sensor, an electrical switch sensor, or an optical sensor.

Optionally, the resonant sensor individually quantifies a concentration of molecularly dissolved water and a concentration of dispersed water in the oil.

Optionally, the resonant sensor individually quantifies a concentration of at least one contaminant in the oil and a concentration of an additive package in the oil based on the impedance response.

The term "multivariable sensor" is referred to herein as a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof.

The term "multivariate analysis" refers to a mathematical procedure that is used to analyze more than one variable from the sensor response and to provide the information about the type of at least one environmental parameter from the measured sensor parameters and/or to quantitative information about the level of at least one environmental parameter from the measured sensor parameters. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" is used to refer to measurable variables of the sensor response. The sensor response is the impedance spectrum of the LCR sensor. In addition to measuring the impedance spectrum in the form of Z-parameters, S-parameters, and other parameters, the impedance spectrum (for example, both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance (F1), the anti-resonant frequency of the imaginary part of the impedance (F2), signal magnitude (Z1) at the resonant frequency of the imaginary part of the impedance (F1), signal magnitude (Z2) at the anti-resonant frequency of the imaginary part of the impedance (F2), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra may also be called "features" or "descriptors." The appropriate selection of features is performed from all potential features that can be calculated from spectra.

As used herein the term "sensing materials and sensing films" includes, but is not limited to, materials deposited onto a transducer's electronics circuit components, such as LCR circuit components to perform the function of predictably and reproducibly affecting the impedance sensor response upon interaction with the environment. In order to prevent the material in the sensor film from leaching into the liquid environment, the sensing materials are attached to the sensor surface using standard techniques, such as covalent bonding, electrostatic bonding, and other standard techniques known to those of ordinary skill in the art.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
   a resonant sensor configured to be in contact with oil within a gearbox of a rotor system, the sensor including electrodes and a sensing region circuit that is configured to generate electrical stimuli at different times during an operational life of the gearbox, each electrical stimulus having multiple different frequencies that are applied to the oil via the electrodes; and
   one or more processors configured to receive multiple electrical signals from the resonant sensor, the electrical signals representative of impedance responses of the oil to the electrical stimuli, the one or more processors configured to analyze the impedance responses and determine a concentration of a polar analyte in the oil at each of the different times based on the impedance responses, the one or more processors further configured to calculate a degradation value for the gearbox based on the concentration of the polar analyte in the oil,
   wherein, responsive to the degradation value exceeding a designated degradation threshold, the one or more processors are configured to at least one of schedule maintenance for the rotor system, provide an alert to schedule maintenance for the rotor system, or prohibit operation of the rotor system until maintenance is performed on the rotor system;
   wherein the one or more processors are configured to calculate the degradation value as an integral of the concentration of the polar analyte in the oil over a time period in which the electrical stimuli are applied to the oil; and
   wherein determining the concentration of the polar analyte includes individually measuring a concentration of at least one contaminant in the oil and individually measuring a level of aging of the oil.

2. The system of claim 1, wherein the resonant sensor is a multivariable sensor.

3. The system of claim 1, wherein the resonant sensor individually quantifies a concentration of at least one contaminant in the oil and a level of aging of the oil.

4. The system of claim 1, wherein the resonant sensor individually quantifies a concentration of molecularly dissolved water and a concentration of dispersed water in the oil.

5. The system of claim 1, wherein the polar analyte in the oil is at least one of an acidic component or water.

6. The system of claim 1, wherein the polar analyte in the oil is water, the system further comprising a temperature sensor configured to monitor a temperature within the gearbox, the one or more processors configured to calculate the degradation value for the gearbox based on the concentration of water in the oil during time periods that the temperature within the gearbox is less than an evaporation threshold temperature.

7. The system of claim 1, wherein the polar analyte in the oil is water, the system further comprising a vibration sensor mounted to the rotor system, the vibration sensor configured to detect that the rotor system is in a non-operating state based on an amount of vibration of the rotor system, the one or more processors configured to calculate the degradation value for the gearbox based on the concentration of water in the oil during time periods that the rotor system is in the non-operating state.

8. The system of claim 1, wherein the resonant sensor is configured to generate the electrical stimuli periodically at intervals no greater than five minutes in duration in order for the one or more processors to periodically determine the concentration of the polar analyte in the oil during the operational life of the gearbox.

9. The system of claim 1, wherein the one or more processors are further configured to estimate a remaining amount of time in the operational life of the gearbox based on the degradation value for the gearbox, the remaining amount of time inversely proportional to the degradation value.

10. The system of claim 1, wherein the one or more processors are configured to analyze the impedance response by extracting resonance parameters of the impedance response, the resonance parameters including one or more of a frequency position (Fp) and magnitude (Zp) of a real part of the impedance response, a resonant frequency (F1) and antiresonant frequency (F2) of an imaginary part of the impedance response, an impedance magnitude (Z1) at the resonant frequency (F1) and an impedance magnitude (Z2) at the antiresonant frequency (F2), and a zero-reactance frequency (Fz) at the imaginary part of the impedance response.

11. The system of claim 1, wherein the sensing region circuit of the resonant sensor includes at least one inductor-capacitor-resistor (LCR) resonant circuit.

12. The system of claim 1, further comprising the rotor system, wherein the rotor system is a wind turbine.

13. A method comprising:
   obtaining multiple measurements of a concentration of at least one polar analyte in oil within a gearbox of a rotor system, the measurements obtained at different times during an operational life of the gearbox via a resonant sensor in operational contact with the oil, the resonant sensor including electrodes and a sensing region circuit that is configured to generate an electrical stimulus having multiple different frequencies that are applied to the oil via the electrodes, the concentration of the at least one polar analyte in the oil determined based on an impedance response of the oil to the electrical stimulus;

calculating a degradation value for the gearbox based on the concentration of the at least one polar analyte in the oil within the gearbox;

responsive to the degradation value exceeding a designated degradation threshold, at least one of scheduling maintenance for the rotor system, providing an alert to schedule maintenance for the rotor system, or prohibiting operation of the rotor system until maintenance is performed on the rotor system;

wherein the degradation value is calculated as an integral of the concentration of the at least one polar analyte in the oil over a time period that the measurements of the concentration are obtained; and wherein obtaining multiple measurements of the concentration of the at least one polar analyte in oil includes individually measuring a concentration of at least one contaminant in the oil and individually measuring a level of aging of the oil.

14. The method of claim 13, wherein the measurements of the concentration of the at least one polar analyte in the oil are obtained periodically at intervals no greater than five minutes in duration.

15. The method of claim 13, further comprising detecting that the rotor system is in a non-operating state, wherein at least some of the measurements of the concentration of the polar analyte in oil are obtained while the rotor system is in the non-operating state.

16. The method of claim 13, wherein the designated degradation threshold is a first degradation threshold and responsive to the degradation value exceeding the first degradation threshold, the method includes at least one of scheduling replacement of the oil within the gearbox or providing an alert to schedule replacement of the oil within the gearbox, and wherein, responsive to the degradation value exceeding a second degradation threshold that is greater than the first degradation threshold, the method includes at least one of scheduling servicing of the gearbox or providing an alert to schedule servicing of the gearbox.

17. The method of claim 13, further comprising estimating a remaining amount of time in the operational life of the gearbox based on the degradation value for the gearbox, the remaining amount of time inversely proportional to the degradation value.

18. The method of claim 13, wherein the at least one polar analyte that is measured is water and the method further comprises monitoring a temperature of the oil within the gearbox, the degradation value for the gearbox calculated based on measurements of the concentration of water in the oil that are obtained during time periods that the temperature of the oil is less than an evaporation threshold temperature.

19. The method of claim 13, further comprising analyzing the impedance response of the oil to the electrical stimulus to determine both a concentration of at least one contaminant in the oil and a concentration of an additive package in the oil based on the impedance response.

20. The method of claim 13, wherein obtaining multiple measurements of a concentration of at least one polar analyte in oil comprises obtaining multiple measurements of the concentration of at least two polar analytes.

21. A system comprising:

a resonant sensor configured to be in contact with oil within a gearbox of a rotor system, the sensor including electrodes and a sensing region circuit that is configured to generate electrical stimuli at different times during an operational life of the gearbox, each electrical stimulus having multiple different frequencies that are applied to the oil via the electrodes;

one or more processors configured to receive multiple electrical signals from the resonant sensor, the electrical signals representative of impedance responses of the oil to the electrical stimuli, the one or more processors configured to analyze the impedance responses and determine a concentration of water in the oil at each of the different times based on the impedance responses;

an operating condition sensor mounted to the rotor system, the operating condition sensor configured to detect when the rotor system is in a non-operating state and when the rotor system is in an operating state, wherein the one or more processors are configured to calculate a degradation value for the gearbox based on the concentration of water in the oil during time periods that the rotor system is in the non-operating state, and, responsive to the degradation value exceeding a designated degradation threshold, the one or more processors are configured to at least one of schedule maintenance for the rotor system, provide an alert to schedule maintenance for the rotor system, or prohibit operation of the rotor system until maintenance is performed on the rotor system;

wherein the one or more processors are configured to calculate the degradation value as an integral of the concentration of the polar analyte in the oil over a time period in which the electrical stimuli are applied to the oil; and wherein the resonant sensor individually quantifies a concentration of at least one contaminant in the oil and a concentration of an additive package in the oil based on the impedance response.

22. The system of claim 19, wherein the operating condition sensor is at least one of a vibration sensor, a temperature sensor, an electrical switch sensor, or an optical sensor.

* * * * *